US010882843B2

(12) United States Patent
Wu

(10) Patent No.: US 10,882,843 B2
(45) Date of Patent: Jan. 5, 2021

(54) 5-AMINOPYRAZOLE CARBOXAMIDE DERIVATIVE AS BTK INHIBITOR AND PREPARATION METHOD AND PHARMACEUTICAL COMPOSITION THEREOF

(71) Applicant: SUZHOU SINOVENT PHARMACEUTICALS CO., LTD., Suzhou (CN)

(72) Inventor: Yuchuan Wu, Beijing (CN)

(73) Assignee: SUZHOU SINOVENT PHARMACEUTICALS CO., LTD., Suzhou (CN)

( * ) Notice: Subject to any disclaimer, the term of this patent is extended or adjusted under 35 U.S.C. 154(b) by 0 days.

(21) Appl. No.: 16/302,036

(22) PCT Filed: Apr. 25, 2017

(86) PCT No.: PCT/CN2017/081906
§ 371 (c)(1),
(2) Date: Nov. 15, 2018

(87) PCT Pub. No.: WO2017/198050
PCT Pub. Date: Nov. 23, 2017

(65) Prior Publication Data
US 2019/0152952 A1 May 23, 2019

(30) Foreign Application Priority Data
May 16, 2016 (CN) .......................... 2016 1 0323755

(51) Int. Cl.
| A61K 31/4439 | (2006.01) |
| C07D 401/14 | (2006.01) |
| C07D 413/14 | (2006.01) |
| C07D 401/04 | (2006.01) |
| A61K 31/454 | (2006.01) |
| A61K 31/5377 | (2006.01) |
| A61K 31/497 | (2006.01) |
| C07D 403/14 | (2006.01) |
| A61K 31/496 | (2006.01) |
| A61K 31/4545 | (2006.01) |
| A61K 31/444 | (2006.01) |
| A61P 35/00 | (2006.01) |
| C07D 403/04 | (2006.01) |

(52) U.S. Cl.
CPC .......... *C07D 401/14* (2013.01); *A61K 31/444* (2013.01); *A61K 31/4439* (2013.01); *A61K 31/454* (2013.01); *A61K 31/4545* (2013.01); *A61K 31/496* (2013.01); *A61K 31/497* (2013.01); *A61K 31/5377* (2013.01); *A61P 35/00* (2018.01); *C07D 401/04* (2013.01); *C07D 403/04* (2013.01); *C07D 403/14* (2013.01); *C07D 413/14* (2013.01); *Y02P 20/55* (2015.11)

(58) Field of Classification Search
None
See application file for complete search history.

(56) References Cited

U.S. PATENT DOCUMENTS

| 2015/0005277 A1 | 1/2015 | Wang et al. |
| 2017/0144986 A1 | 5/2017 | Han et al. |

FOREIGN PATENT DOCUMENTS

| CN | 103848810 A | 6/2014 |
| CN | 105008344 A | 10/2015 |
| CN | 105085474 A | 11/2015 |
| EP | 3141546 A1 | 3/2017 |
| WO | WO-2014068527 A1 | 5/2014 |
| WO | WO-2014082598 A1 | 6/2014 |

OTHER PUBLICATIONS

International Search Report for Application No. PCT/CN2017/081906, dated Jun. 14, 2017.
Extended European Search Report for Application No. 17798613.0, dated Dec. 10, 2019.

*Primary Examiner* — Samantha L Shterengarts
(74) *Attorney, Agent, or Firm* — Marshall, Gerstein & Borun LLP

(57) ABSTRACT

The present application discloses novel 5-aminopyrazole carboxamide compounds as shown in formula (I), and stereoisomers, pharmaceutically acceptable salts, solvates, or prodrugs thereof. In addition, the present application further discloses a method for the preparation of the compounds, a pharmaceutical composition comprising a compound of the invention and the use of the compounds.

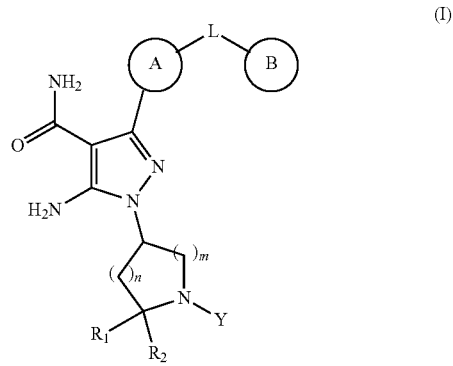

7 Claims, 1 Drawing Sheet

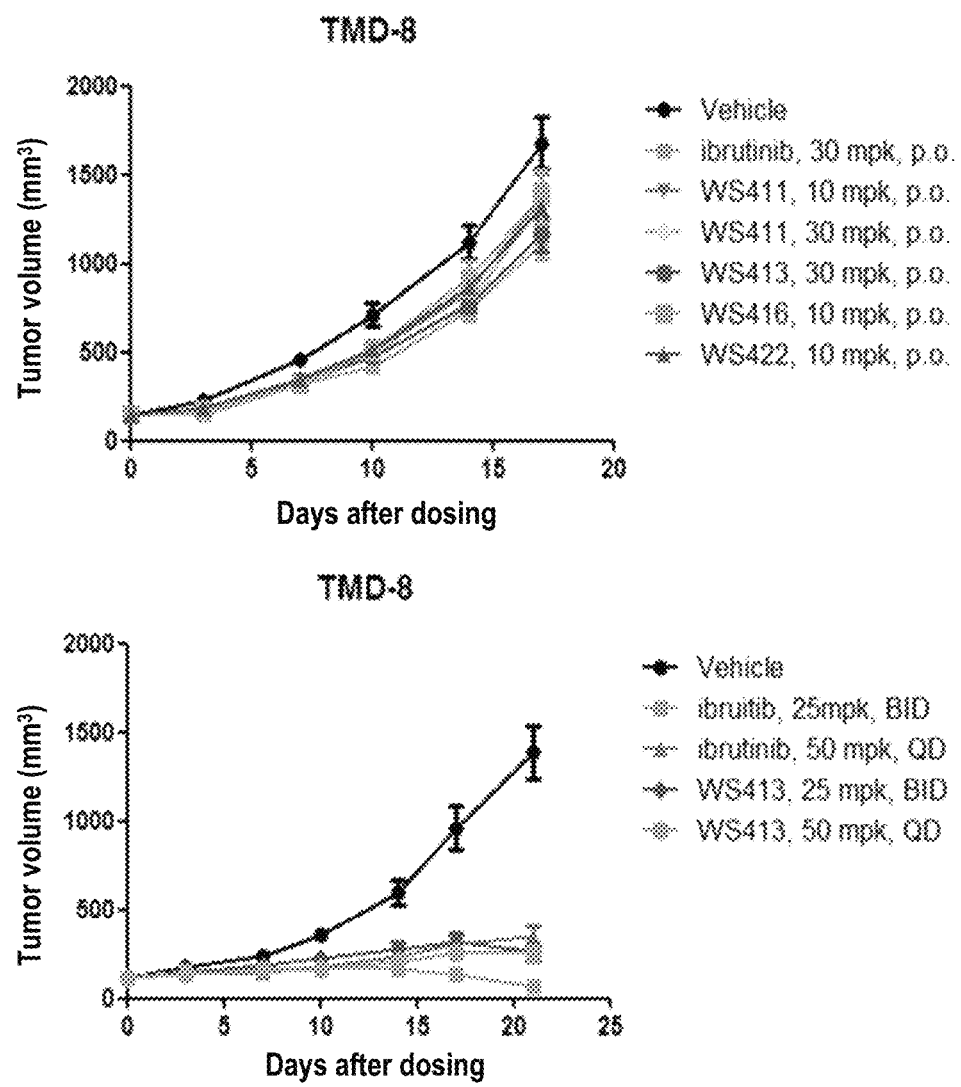

5-AMINOPYRAZOLE CARBOXAMIDE DERIVATIVE AS BTK INHIBITOR AND PREPARATION METHOD AND PHARMACEUTICAL COMPOSITION THEREOF

TECHNICAL FIELD

The present invention belongs to the technical field of medicinal chemistry, in particular involves a novel and potent 5-aminopyrazole carboxamide derivative as a BTK inhibitor, which exhibits high selectivity and good pharmacokinetic properties, as well as a preparation method and a pharmaceutical composition comprising the same.

BACKGROUND OF THE INVENTION

Protein kinases represent the largest family of biological enzymes in human, including over 500 proteins. In particular, for tyrosine kinases, the phenolic functional group on a tyrosine residue is capable of being phosphorylated to exert important biosignaling effects. The members of tyrosine kinase family control cell growth, migration, and differentiation. It has been illustrated that abnormal kinase activities are closely associated with many human diseases, including cancers, autoimmune diseases, and inflammatory diseases.

Bruton's tyrosine kinase (BTK) is a cytoplasmic non-receptor tyrosine kinase, and is one member of the TEC kinase family (including a total of five members BTK, TEC, ITK, TXK, and BMX). The BTK gene is located at Xq21.33-Xq22 on the X-chromosome and has 19 exons in total spanning 37.5 kb of genomic DNA.

BTK is expressed on almost all hematopoietic cells (except for T cells and plasma cells), and particularly plays an essential role in the development, differentiation, signaling and survival of B lymphocytes. B cells are activated via the B cell receptor (BCR), and BTK plays a critical role in the BCR signaling pathway. Activation of BCR on B cells causes activation of BTK, which in turn leads to an increase in downstream phospholipase C (PLC) concentration and activates the IP3 and DAG signaling pathways. This signaling pathway can promote cell proliferation, adhesion and survival. A mutation in the BTK gene will result in a rare genetic B cell-specific immunodeficiency disease, known as X-linked agammaglobulinemia (XLA). In this disease, the function of BTK is inhibited, resulting in the retardance of the production or maturation of B cells. Men suffering from the XLA disease have almost no B cells in their bodies, and have few circulating antibodies, proning to serious or even fatal infections. This strongly proves that BTK plays an extremely important role in the growth and differentiation of B cells.

A small molecule BTK inhibitor can bind to BTK, inhibit autophosphorylation of BTK, and prevent the activation of BTK. This can block the signal transduction through the BCR pathway, inhibit the proliferation of B lymphoma cells, destroy the adhesion of tumor cells, and promote the apoptosis of tumor cells, inducing apoptosis. This makes BTK become an attractive drug target in B cell-associated cancers, especially B-cell lymphomas and leukemias such as non-Hodgkin's lymphoma (NHL), chronic lymphocytic leukemia (CLL), and recurrent or refractory mantle cell lymphoma (MCL), etc.

In addition to inhibiting B-cell lymphoma and leukemia, BTK inhibitors can also inhibit the production of autoantibodies and cytokines of B cells. In an autoimmune disease, B cells present autoantigens, and promote the activation and secretion of pro-inflammatory factors of T cells, which cause tissue damage as well as activate B cells to produce a large number of antibodies, thereby triggering autoimmune responses. The interaction of T cells and B cells constitutes a feedback regulation chain, causing uncontrolled autoimmune response and exacerbated histopathological damage. Therefore, BTK can be served as a drug target for the treatment of autoimmune diseases such as rheumatoid arthritis, systemic lupus erytllematosus (SLE), and allergic diseases diseases such as esophagitis, etc).

In addition, it has also been reported that BTK inhibitors can be used in combination with a chemotherapeutic agent or an immunological checkpoint inhibitor, showing better therapeutic effects on multiple solid tumors in clinical trials.

Among the currently marketed drugs, Ibrutinib is an irreversible BTK inhibitor jointly developed by Pharmacyclics and Johnson & Johnson, and has been approved by the FDA for the treatment of mantle cell lymphocytes (MCL) and chronic lymphocytic leukemia (CLL) in November 2013 and February 2014, respectively. Ibrutinib has been designated by the FDA as a "breakthrough" new drug that inactivate the BTK enzyme by reacting with a thiol group on cysteine in BTK and forming a covalent bond, thereby achieving its therapeutic effects. However, ibrutinib is easily metabolized (oxidatively metabolized into dihydroxylation products by metabolic enzymes or inactivated by attacking of other thiol-containing enzymes, cysteine, glutathione, etc.) during administration, thereby affecting the therapeutic effects. The clinically administered dose might reach 560 mg per day, which increased the burden on the patient. In addition, Ibrutinib also has some inhibitory effects on some kinases other than BTK, especially the inhibition of EGFR may cause more serious adverse reactions such as rash, diarrhea and others. Therefore, there is still a need in the art to develop a new class of BTK inhibitors that are more efficient, selective, and have good pharmacokinetic properties for the treatment of relevant diseases.

SUMMARY OF THE INVENTION

The following is a summary of the subject matter described in detail in the present application. However, it is not intended to limit the scopes of the claims.

The present inventors have developed a class of novel 5-aminopyrazole carboxamide derivatives which are an effective, safe and highly selective inhibitor of protein kinase BTK.

An embodiment of the present invention provides a novel 5-aminopyrazole carboxamide derivative. It is a new covalent inhibitor that improves its affinity with the target by altering its reactivity with cysteine, thereby improving its efficacy, selectivity and safety.

An embodiment s present invention also provides a preparation method of the above derivative.

An embodiment of the present invention also provides a pharmaceutical composition comprising the above derivative.

An embodiment of the present invention also provides the use of the above derivative.

Specifically, in an embodiment of the present invention, the present invention provides a novel 5-aminopyrazole carboxamide compound represented by formula (I):

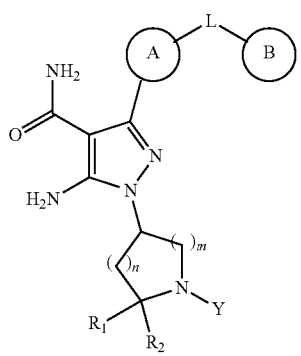

(I)

wherein, n and m are independently selected from 0, 1 or 2;

L is O, —C(O)NH—, —CH$_2$—, S, S(O), NH or S(O)$_2$;

A is selected from a substituted or unsubstituted heterocyclic ring, a substituted or unsubstituted benzene ring, or a substituted or unsubstituted heteroaryl ring, and its attachment sites to the parent nucleus and L may be optionally selected;

B is independently selected from a substituted or unsubstituted aliphatic ring, a substituted or unsubstituted heterocyclic ring, a substituted or unsubstituted benzene ring, or a substituted or unsubstituted heteroaryl ring, and its attachment site to L may be optionally selected;

$R_1$ and $R_2$ are each independently selected from hydrogen, $C_1$-$C_4$ alkyl, halogen, and cyano, or $R_1$ and $R_2$ together with the carbon atom to which they are attached form a three- or four-membered carbon ring, or $R_1$ and $R_2$ are combined to form an oxo group;

Y is selected from cyano,

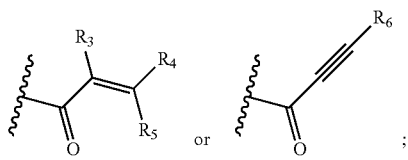

$R_3$, $R_4$, $R_5$ and $R_6$ are each independently selected from hydrogen, unsubstituted $C_1$-$C_4$ alkyl, hydroxy substituted $C_1$-$C_4$ alkyl, $C_1$-$C_4$ alkoxy $C_{1-4}$ alkyl, halogen, cyano, or —(CH$_2$)$_q$N(R$_a$R$_b$), wherein q is 1, 2, 3, or 4, and R$_a$ and R$_b$ are each independently selected from hydrogen, and unsubstituted $C_1$-$C_4$ alkyl;

with the provision that when one of $R_1$ and $R_2$ is hydrogen and the other is methyl, Y is cyano, A is a benzene ring, L is O, m is 1 and n is 2, B is not a substituted or unsubstituted benzene ring; when both $R_1$ and $R_2$ are hydrogen, A is a benzene ring, m is 1 and n is 2, B is not a substituted or unsubstituted benzene ring, or a substituted or unsubstituted pyridine ring; when both $R_1$ and $R_2$ are hydrogen, A is a pyridine ring, m is 1 and n is 2, B is not a substituted or unsubstituted benzene ring; when both $R_1$ and $R_2$ are hydrogen, A is a benzene ring, L is O, m is 1 and n is 1, B is not a substituted or unsubstituted benzene ring, or a stereoisomer, tautomer, pharmaceutically acceptable salt, solvate, or prodrug thereof.

In one embodiment of the present invention, the present invention provides a 5-aminopyrazole carboxamide compound of the formula (I), wherein n and m are independently selected from 0, 1, or 2; L is O, —C(O)NH—, —CH$_2$—, NH or S, more preferably O, —C(O)NH—, or NH.

In one embodiment of the present invention, the present invention provides a 5-aminopyrazole carboxamide compound of the formula (I), wherein A is selected from a substituted or unsubstituted heterocyclic ring, a substituted or unsubstituted benzene ring, or a substituted or unsubstituted heteroaryl ring, and its attachment sites to the parent nucleus and L may be optionally selected; B is independently selected from a substituted or unsubstituted aliphatic ring, a substituted or unsubstituted heterocyclic ring, a substituted or unsubstituted benzene ring, or a substituted or unsubstituted heteroaryl ring, and its attachment site to L may be optionally selected; wherein:

The substituted benzene ring means that any position on the phenyl group is optionally substituted with a substituent selected from the group consisting of hydrogen, methyl, methoxy, fluoro, chloro, trifluoromethyl, trifluoromethoxyl and cyano group; preferably, the substituted benzene ring is a fluoro substituted phenyl group, or a chloro substituted phenyl group, more preferably a 2,4-difluorophenyl group, or a 4-chlorophenyl group;

The unsubstituted heteroaryl ring means furan, pyrrole, thiophene, oxazole, isoxazole, pyrazole, imidazole, thiazole isothiazole, oxadiazole, triazole, thiadiazole, tetrazolium, pyridine, pyrimidine, pyrazine, pyridazine, or triazine; and the substituted heteroaryl ring means the above groups with an optional substituent selected from the group consisting of hydrogen, methyl, methoxyl, fluoro, chloro, trifluoromethyl, trifluoromethoxyl and cyano at any position(s); more preferably, the substituted pyridine is chloropyridine, particularly preferably 4-chloro-pyridin-2-yl;

The unsubstituted aliphatic ring means cyclopropane, cyclobutane, cyclopentane, cyclohexane, cycloheptane, or cyclooctane; the substituted aliphatic ring means the above groups with an optional substituent selected from the group consisting of hydrogen, methyl, methoxyl, fluoro, chloro, trifluoromethyl, trifluoromethoxy and cyano at any position(s);

The unsubstituted heterocyclic ring means tetrahydrofuran, tetrahydropyran, tetrahydropyrrole, piperidine,

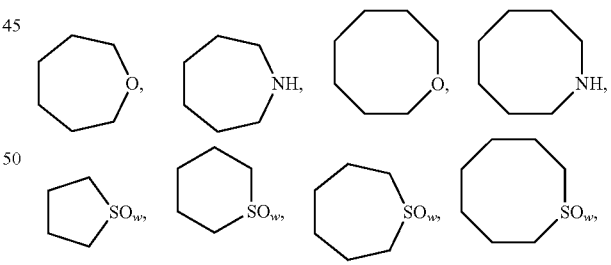

wherein w is selected from 0, 1 or 2; the substituted heterocyclic ring means the above groups with an optional substituent selected from the group consisting of hydrogen, methyl, methoxy, fluoro, chloro, trifluoromethyl, trifluoromethoxy and cyano at any position(s).

In one embodiment of the present invention, the present invention provides a 5-aminopyrazole carboxamide compound of the formula (I), wherein preferably, both $R_1$ and $R_2$ are hydrogen or one of them is hydrogen and the other is a $C_1$-$C_4$ alkyl group (methyl, ethyl, n-propyl, isopropyl, n-butyl, isobutyl, or t-butyl), or $R_1$ and $R_2$ together with the carbon atom to which they are attached form a cyclopropyl group; more preferably, both $R_1$ and $R_2$ are hydrogen, or one of them is hydrogen and the other is methyl, or $R_1$ and $R_2$ together with the carbon atom to which they are attached form a cyclopropyl group.

In a preferred embodiment of the present invention, the present invention provides a 5-aminopyrazole carboxamide compound represented by formula (II):

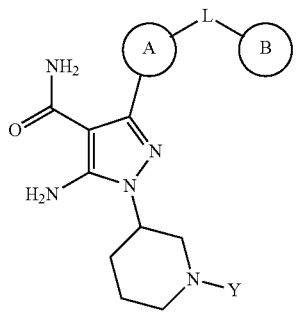

(II)

wherein,

L, A, B and Y are defined as in the above formula (I);

with the provision that when A is a benzene ring, B is not a substituted or unsubstituted benzene ring, or a substituted or unsubstituted pyridine ring; when A is a pyridine ring, B is not a substituted or unsubstituted benzene ring, or a stereoisomer, a tautomer, a pharmaceutically acceptable salt, a solvate, or a prodrug thereof.

In a more preferred embodiment of the present invention, the 5-aminopyrazole carboxamide compound of the formula (II) provided by the present invention is one of the following compounds:

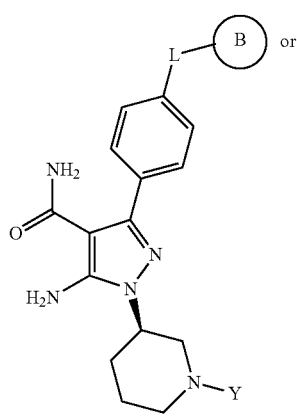

(II-1)

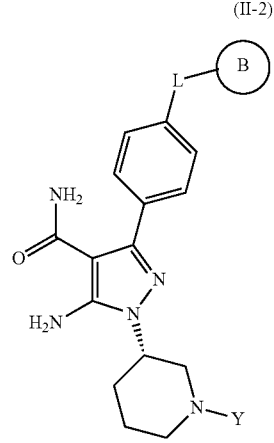

(II-2)

wherein, L, B and Y in the formula (II-1) or II-2) are defined as in the above formula (I);

with the provision that B is not a substituted or unsubstituted benzene ring, or a substituted or unsubstituted pyridine ring.

In a preferred embodiment of the present invention, the present invention provides a 5-aminopyrazole carboxamide compound represented by formula (III):

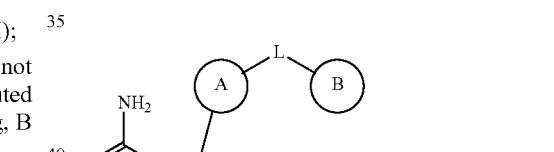

(III)

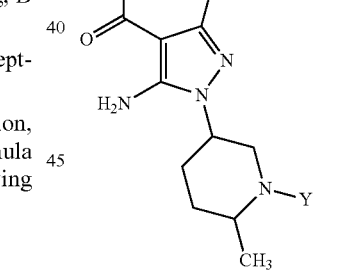

wherein L, A, B and Y are defined as in the above formula (I);

with the provision that when Y is a cyano group, A is a benzene ring, and L is O, B is not a substituted or unsubstituted benzene ring, or a stereoisomer, a tautomer, a pharmaceutically acceptable salt, a solvate, or a prodrug thereof.

In a more preferred embodiment of the present invention, the 5-aminopyrazole carboxamide compound of the formula (III) provided by the present invention is one of the following compounds:

(III-1)

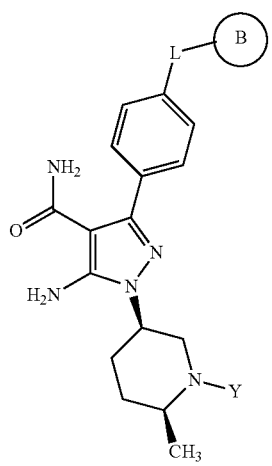

(III-2)

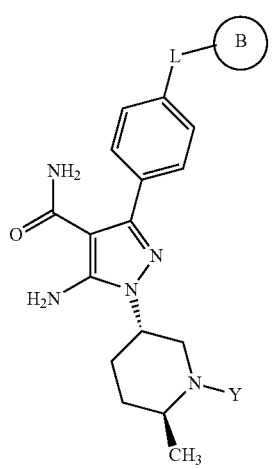

(III-3)

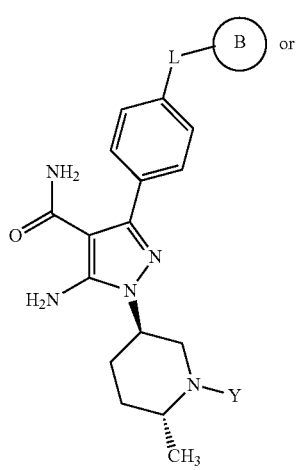 or (III-4)

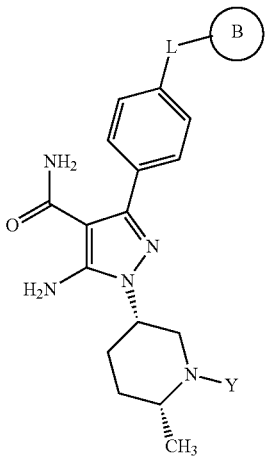

wherein L, B and Y in the formulae (III-1), (III-2), (III-3) and (III-4) are defined as in the above formula (I);

with the provision that when Y is a cyano group and L is O, B is not a substituted or unsubstituted benzene ring.

In a preferred embodiment of the present invention, the present invention provides a 5-aminopyrazole carboxamide compound represented by the formula (IV):

(IV)

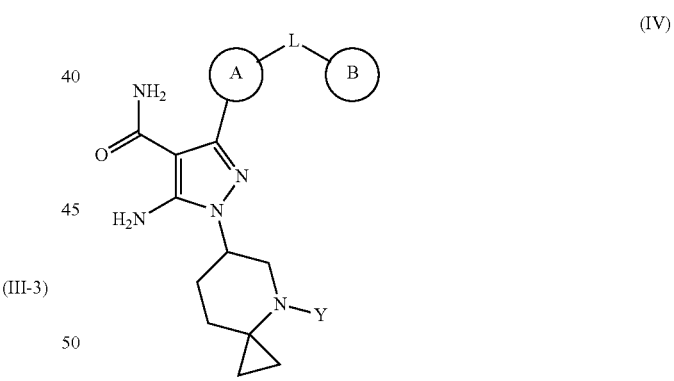

wherein L, A, B, and Y are as defined in the above formula (I), or a stereoisomer, a tautomer, a pharmaceutically acceptable salt, a solvate, or a prodrug thereof.

In a more preferred embodiment of the present invention, the 5-aminopyrazole carboxamide compound of the formula (IV) provided by the present invention is one of the following compounds:

(IV-1)

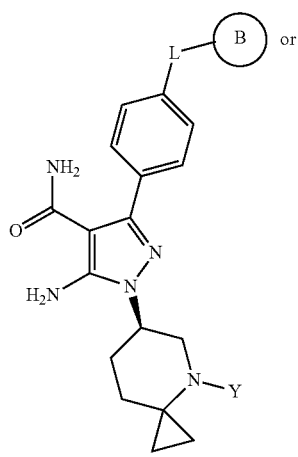

and

Y is —CN,

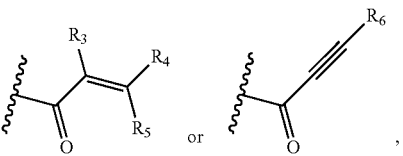

wherein $R_3$, $R_4$, $R_5$ and $R_6$ are each independently selected from hydrogen, unsubstituted $C_1$-$C_4$ alkyl, hydroxy-substituted $C_1$-$C_4$ alkyl, $C_1$-$C_4$ alkoxy $C_1$-$C_4$ alkyl, halogen, cyano or —$(CF_2)_q N(R^a R^b)$, wherein q is 1, 2, 3, or 4, and $R^a$ and $R^b$ are each independently selected from hydrogen, or unsubstituted $C_1$-$C_4$ alkyl.

In a particularly preferred embodiment of the present invention, the 5-aminopyrazole carboxamide compound provided by the present invention is one selected from the following compounds:

(IV-2)

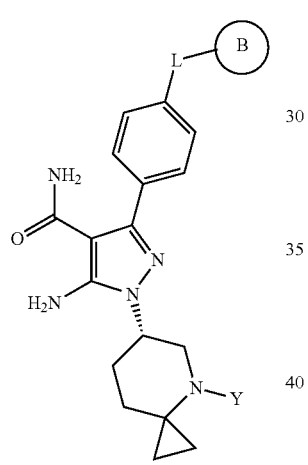

wherein L, B and Y in the formula (IV-1) or (IV-2) are defined as in the above formula (I).

In a more preferred embodiment of the present invention, the present invention provides the compounds of formula (I), (II), (II-1), (III), (III-1), (III-2), (III-3), (III-4), (IV), (IV-1), or (IV-2), wherein L is O;

B is

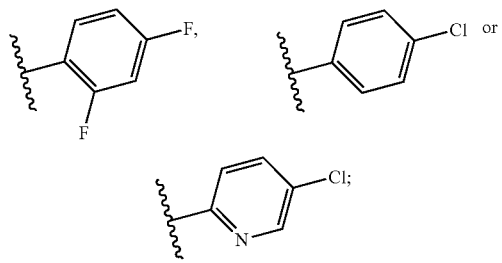

WS-400

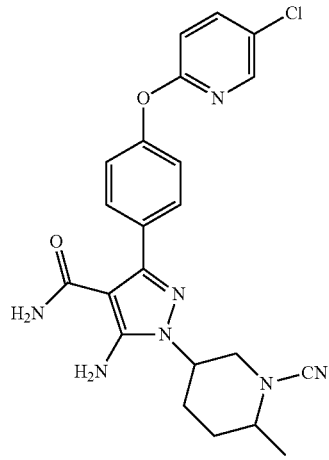

WS-401

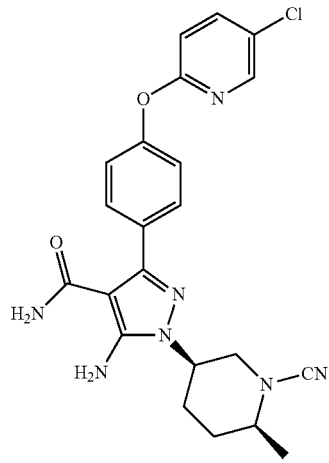

-continued
WS-402
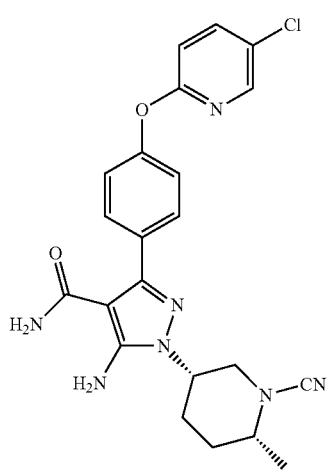
WS-403
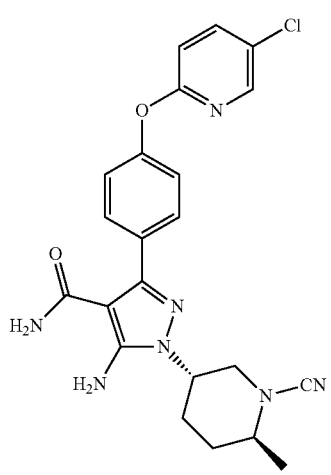
WS-404
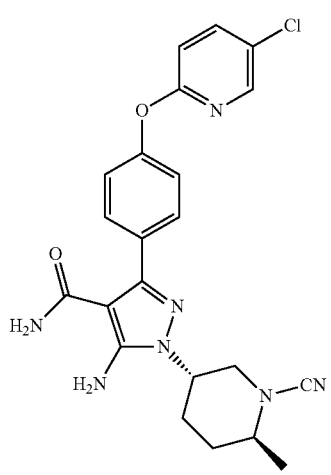
-continued
WS-405
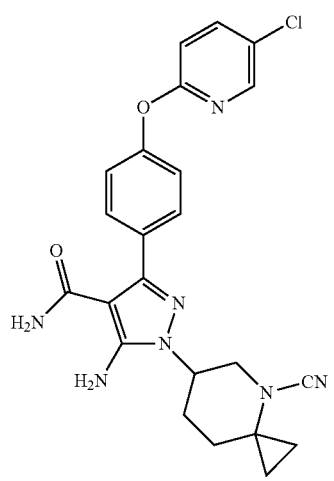
WS-406
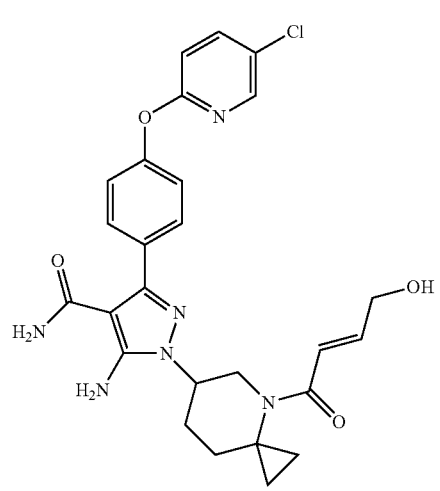
WS-407
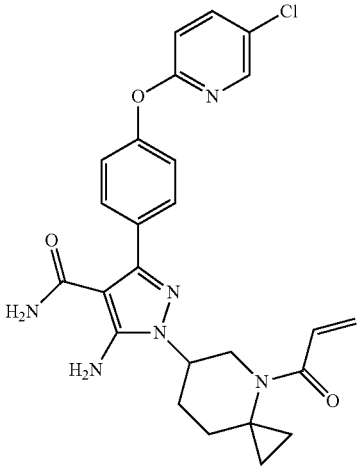

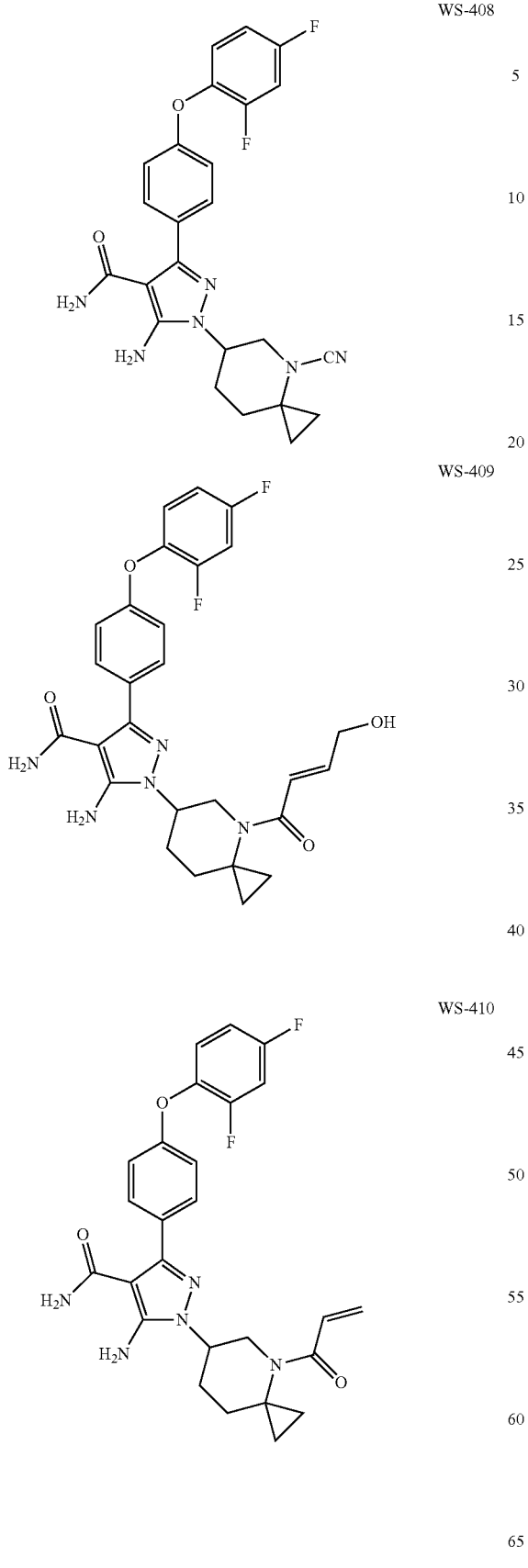
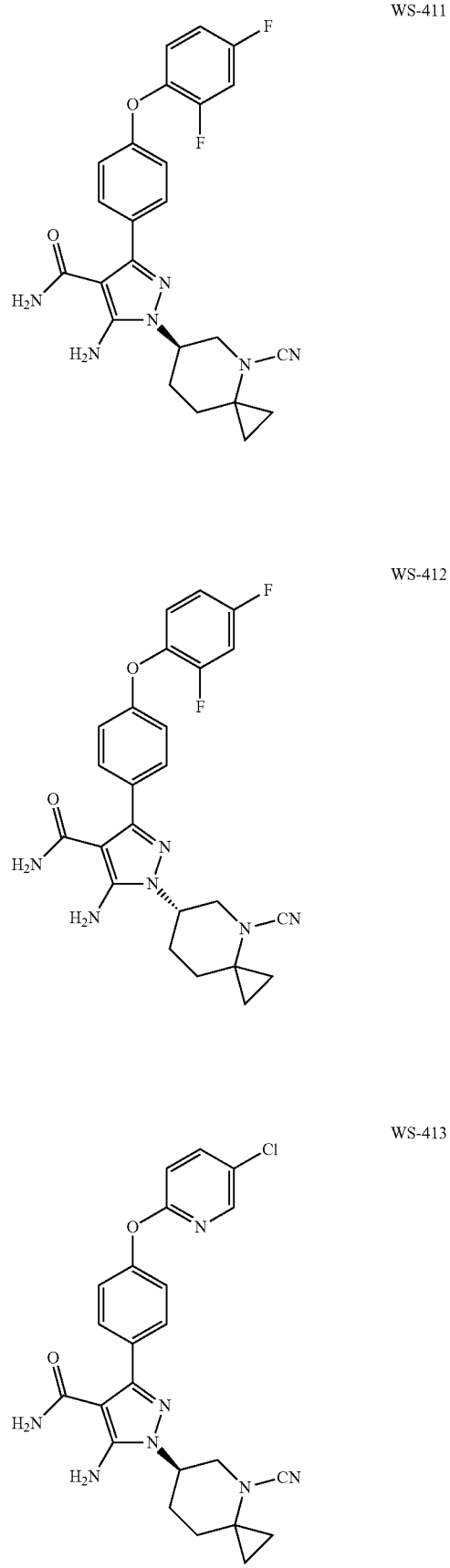

WS-414
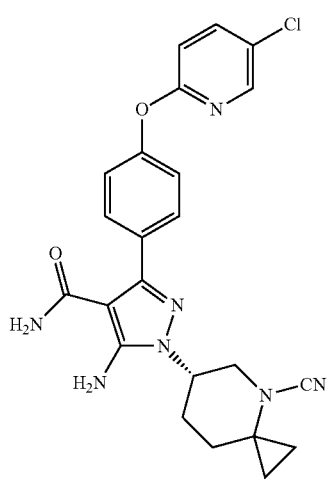
WS-415
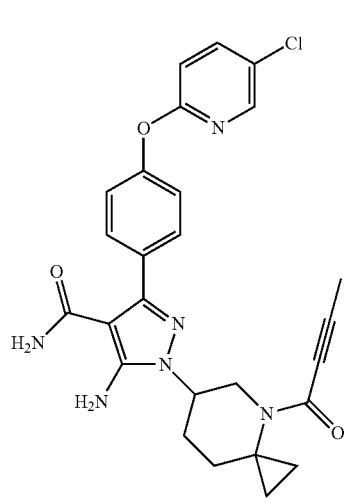
WS-416
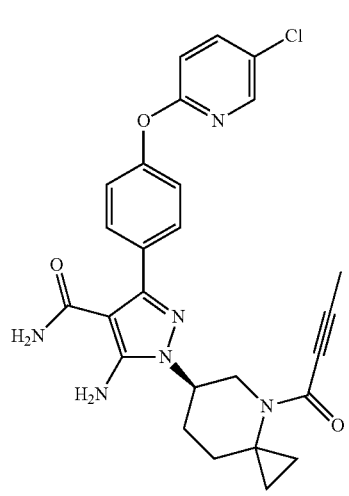
WS-417
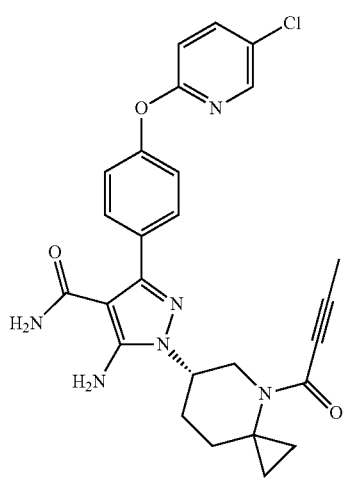
WS-418
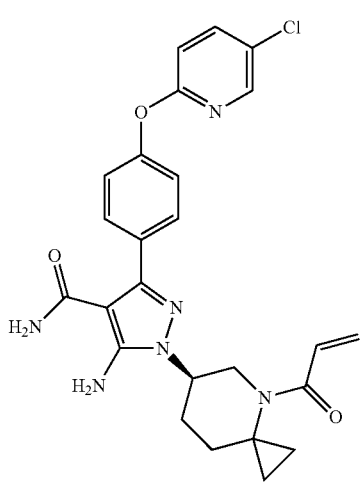
WS-419
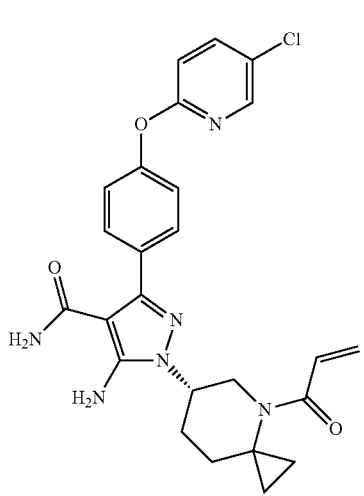

-continued
WS-420
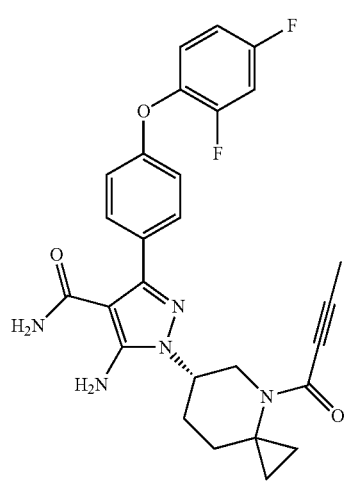
WS-421
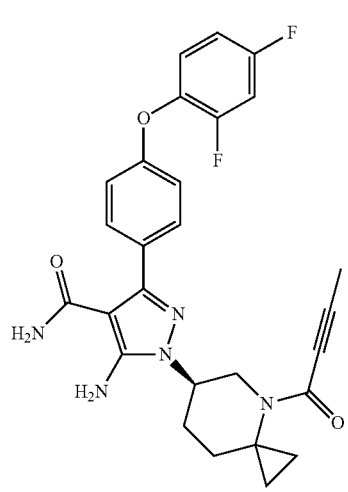
WS-422
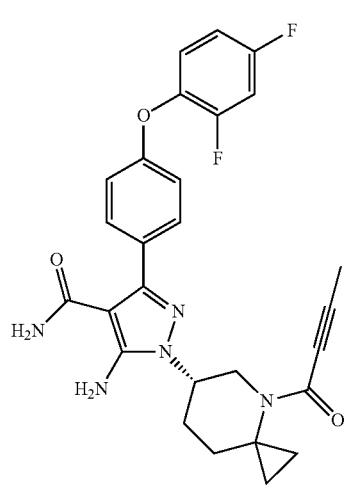
-continued
WS-423
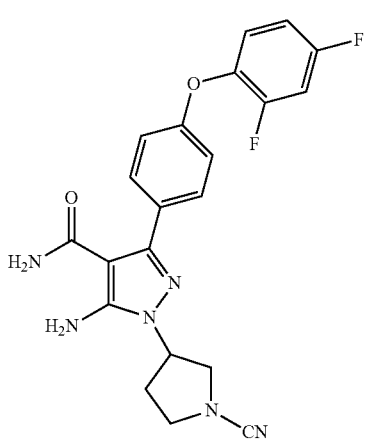
WS-424
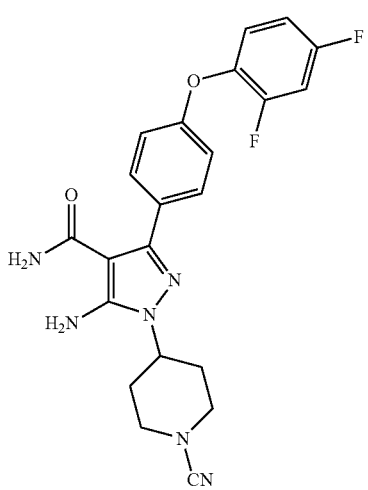
WS-425
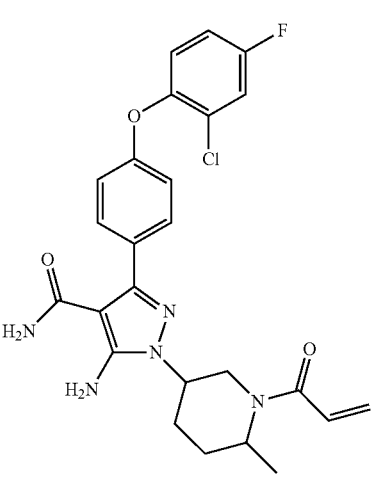

-continued
WS-426
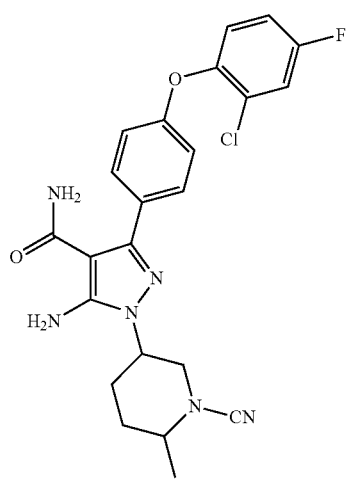
WS-427
WS-428
-continued
WS-429
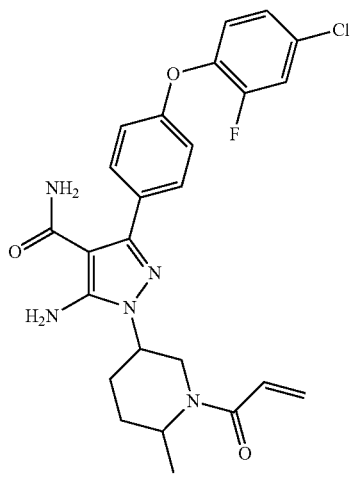
WS-430
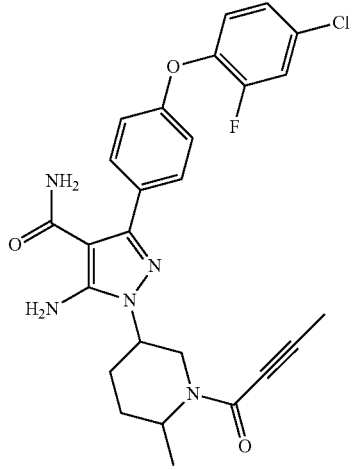
WS-431

WS-432
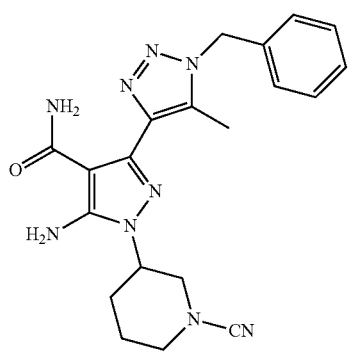
WS-433
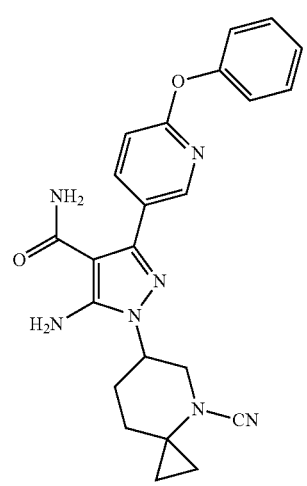
WS-434
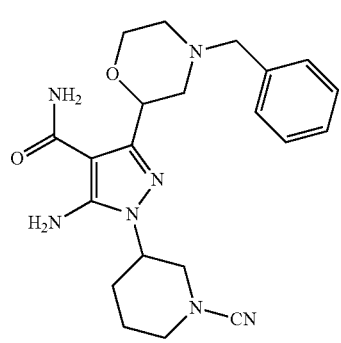
WS-435
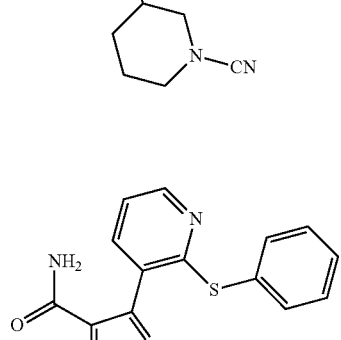
WS-436
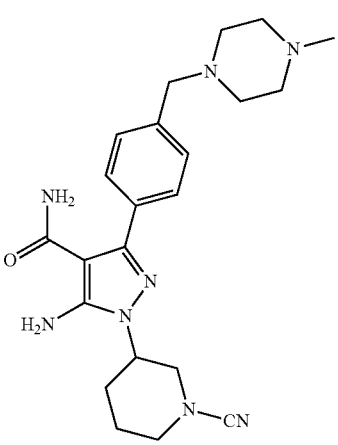
WS-437
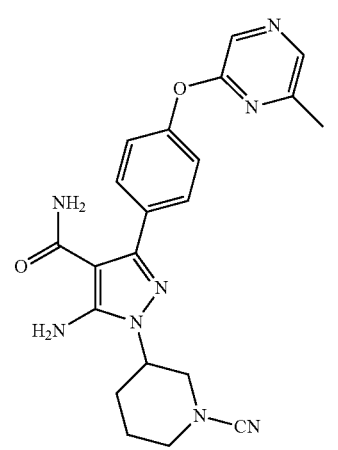
WS-438
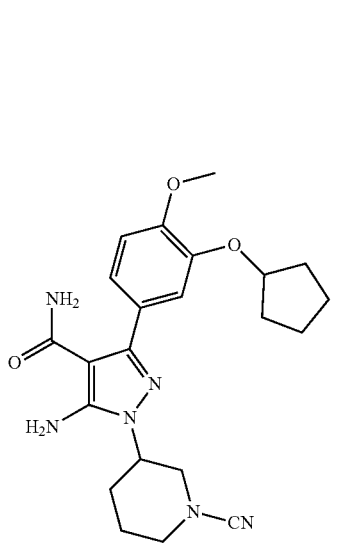

WS-439

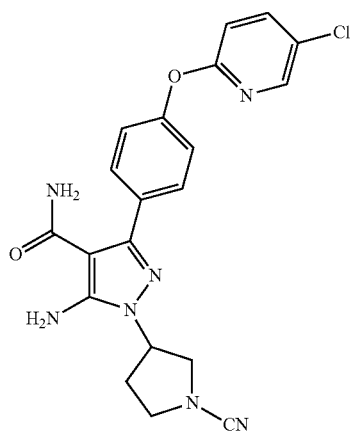

WS-440

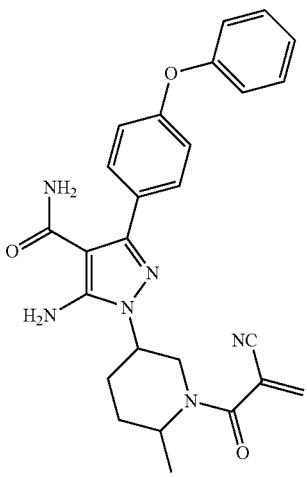

WS-441

WS-442

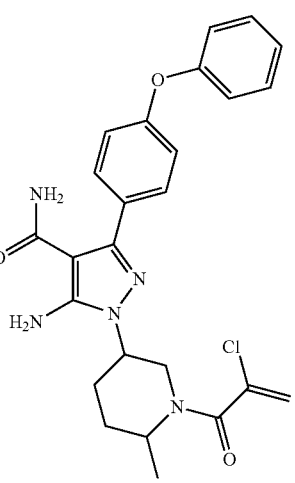

WS-443 and

WS-444

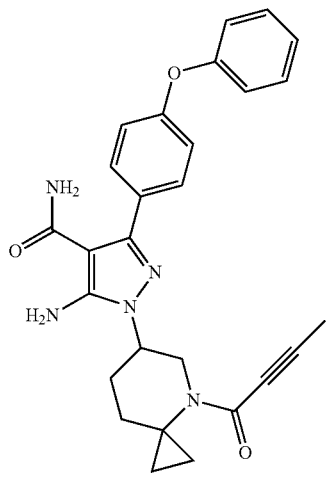

In an embodiment of the present invention, the term "pharmaceutically acceptable salt" refers to a pharmaceutically acceptable acid addition salt or a pharmaceutically acceptable base addition salt.

The term "pharmaceutically acceptable acid addition salt" refers to a salt formed with an inorganic or organic acid which can retain the biological efficacy of the free base without other side effects. Inorganic acid salts include, but are not limited to, hydrochloride, hydrobromide, sulfate, phosphate, and the like; and organic acid salts include, but are not limited to, formate, acetate, propionate, glycolate, gluconate, lactate, oxalate, maleate, succinate, fumarate, tartrate, citrate, glutamate, aspartate, benzoate, methanesulfonate, p-toluenesulfonate and salicylate, etc. These salts can be prepared by a method known in the art.

The term "pharmaceutically acceptable base addition salt" refers to a salt capable of maintaining the biological efficacy of the free acid without other side effects. These salts are prepared by adding an inorganic or organic base to the free acid. Salts derived from inorganic bases include, but are not limited to, sodium, potassium, calcium and magnesium salts and the like. Salts derived from organic bases include, but are not limited to, ammonium salt, triethylamine salt, lysine salt, arginine salt, and the like. These salts can be prepared by a method known in the art.

In an embodiment of the invention, the term "solvate" refers to a complex formed by a compound of the present invention with a solvent. They are obtained either by reacting in a solvent or by precipitating or crystallizing from a solvent. For example, a complex formed with water is referred to as a "hydrate."

In an embodiment of the present invention, the compounds of the invention may comprise one or more chiral centers and may be in different optically active forms. When comprising one chiral center, the compound comprises its enantiomers. The present invention encompasses these two isomers and a mixture of them, such as a racemic mixture. Enantiomers can be resolved by a method known in the art, such as crystallization and chiral chromatography, etc. When the compound of formula (I) comprises more than one chiral centers, there may be diastereomers. The embodiments of the present invention encompass any specific resolved optically pure isomers as well as a mixture of diastereomers. Diastereomers can be resolved by a method known in the art, such as crystallization and preparative chromatography.

In an embodiment of the present invention, the prodrug means that a parent compound can be obtained by hydrolyzing a known amino protecting group or a carboxy protecting group under physiological conditions or by releasing via an enzymatic reaction. Specific prodrug preparation methods may refer to Saulnier, M G; Frennesson, D B; Deshpande, M S; Hansel, S. B and Vysa, D M Bioorg. Med. Chem Lett. 1994, 4, 1985-1990. Greenwald, R B; Choc, Y H; Conover, C D; Shum, K.; Wu, D.; Royzen, M. J Med. Chem. 2000, 43, 475.

In a second aspect, the present invention provides a process for the preparation of the 5-aminopyrazole carboxamide compound represented by the above formula (I), comprising the steps of:

(1) Reaction of the compound of formula (V) with the compound of formula (VI) to provide the compound of formula (VII);

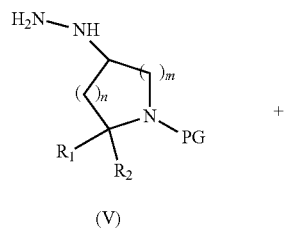

(V)

+

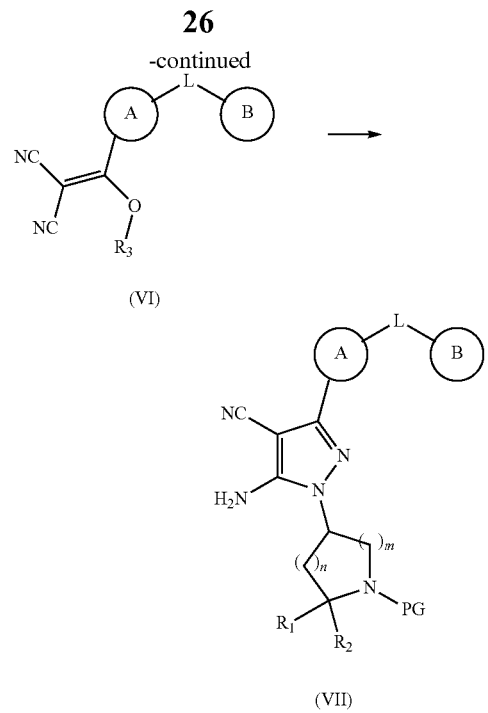

(VI)

(VII)

Hydrolysis of the compound of formula (VII) to give the compound of formula (VIII);

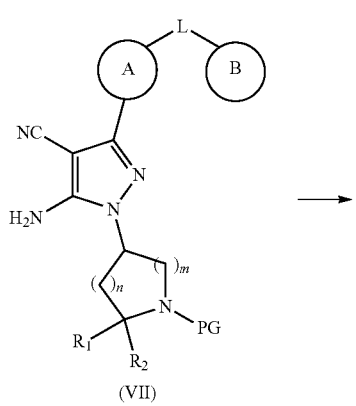

(VII)

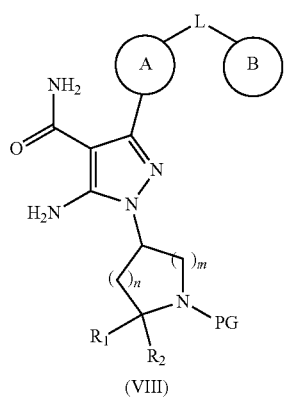

(VIII)

(3) Removal of the protection group PG from the compound of formula (VIII) to provide the compound of formula (IX);

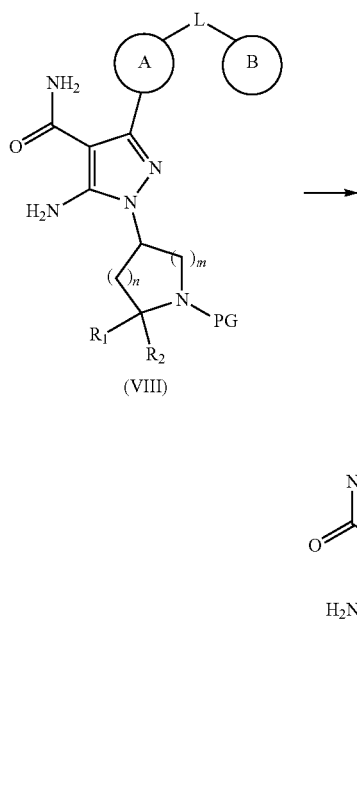

(VIII)

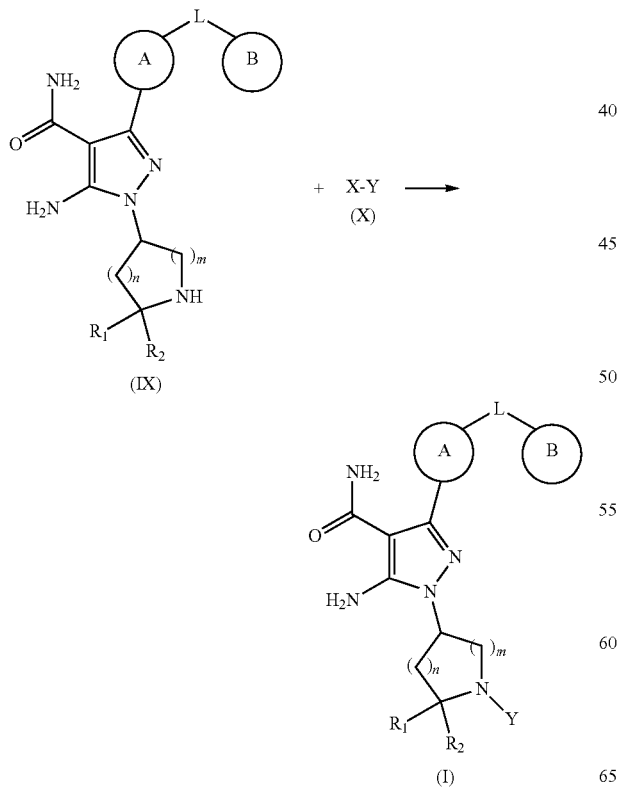

(IX)

(4) Reaction of the compound of formula (IX) with the compound of formula (X) to provide a compound of formula (I);

(IX) + X—Y (X) →

(I)

The substituents $R_1$, $R_2$, L, A, B, Y, and n and m in the above formula (V), formula (VI), formula (VII), formula (VIII), formula (IX) and formula (X) are defined as for above formula (I), PG is an amino protecting group (Suitable amino protecting groups include acyl (e.g. acetyl), carbamates (e g, 2',2',2'-trichloroethoxycarbonyl, Cbz (benzyloxycarbonyl) or BOC (tert-butoxycarbonyl)) and arylalkyl (e.g, Bn (benzyl)), which may be removed by hydrolysis (for example, using an acid such as a solution of hydrogen chloride in dioxane or a solution of trifluoroacetic acid in dichloromethane) or reduction (for example, hydrogenolysis of benzyl or benzyloxycarbonyl or reductive elimiation of 2',2',2'-trichloroethoxycarbonyl using zinc reductivity in acetic acid). Other suitable amino protecting groups include trifluoroacetyl (—COCF$_3$) (which can be removed by alkaline catalyzed hydrolysis), benzyloxycarbonyl or tert-butoxycarbonyl group, one may refer to T. W. Greene 'Protective Groups in Organic Synthesis' (4th edition, J. Wiley and. Sons, 2006)), $R_3$ is a $C_1$-$C_4$ alkyl group (preferably ethyl), and X is chloro, bromo or hydroxyl.

In an embodiment of the present invention, the present invention provides a process for producing 5-aminopyrazole carboxamide compound represented by the above formula (I), wherein the compound of the formula (VI) can be obtained as below:

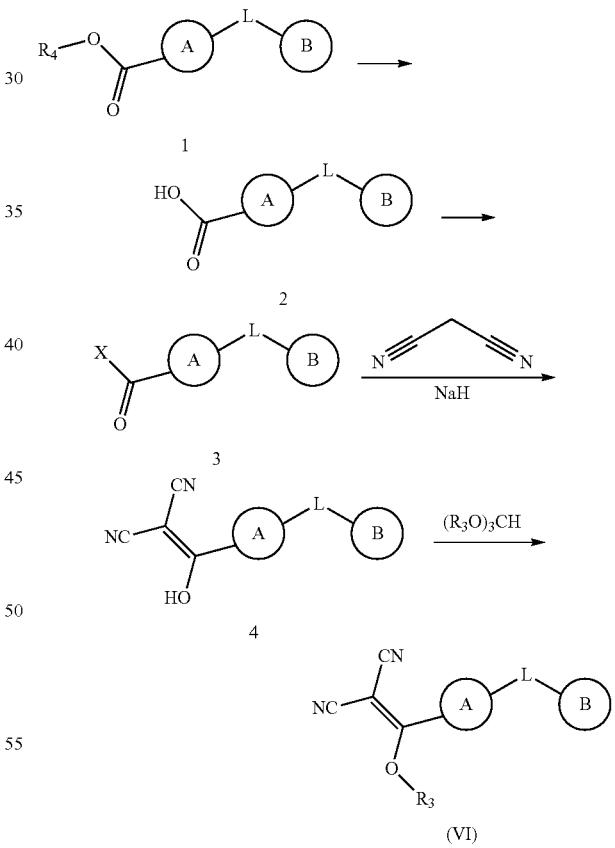

wherein the substituent $R_4$ in the above compound is $C_1$-$C_4$ alkyl (preferably methyl); X is chloro or bromo, preferably chloro; and $R_3$ is $C_1$-$C_4$ alkyl (preferably ethyl); L, A and B are as defined as those for the compound of formula (I).

More specifically, the following synthetic route can be followed:

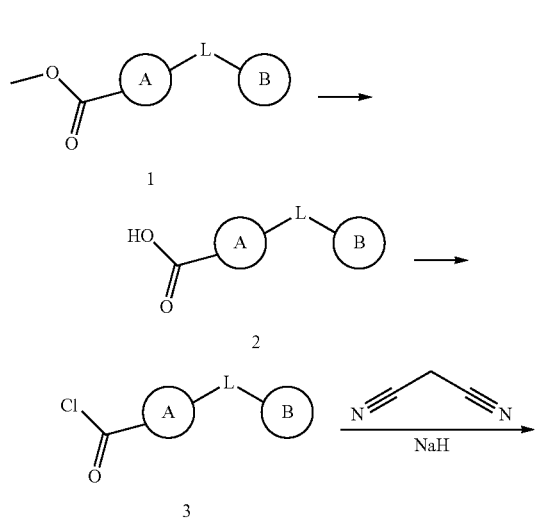
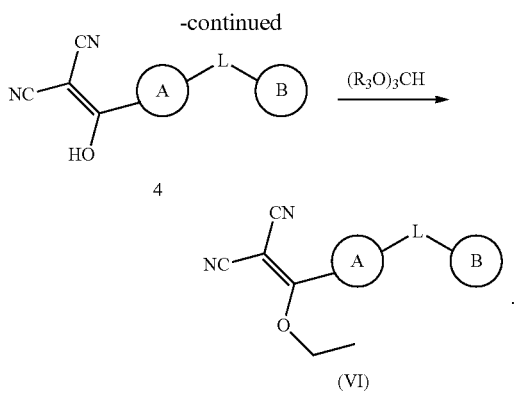
In an embodiment of the present invention, the present invention provides a process for the preparation of the 5-aminopyrazole carboxamide compound represented by the above formula (I), wherein the compound of the formula (V) can be produced by referring to the following method:
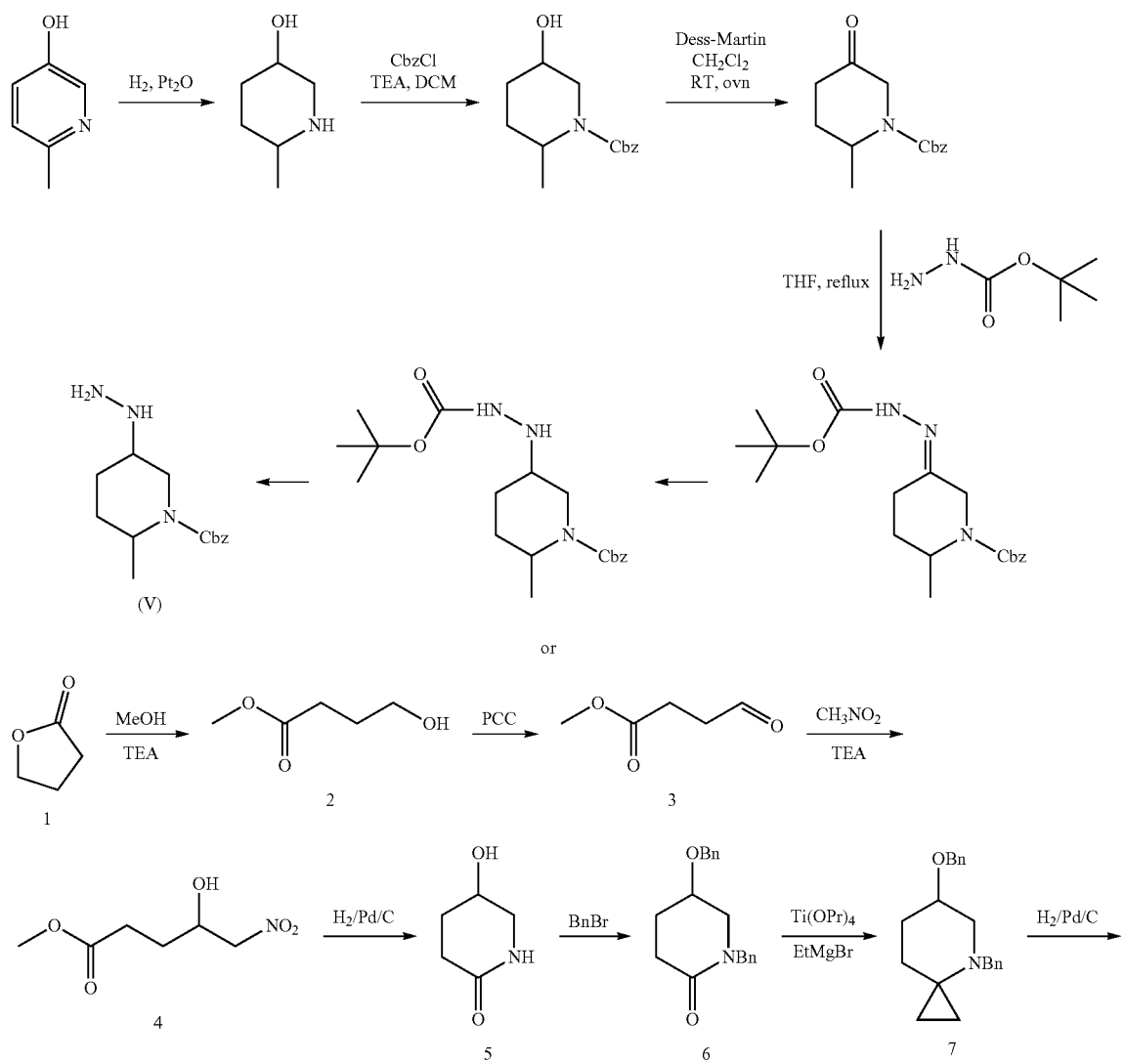

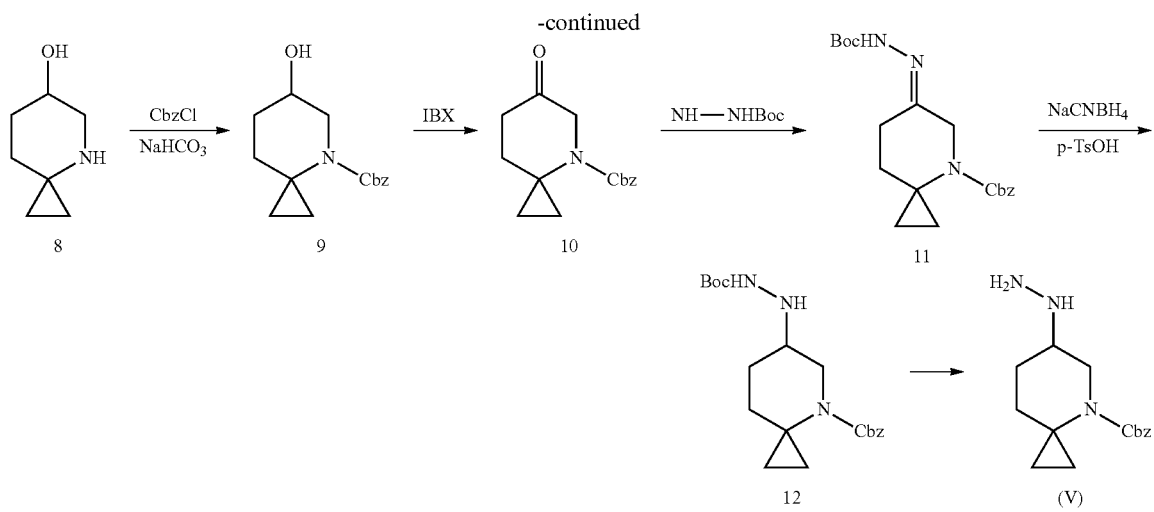

In an embodiment of the present invention, the present invention also provides an intermediate compound for the synthesis of the above 5-aminopyrazole carboxamide compound, including but not limited to:

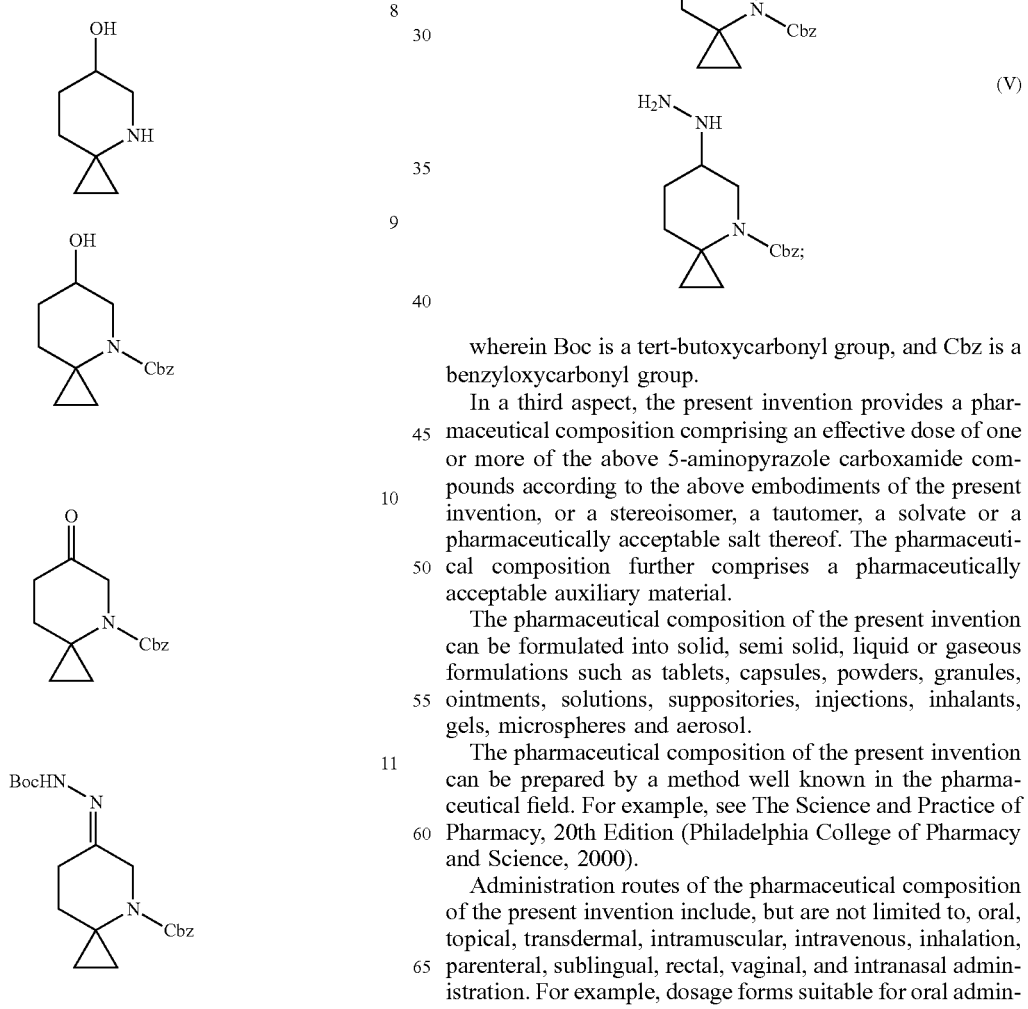

wherein Boc is a tert-butoxycarbonyl group, and Cbz is a benzyloxycarbonyl group.

In a third aspect, the present invention provides a pharmaceutical composition comprising an effective dose of one or more of the above 5-aminopyrazole carboxamide compounds according to the above embodiments of the present invention, or a stereoisomer, a tautomer, a solvate or a pharmaceutically acceptable salt thereof. The pharmaceutical composition further comprises a pharmaceutically acceptable auxiliary material.

The pharmaceutical composition of the present invention can be formulated into solid, semi solid, liquid or gaseous formulations such as tablets, capsules, powders, granules, ointments, solutions, suppositories, injections, inhalants, gels, microspheres and aerosol.

The pharmaceutical composition of the present invention can be prepared by a method well known in the pharmaceutical field. For example, see The Science and Practice of Pharmacy, 20th Edition (Philadelphia College of Pharmacy and Science, 2000).

Administration routes of the pharmaceutical composition of the present invention include, but are not limited to, oral, topical, transdermal, intramuscular, intravenous, inhalation, parenteral, sublingual, rectal, vaginal, and intranasal administration. For example, dosage forms suitable for oral administration include capsules, tablets, granules, and syrups, etc.

The compound of the formula (I) of the present invention contained in these preparations may be solid powders or granules; a solution or suspension in an aqueous or non-aqueous liquid; a water-in-oil or oil-in-water emulsion or the like. The above dosage forms can be prepared from an active compound and one or more carriers or excipients via a conventional pharmaceutical method. The carriers need to be compatible with the active compound or other auxiliary materials. For solid formulations, common non-toxic carriers include, but are not limited to, mannitol, lactose, starch, magnesium stearate, cellulose, glucose, sucrose, and the like. Carriers for liquid preparations include, but are not limited to, water, physiological saline, aqueous dextrose, ethylene glycol, polyethylene glycol, and the like. The active compound can form a solution or suspension with the above carriers. The specific mode of administration and dosage form depend on the physico-chemical properties of the compound per se, as well as the severity of the disease being treated, etc. Those skilled in the art can determine a specific administration route based on the above factors in combination with their own knowledge. For example, see: Li Jun, "Clinical Pharmacology", People's Health Publishing House, 2008.06; Ding Yufeng, Disscussion on clinical dosage form factors and drug rational use in hospital, Herald of Medicine, 26 (5), 2007; Howard C. Ansel, Loyd V. Allen, Jr., Nicholas G Popovich (Eds.), Jiang Zhiqiang (Trans.), "Pharmaceutical Dosage Forms and Drug Delivery Systems", China Medical Science Press, 2003.05.

The pharmaceutical composition in the embodiments of the present invention may be presented in unit dosage forms containing a predetermined amount of active ingredient per unit dosage. Preferred unit dosage compositions are those containing a daily dose or a sub-dose, or an appropriate fraction thereof, of the active ingredient. Thus, such unit doses can be administered more than once in a day. Preferred unit dosage compositions are those containing a daily dose or a sub-dose (more than one administrations in a day), or an appropriate fraction thereof, as described herein above.

The pharmaceutical composition according to the embodiments of the present invention are formulated, quantified, and administered in a manner in accordance with medical practice guideline. A "therapeutically effective amount" of the compound according to the embodiments of the present is determined by the particular condition to be treated, the individual being treated, the cause of the condition, the target of the drug, and the manner of administration, etc. Generally, the dose for parenteral administration may be 1-200 mg/kg, and the dose for oral administration may be 1-1000 mg/kg.

The range of effective dosages provided herein is not intended to limit the scope of the present invention, but rather to represent a preferred dosage range. However, the most preferred dosage can be adjusted for individual subjects, as is appreciated and determinable by those skilled in the art (see, e.g., Berkow, et al., The Merck Manuals, 16th ed., Merck, Rahway, N.J., 1992).

In a fourth aspect, the present invention provides use of the above 5-aminopyrazole carboxamide compound or a stereoisomer, tautomer, solvate or pharmaceutically acceptable salt thereof in the manufacture of a medicament for preventing or treating BTK mediated diseases.

The present invention provides a method for inhibiting BTK activity, comprising administration of the above 5-aminopyrazole carboxamide compound of the present invention or a stereoisomer, a tautomer, a solvate or a pharmaceutically acceptable salt thereof, or a pharmaceutical composition comprising the above 5-aminopyrazole carboxamide compound of the present invention or a stereoisomer, a tautomer, a solvate or a pharmaceutically acceptable salt thereof, to a biological system.

In some embodiments, the biological system is an enzyme, a cell, or a mammal.

The present invention also provides a method for preventing or treating a disease mediated by BTK, comprising administration of a therapeutically effective amount of one or more of the above 5-aminopyrazole carboxamide compounds of the present invention or a stereoisomer, a tautomer, a solvate or a pharmaceutically acceptable salt thereof and one or more drugs selected from the group consisting of immunomodulators, immunological checkpoint inhibitors, glucocorticoids, non-steroid anti-inflammatory drugs, Cox-2 specific inhibitors, TNF-α binding proteins, interferons, interleukins and chemotherapeutic drugs to a patient in need thereof.

In an embodiment of the present invention, the BTK mediated diseases include autoimmune diseases, inflammatory diseases, xenogeneic immune conditions or diseases, thromboembolic diseases, and cancers. In some specific embodiments, the cancers comprise B-cell chronic lymphocytic leukemia, acute lymphocytic leukemia, non-Hodgkin's lymphoma, Hodgkin's lymphoma, acute myeloid leukemia, diffuse large B-cell lymphoma, multiple myeloma, mantle cell lymphoma, small lymphocytic lymphoma, Waldenstrom's macroglobulinemia, or a solid tumor. In some specific embodiments, the autoimmune diseases and inflammatory diseases are selected from the group consisting of rheumatoid arthritis, osteoarthritis, juvenile arthritis, chronic obstructive pulmonary disease, multiple sclerosis, systemic lupus erythematosus, psoriasis, psoriatic arthritis, Crohn's disease, ulcerative colitis, and irritable bowel syndrome. In some specific embodiments, the xenogeneic immune conditions or diseases comprise graft versus host disease, transplantation, blood transfusion, allergic reaction, allergy, type I hypersensitivity, allergic conjunctivitis, allergic rhinitis or atopy dermatitis.

Experimental data herein demonstrate that the above 5-aminopyrazolyl carboxamide compound provided by the present invention is an effective and safe inhibitor of protein kinase BTK.

BRIEF DESCRIPTION OF THE DRAWINGS

The accompanying drawings are provided for further illustrating the examples of the invention and constitute a part of the specification. The following specification of the embodiments of the invention with reference to the figures and detailed description of the invention does not limit the embodiments of the invention.

FIG. 1 shows that the compounds of the present invention significantly inhibit the growth of the diffuse large B-cell lymphoma cell line TMD-8 in vivo and exhibit the same antitumor effects as the control compound ibrutinib.

DETAILED DESCRIPTION OF THE INVENTION

The embodiments of the present invention are described in detail below. It should be understood that the specific examples of the experiments, the synthetic methods, and the intermediates involved therein as described below are illustrative of the present application and are not intended to limit the scope of the application. It should be noted that, in the case of no conflict, the examples and the features therein of the present application may be arbitrarily combined with each other.

The starting materials used in the experiments of the present invention are either purchased from a reagent supplier or prepared from known raw materials by a method well known in the art. Unless otherwise indicated, the following conditions are applied to the examples herein.

The temperature unit is Celsius (° C.); and room temperature s defined as 18-25° C.;

An organic solvent is dried over anhydrous magnesium sulfate or anhydrous sodium sulfate; and is rotary dried under a reduced pressure and an increased temperature using a rotary evaporator (for example: 15 mmHg, 30° C.);

200-300 mesh silica gel is used as a carrier for flash column chromatography, and TLC represents thin layer chromatography;

Normally, the progress of a reaction is monitored by TLC or LC-MS;

The identification of a final product is conducted by nuclear magnetic resonance (Bruker AVANCE 300, 300 MHz) and LC-MS (Bruker esquire 6000, Agilent 1200 series).

Example 1

Preparation of 5-amino-3-(4-((5-chloropyridin-2-yl)oxy)phenyl-1-(1-cyano-6-methylpiperidin-3-yl)-1H-pyrazole-4-carboxamide (WS-400)

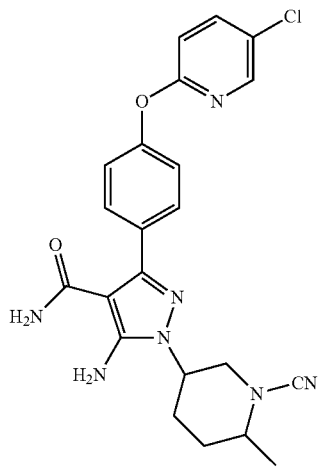 [SMILES: CC1CCC(n2nc(-c3ccc(Oc4ccc(Cl)cn4)cc3)c(C(N)=O)c2N)CN1C#N]

Step 1. Preparation of 6-methylpiperidin-3-ol

5-Hydroxy-2-methylpyridine (1 g, 9 mmol) was dissolved in acetic acid (20 mL) and then platinum dioxide (0.25 g) was added. The reaction mixture was shaken in a hydrogen atmosphere under a pressure of 50 psi overnight. The solution was filtered and rotary dried to give the crude product 6-methylpiperidin-3-ol.

Step 2. Preparation of Benzyl 5-hydroxy-2-methylpiperidine-1-carboxylate

6-Methylpiperidin-3-ol was dissolved in dichloromethane (100 mL) and then triethylamine (7.5 eq) was added dropwise followed by benzyloxycarbonyl chloride (2 g, 11.2 mmol). The reaction was completed after stirring for 16 hours. After the reaction solution was rotary dried, the residue was purified using a silica column to yield the desired product benzyl 5-hydroxyl-2-methylpiperidine-1-carboxylate (colorless oil, 60%).

Step 3. Preparation of Benzyl 2-methyl-5-oxopiperidine-1-carboxylate

Benzyl 5-hydroxy-2-methylpiperidine-1-carboxylate (1 g, 3.96 mmol) was dissolved in dichloromethane (10 mL) and cooled to 0□, and Dess-Martin reagent (1 eq) was added. The reaction was stirred at 0□ for 1 hour and then at room temperature for 5 hours. The reaction was carefully quenched with saturated aqueous sodium thiosulfate solution and then diluted with water and dichloromethane. The organic layer was retained, washed with saturated brine and dried over anhydrous sodium sulfate. After the organic layer was concentrated, the resulting crude product benzyl 2-methyl-5-oxopipyridin-1-carboxylate was directly used in the next step without further purification.

Step 4, Preparation of Benzyl (5E)-5-[(tert-butoxycarbonyl)hydrazono]-2-methylpiperidine-1-carboxylate Benzyl 2-methyl-5-oxopiperidine-1-carboxylate (2.00 g, 8.09 mmol) was dissolved in tetrahydrofuran (10 mL), then t-butoxycarbonyl hydrazine (1.2 eq) was added at room temperature. The reaction was refluxed for 2.5 hours. The solvent was then evaporated to give the crude product benzyl (5E)-5-[(tert-butoxycarbonyl)hydrazonol]-2-methylpiperidine-1-carboxylate as a white solid.

Step 5. Preparation of Benzyl 5-[2-(tert-butoxycarbonyl)hydrazino]-2-methylpiperidine-1-carboxylate Benzyl (5E)-5-[(tert-butoxycarbonyl)hydrazono]-2-methylpiperidine-1-carboxylate (1.2 g, 4 mmol) was dissolved in tetrahydrofuran (10 mL), then sodium cyanoborohydride (1 eq) was added at room temperature followed by a solution of p-toluenesulfonic acid monohydrate (1 eq) in tetrahydrofuran (2 mL) dropwise. The reaction solution was stirred at room temperature for 20 hours. After the reaction solution was concentrated under a reduced pressure, ethyl acetate (100 mL) was added, which was washed sequentially with a saturated aqueous sodium bicarbonate solution, 1N aqueous sodium hydroxide solution, water and saturated brine, and then diced over anhydrous sodium sulfate. After concentration of the solution, the crude product benzyl 5-[2-(tert-butyloxycarbonyl)hydrazino]-2-methylpiperidine-1-carboxylate was obtained as a white solid.

Step 6. Preparation of Benzyl 5-hydrazino-2-methylpiperidine-1-carboxylate

Benzyl 5-[2-(tert-butyloxycarbonyl)hydrazino]-2-methylpiperidine-1-carboxylate (1.78 g, 4.9 mmol) was dissolved in dichloromethane (10 mL), then trifluoroacetic acid (5 mL) was added dropwise at room temperature. The reaction solution was stirred at room temperature for 5 hours. The reaction solution was concentrated to yield pale yellow crude product benzyl 5-hydrazino-2-methylpiperidine-1-carboxylate.

Step 7. Preparation of Methyl 4-((5-chloropyridin-2-yl)oxy)benzoate

Methyl 4-hydroxybenzoate (6.5 g, 49 mmol), 5-chloro-2-fluoropyridine (5.0 g, 33 mmol) and cesium carbonate (20 g, 65 mmol) were dissolved in N,N-dimethyl foramide (50 mL). The reaction solution was refluxed at 110° C. for 12 hours, and the completion of reaction was monitored by thin layer chromatography (petroleum ether:ethyl acetate=5:1), the solvent was rotary dried. The crude compound was partitioned between ethyl acetate (250 mL) and water (250 mL). The organic phase was dried over anhydrous sodium sulfate, filtered and evaporated under a reduced pressure. The crude compound was purified and separated by column chromatography to yield the product methyl 4-((5-chloropyridin-2-yl)oxy)benzoate (9.0 g, 93%).

MS: m/z 264.2 [M+1]

Step 8. Preparation of 4-((5-chloropyridin-2-yl)oxy)benzoic Acid

Methyl 4-((5-chloropyridin-2-yl)oxy)benzoate (6.5 g, 49 mmol) was dissolved in methanol (100 mL) and water (5 mL). To the reaction system was added lithium hydroxide (2.3 g). The reaction solution was reacted at 45° C. for 12 hours, and thin layer chromatography (petroleum ether:ethyl acetate=1:1) was used to monitor the completion of reaction, the solvent was rotary dried. The crude compound was added to diluted hydrochloric acid (100 mL, 1 M) to adjust pH to 7. At this time, a substantial amount of solids were generated, and the solids were filtered and oven-dried to yield the product 4-((5-chloropyridin-2-yl)oxy)benzoic acid (6.5 g, as a white solid, 84%).

MS: m/z 250.1 [M+1]

Step 9. Preparation of 4-((5-chloropyridin-2-yl)oxy)benzoyl Chloride 4-((5-Chloropyridin-2-yl)oxy)benzoic acid (6.5 g, 23 mmol) was added to thionyl chloride (20 mL). The reaction solution was reacted at 80° C. for 3 hours and thin layer chromatography (petroleum ether:ethyl acetate=3:1) was used to monitor the completion of reaction, the solvent was rotary dried. The crude product 4-((5-chloropyridin-2-yl)oxy)benzoyl chloride (7 g, as a yellow solid) was used directly in the next step.

Step 10. Preparation of 2-((4-((5-chloropyridin-2-yl)oxy)phenyl)(hydroxy)methylene)malononitrile At a condition of 0° C., malononitrile (3.72 g, 56.4 mmol) was dissolved in anhydrous tetrahydrofuran (50 mL), and then sodium hydride (3.6 g, 90 mmol, 60%) was slowly added. After the addition was completed, the reaction was warmed to room temperature while stirring for 1 hour and then cooled to 0° C. 4-((5-chloropyridin-2-yl)oxy)benzoyl chloride (6 g, 22.2 mmol) was dissolved in anhydrous tetrahydrofuran (50 mL), and the above reaction solution was slowly added dropwise. After completion of the dropping process, the reaction solution was stirred at 0° C. for 1 hour. Thin layer chromatography (petroleum ether:ethyl acetate=3:1) was used to monitor the completion of reaction, a new spot was generated. The reaction solution was quenched with saturated ammonium chloride (100 mL) and extracted with EtOAc three times (100 mL×3). The organic phase was washed with saturated brine (100 mL), dried over anhydrous sodium sulfate, and rotary dried. The crude compound was mashed with petroleum ether:ethyl acetate=50:1 to yield 2-((4-((5-chloropyridin-2-yl)oxy)phenyl)(hydroxy)methylene)malononitrile (8.0 g, as a pale yellow solid, 82%).

MS: m/z 298 [M+1]

Step 11. Preparation of 2-((4-((5-chloropyridin-2-yl)oxy)phenyl)(ethoxy)methylene)malononitrile 2-((4-((5-chloropyridin-2-yl)oxy)phenyl)(hydroxy)methylene) malononitrile (5.0 g, 16.8 mmol) was added to triethyl orthoformate (50 mL), the reaction was warmed to 80° C. while stirring for 12 hours. Thin layer chromatography (petroleum ether:ethyl acetate=3:1) indicated the generation of product. The reaction solution was filtered, and the filtrate was rptary dried to give a solid which was mashed with methanol to yield 2-((4-((5-chloropyridin-2-yl)oxy)phenyl)(ethoxy)methylene)malononitrile (1.5 g, as a white product, 27.7%).

MS: m/z 326.0 [M+1]

Step 12. Preparation of Benzyl 5-(5-amino-3-(4-((5-chloropyridin-2-yl)oxy)phenyl)-4-cyano-1H-pyrazol 1-yl)-2-methylpiperidine-1-carboxylate 2-((4-((5-chloropyridin-2-yl)oxy)phenyl)(ethoxy)methylene)malononitrile (1.0 g, 3.09 mmol), benzyl 5-hydrazino-2-methylpiperidine-1-carboxylate (1.28 g, 3.71 mmol) and triethylamine (1.56 g. 15.5 mmol) were dissolved in ethanol (20 mL). The reaction solution was reacted at 25 CC for 12 hours, and the completion of reaction was monitored by thin layer chromatography (petroleum ether:ethyl acetate=2:1), the reaction was quenched with water and extracted with ethyl acetate (25 mL*3). The organic phase was dried over anhydrous sodium sulfate, filtered and rotary dried. The crude compound was mashed twice with petroleum ether:ethyl acetate=50:1 to give the product benzyl 5-(5-amino-3-(4-((5-chloropyridin-2-yl)oxy)phenyl)-4-cyano-1H-pyrazol-1-yl)-2-methylpiperidine-1-carboxylate (1.5 g, 88%).

MS: m/z 555.2 [M+1]

Step 13. Preparation of 5-amino-3-(4-((5-chloropyridin-2-yl)oxy)phenyl)-1-(6-methylpiperidin-3-yl)-1H-pyrazole-4-carboxamide Benzyl 5-(5-amino-3-(4-((5-chloropyridin-2-yl)oxy)phenyl)-4-cyano-1H-pyrazol-1-yl)-2-methylpiperidine-1-carboxylate (750 mg, 1.35 mmol) was added to 90% concentrated sulfuric acid (over 10 min) at room temperature, stirred for 15 minutes, and then the reaction was warmed to 30° C. for 24 hours. Thin layer chromatography (dichloromethane:methanol=10:1) was used for detecting that the reaction was completed, and the reaction solution was slowly poured into aqueous ammonia (50 ml), adjusted to pH=7, and extracted with ethyl acetate three times (30 mL*3). The combined organic phase was washed with saturated brine (30 mL), dried over anhydrous sodium sulfate, and rotary dried. The crude compound was purified on a column to give 5-amino-3-(4-((5-chloropyridin-2-yl)oxy)phenyl)-1-(6-methylpiperidin-3-yl)-1H-pyrazole-4-carboxamide (480 mg, 78%, as a pale yellow solid).

MS: m/z 439.2 [M+1]

Step 14. Preparation of 5-amino-3-(4-((5-chloropyridin-2-yl)oxy)phenyl)-1-((3R,6S)-1-cyano-6-methylpiperidin-3-yl)-1H-pyrazole-4-carboxamide 5-amino-3-(4-((5-chloropyridin-2-yl)oxy)phenyl)-1-(6-methylpiperidin-3-yl)-1H-pyrazole-4-carboxamide (50 mg, 0.113 mmol) was dissolved in N,N-dimethylformamide (5 mL), then cesium carbonate (110 mg, 0.342 mmol) and cyanogen bromide (12.5 mg, 0.113 mmol) were added. The reaction solution was stirred at room temperature for 2 hours. Thin layer chromotography is conducted to detect the completion of reaction. The reaction mixture was poured into ethyl acetate (50 mL), washed with water (20 mL*3), dried over anhydrous sodium sulfate, filtered and evaporated to dryness under a reduced pressure. The crude product was purified by a preparative plate (dichloromethane:methanol=50:1) to give the product 5-amino-3-(4-((5-chloropyridin-2-yl)oxy)phenyl)-1-(1-cyano-6-methylpiperidin-3-yl)-1H-pyrazole-4-carboxamide (15 mg, 15%).

MS: m/z 452.2 [M+1]

Example 2

Preparation of 5-amino-3-(4-((5-chloropyridin-2-yl)oxy)phenyl)-1-((3R,6S)-1-cyano-6-methylpiperidin-3-yl)-1H-pyrazole-4-carboxamide (WS-401)

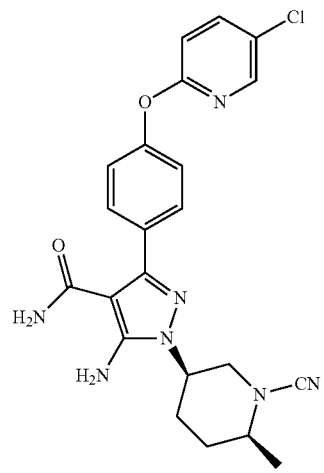 [SMILES: C[C@H]1CC[C@@H](n2nc(-c3ccc(Oc4ccc(Cl)cn4)cc3)c(C(N)=O)c2N)CN1C#N]

The compound of Example 2 can be obtained from chiral resolution of the product from step 14 in Example 1. The resolution conditions were: Supercritical fluid chromatography (ChiralPak AD 5μ, 21×250 mm col, 27% metanol, 70 mL/min). MS: m/z 452.2 [M+1]

Example 3

Preparation of 5-amino-3-(4-((5-chloropyridin-2-yl)oxy)phenyl)-1-((3S,6R)-1-cyano-6-methylpiperidin-3-yl)-1H-pyrazole-4-carboxamide (WS-402)

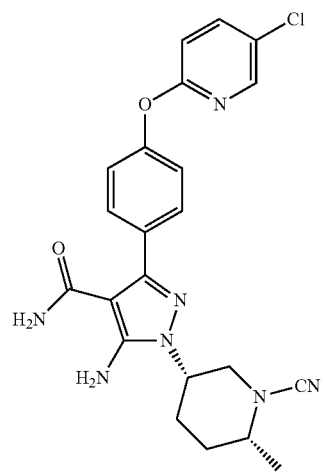 [SMILES: C[C@@H]1CC[C@H](n2nc(-c3ccc(Oc4ccc(Cl)cn4)cc3)c(C(N)=O)c2N)CN1C#N]

The compound of Example 3 can be obtained from chiral resolution of the product from step 14 in Example 1. The resolution conditions were: Supercritical fluid chromatography (ChiralPak AD 5μ, 21×250 mmol, 27% methanol, 70 mL/min). MS: m/z 452.2 [M+1]

Example 4

Preparation of 5-amino-3-(4-((5-chloropyridin-2-yl)oxy)phenyl)-1-((3R,6R)-1-cyano-6-methylpiperidin-3-yl)-1H-pyrazole-4-carboxamide (WS-403)

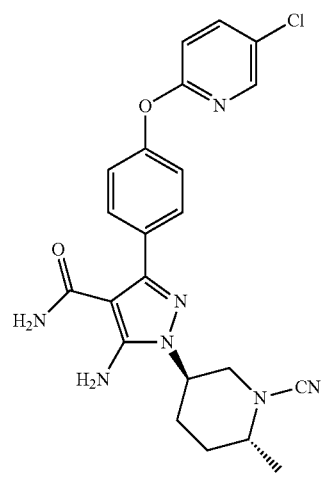 [SMILES: C[C@@H]1CC[C@@H](n2nc(-c3ccc(Oc4ccc(Cl)cn4)cc3)c(C(N)=O)c2N)CN1C#N]

The compound of Example 4 can be obtained from chiral resolution of the product from step 14 in Example 1. The resolution conditions were: Supercritical fluid chromatography (ChiralPak AD 5μ, 21×250 mm col, 27% methanol, 70 mL/min). MS: m/z 452.2 [M+1]

Example 5

Preparation of 5-amino-3-(4-((5-chloropyridin-2-yl)oxy)phenyl)-1-((3S,6S)-1-cyano-6-methylpiperidin-3-yl)-1H-pyrazole-4-carboxamide (WS-404)

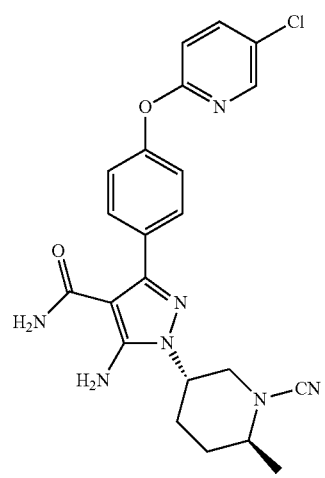 [SMILES: C[C@H]1CC[C@H](n2nc(-c3ccc(Oc4ccc(Cl)cn4)cc3)c(C(N)=O)c2N)CN1C#N]

The compound of Example 5 can be obtained from chiral resolution of the product from step 14 in Example 1. The resolution conditions were: Supercritical fluid chromatography (ChiralPak AD 5µ, 21×250 mm col, 27% methanol, 70 mL/min). MS: m/z 452.2 [M+1]

Example 6

Preparation of 5-amino-3-(4-((5-chloropyridin-2-yl)oxy)phenyl)-1-(4-cyano-4-azaspiro[2.5]oct-6-yl)-1H-pyrazole-4-carboxamide (WS-405)

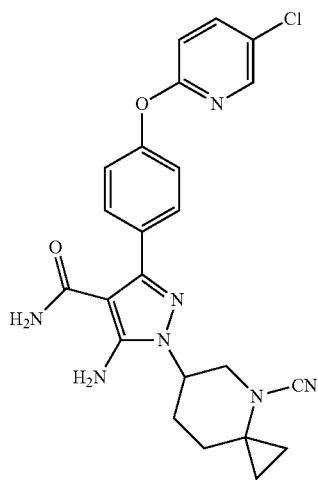 [SMILES: N#CN1CC(n2nc(-c3ccc(Oc4ccc(Cl)cn4)cc3)c(C(N)=O)c2N)CCC12CC2]

Step 1. Preparation of methyl 4-hydroxybutyrate

Dihydrofuran-2(3H)-one (100 g, 1.163 mol) and triethylamine (460 g, 4.65 mol) were added to a methanol solution (1 L), and the reaction was reacted at 60° C. for 24 hours. Thin layer chromatography (petroleum ether:ethyl acetate=2:1) was used to detect the completion of reaction, and the reaction solution was rotary dried to afford methyl 4-hydroxybutyrate (120 g, 87.6%, as a yellow liquid) which was directly used in the next step.

Step 2. Preparation of Methyl 4-oxobutyrate

Methyl 4-hydroxybutyrate (120 g, 1.02 mol) was added to a dichloromethane solution (1.2 L), then pyridinium chlorochromate (330 g, 1.53 mol) was added to the above reaction solution, and the reaction was carried out at room temperature for 12 hours. Thin layer chromatography (petroleum ether:ethyl acetate=3:1) was used to detect that the reaction was completed. The reaction solution was filtered through celite and rotary dried to give methyl 4-oxobutyrate (60 g, 50%, as a yellow liquid), which was used directly in the next step.

Step 3. Preparation of Methyl 4-hydroxy-5-nitrovalerate

In an ice water bath, methyl 4-oxobutyrate (60 g, 0.46 mol), nitromethane (42 g, 0.69 mol), tetrahydrofuran (300 mL), and tert-butanol (300 mL) were added to a reaction flask. Then potassium tert-butoxide (5 g) was slowly added to the above reaction system, the temperature was raised to room temperature, and the reaction was carried out for 2 hours. Thin layer chromatography (petroleum ether:ethyl acetate=3:1) was used to detect that the reaction was completed, and water (30 mL) was added to quench the reaction. The solvent was rotary dried. Water (300 mL) and ethyl acetate (300 mL) were added for liquid separation. The organic phase was washed with saturated brine, dried over anhydrous sodium sulfate, and rotary dried to give crude methyl 4-hydroxy-5-nitrovalerate (45 g, as a pale yellow oily liquid), which was used directly in the next step.

Step 4. Preparation of 5-hydroxypiperidin-2-one

Methyl 4-hydroxy-5-nitropentanoate (45 g, 0.23 mol) and palladium on carbon (2.1 g) were added to a methanol solution (500 mL), and the reaction solution was reacted at 60° C. under $H_2$ for 24 hours. Thin layer chromatography (petroleum ether:ethyl acetate=1:1) was used to detect the completion of reaction. The reaction solution was filtered through celite, and the filtrate was rotary dried to give 5-hydroxypiperidin-2-one (10 g, as a yellow solid, 38%), which was used directly in the next reaction.

Step 5. Preparation of 1-benzyl-5-(benzyloxy)piperidin-2-one 5-hydroxypiperidin-2-one (10 g, 0.1 mol) was added to dimethyl sulfoxide (100 mL) at room temperature, and then sodium hydride (10 g, 0.25 mol) was slowly added to the above reaction system. After the completion of addition, benzyl bromide (43.5 g, 0.25 mol) was added to the reaction solution, and stirred overnight. Thin layer chromatography (petroleum ether:ethyl acetate=1:1) was used to detect that the reaction was completed. To the reaction system was added saturated aq. ammonium chloride (100 mL) to quench the reaction. The reaction was extracted with EtOAc three times (100 mL*3), washed with saturated brine, dried over anhydrous sodium sulfate, rotary dried, and purified by column chromatography to yield 1-benzyl-5-(benzyloxy)piperidin-2-one (16 g, as a yellow solid, 54%).

Step 6. Preparation of 4-benzyl-6-(benzyloxy)-4-azaspiro[2.5]octane 1-benzyl-5-(benzyloxy)piperidin-2-one (15 g, 50 mmol) was dissolved in anhydrous tetrahydrofuran (150 mL) under protection of a nitrogen atmosphere at −78° C., then ethyl magnesium bromide (150 mL) was slowly added to the reaction flask dropwise. After the dropping process was completed, tetrapropyl titanate (45 g, 150 mmol) was added to the above reaction system. After the addition was completed, the reaction was warmed to room temperature and stirred for 2 hours. Thin layer chromatography (petroleum ether:ethyl acetate=10:1) was used to detect that the reaction was completed. The reaction was quenched by addition of saturated aq. ammonium chloride (100 ml) to the recstion system, extracted with ethyl acetate three times (100 mL*3), washed with saturated brine, dried over anhydrous sodium sulfate, rotary dried, and purified by column chromatography to yield 4-benzyl-6-(benzyloxy)-4-azaspiro[2.5]octane (5.1 g, as a yellow solid, 31%).

Step 7. Preparation of 4-azaspiro[2.5]oct-6-ol 4-benzyl-6-(benzyloxy)-4-azaspiro[2.5]octane (5.5 g, 18 mmol) and palladium on carbon (2 g, 1.8 mmol) were added to a solution of methanol (200 mL) and hydrogen chloride (2 mL). The reaction solution was reacted under $H_2$ at 60° C.

for 48 hours. Thin layer chromatography (petroleum ether: ethyl acetate=10:1) was used to detect that the reaction was completed. The reaction solution was filtered through celite, and the filtrate was rotary dried to yield 4-azaspiro[2.5]oct-6-ol (2.5 g, as a yellow solid), which was used directly in the next step.

Step 8. Preparation of Benzyl 6-hydroxy-4-azaspiro[2.5]octane-4-carboxylate

4-Azaspiro[2.5]oct-6-ol (2.5 g, 21 mmol) and sodium bicarbonate (3.8 g, 45 mmol) were added to a solution of tetrahydrofuran (100 mL), then benzyloxycarbonyl chloride (4.25 g, 25 mmol) was added dropwise to the above reaction system. The reaction solution was reacted at room temperature for 48 hours. Thin layer chromatography (petroleum ether:ethyl acetate=3:1) was used to detect that the reaction was completed. The reaction solution was extracted, and the filtrate was rotary dried and purified by column chromatography to yield benzyl 6-hydroxy-4-azaspiro[2.5]octane-4-carboxylate (4.2 g).

Step 9. Preparation of Benzyl 6-oxo-4-azaspiro[2.5]octane-4-carboxylate

Benzyl 6-hydroxy-4-azaspiro[2.5]octane-4-carboxylate (4.2 g, 16 mmol) and 2-iodoxybenzoic acid (6.7 g, 24 mmol) were added to a solution of acetone (100 mL). Then the reaction solution was warmed to 60° C. to react for 12 hours. Thin layer chromatography (petroleum ether:ethyl acetate=2:1) was used to detect that the reaction was completed, and the reaction solution was extracted, the filtrate was rotary dried and purified by the column chromatography to yield benzyl 6-oxo-4-azaspiro[2.5]octane-4-carboxylate (3.6 g, 85%).

1H-NMR (400 MHz, DMSO-d6): δ ppm 7.34-7.35 (m, 5H), 5.15 (s, 2H), 4.07 (s, 2H), 2.55-2.58 (m, 2H), 1.95-1.98 (m, 2H), 1.09-1.11 (m, 2H), 0.85-0.86 (m, 2H).

Step 10. Preparation of Benzyl (E)-6-(2-(tert-butoxycarbonyl)hydrazono)-4-azaspiro[2.5]octane-4-carboxylate Benzyl 6-oxo-4-azaspiro[2.5]octane-4-carboxylate (3.6 g, 13.9 mmol) and tert-butoxycarbonyl hydrazine (1.98 g, 15 mmol) were added to a solution of tetrahydrofuran (50 mL). The reaction solution was warmed to 70° C. to react for 2 hours. Thin layer chromatography (petroleum ether:ethyl acetate=2:1) was used to detect that the reaction was completed. The reaction solution was extracted, and the filtrate was rotary dried and purified by column chromatography to give benzyl (E)-6-(2-(tert-butoxycarbonyl)hydrazono)-4-azaspiro[2.5]octane-4-carboxylate (5.0 g, 90%).

Step 11. Preparation of Benzyl 6-(2-(tert-butoxycarbonyl)hydrazino)-4-azaspiro[2.5]octane-4-carboxylate Benzyl (E)-6-(2-(tert-Butoxycarbonyl)hydrazono)-4-azaspiro[2.5]octane-4-carboxylate (5.0 g, 13.4 mmol) and sodium cyanoborohydride (1.4 g, 20 mmol) were added to a solution of tetrahydrofuran (100 mL), then p-toluenesulfonic acid (3.8 g, 20 mmol) was added dropwise to the above reaction system. The reaction solution was allowed to react at room temperature for 36 hours. Thin layer chromatography (petroleum ether:ethyl acetate=1:1) was used to detect that the reaction was completed. The reaction solution was extracted, and the filtrate was rotary dried and purified by column chromatography to give benzyl 6-(2-(tert-butoxycarbonyl)hydrazino)-4-azaspiro[2.5]octane-4-carboxylate (4.2 g. 80.4%).

Step 12. Preparation of Benzyl 6-hydrazino-4-azaspiro[2.5]octane-4-carboxylate Benzyl 6-(2-(tert-butoxycarbonyl)hydrazino)-4-azaspiro[2.5]octane-4-carboxylate (4.2 g, 11 mmol) was added to a solution of hydrogen chloride/ethyl acetate (50 mL). The reaction was carried out at room temperature for 12 hours, and thin layer chromatography (petroleum ether:ethyl acetate=2:1) was used to detect that the reaction was completed. The reaction solution was extracted, and the filtrate was rotary dried and purified by column chromatography to yield benzyl 6-hydrazine-4-azaspiro[2.5]octane-4-carboxylate (3.5 g).

1H-NMR (400 MHz, DMSO-d6): δ ppm 7.21-7.35 (m, 10H), 4.46-4.54 (m, 2H), 3.89-3.93 (m, 1H), 3.78-3.81 (m, 1H), 3.68-3.73 (m, 1H), 2.86-2.90 (m, 1H), 2.63-2.68 (m, 1H), 2.08-2.12 (m, 1H), 1.57-1.85 (m, 2H), 1.24-1.29 (m, 1H), 0.65 (s, 2H).0.41-0.44 (m, 2H)

Step 13. Preparation of Methyl 4-((5-chloropyridin-2-yl)oxy)benzoate

Methyl 4-hydroxybenzoate (6.5 g, 49 mmol), 5-chloro-2-fluoropyridine (5.0 g, 33 mmol) and cesium carbonate (20 g, 65 mmol) were dissolved in N,N-dimethyl formamide (50 mL). The reaction solution was refluxed at 110° C. for 12 hours. Thin layer chromatography (petroleum ether:ethyl acetate=5:1) was used to detect that the reaction was completed, and the solvent was rotary dried. The crude compound was partitioned between ethyl acetate (250 mL) and water (250 mL). The organic phase was dried over anhydrous sodium sulfate, filtered and evaporated to dryness under a reduced pressure. The crude compound was purified by column chromatography to yield the product methyl 4-((5-chloropyridin-2-yl)oxy)benzoate (9.0 g, 93%).

MS: m/z 264.2 [M+1]

Step 14. Preparation of 4-((5-chloropyridin-2-yl)oxy)benzoic Acid

Methyl 4-((5-chloropyridin-2-yl)oxy)benzoate (6.5 g, 49 mmol) was dissolved in methanol (100 mL) and water (5 mL). Lithium hydroxide (2.3 g) was then added to the reaction system. The reaction solution was reacted at 45° C. for 12 hours. Thin layer chromatography (petroleum ether: ethyl acetate=1:1) was used to detect that the reaction was completed. The solvent was rotary dried. The crude compound was added with diluted aq. hydrochloric acid (100 mL, 1 M) to pH=7. At this time, a substantial amount of solids was generated, and the solids were filtered and oven-dried to give the product 4-((5-chloropyridin-2-yl)oxy)benzoic acid (6.5 g, as a white solid, 84%).

MS: m/z 250.1 [M+1]

Step 15. Preparation of 4-((5-chloropyridin-2-yl)oxy)benzoyl Chloride 4-((5-Chloropyridin-2-yl)oxy)benzoic acid (6.5 g, 23 mmol) was added to dichlorosulfoxide (20 mL), and the reaction solution was reacted at 80° C. for 3 hours. Thin layer chromatography (petroleum ether:ethyl acetate=3:1) was used to detect that the reaction was completed. The solvent was rotary dried and the crude product 4-((5-chloropyridin-2-yl)oxy)benzoyl chloride (7 g, as a yellow solid) was used directly in the next step.

Step 16. Preparation of 2-((4-((5-chloropyridin-2-yl)oxy)phenyl)(hydroxy)methylene)malononitrile Malononitrile (3.72 g, 56.4 mmol) was dissolved in anhydrous tetrahydrofuran (50 mL) at 0° C., and then sodium hydride (3.6 g, 90 mmol, 60%) was slowly added. After the addition is completed, the reaction was warmed to room temperature and stirred for 1 hour, and then cooled to 0° C. 4-((5-chloropyridin-2-yl)oxy)benzoyl chloride (6 g, 22.2 mmol) dissolved in anhydrous tetrahydrofuran (50 mL) was slowly added to the above reaction solution dropwise. After the dropping process was completed, the reaction solution was stirred at 0° C. for 1 hour. Thin layer chromatography (petroleum ether:ethyl acetate=3:1) was used to detect the completion of reaction, and a new spot was generated. The reaction solution was quenched with saturated aq. ammonium chloride (100 mL), extracted with EtOAc three times (100 mL*3). The organic phase was washed with saturated brine (100 mL), dried over anhydrous sodium sulfate, and rotary dried. The crude compound was mashed with petroleum ether:ethyl acetate=50:1 to give 2-((4-((5-chloropyridin-2-yl)oxy)phenyl)(hydroxy)methylene)malononitrile (8.0 g, as a pale yellow solid, 82%).

MS: m/z 298 [M+1]

Step 17. Preparation of 2-((4-((5-chloropyridin-2-yl)oxy)phenyl)(ethoxy)methylene)malononitrile 2-((4-((5-chloropyridin-2-yl)oxy)phenyl)(hydroxy)methylene)malononitrile (5.0 g, 16.8 mmol) was added to triethyl orthoformate (50 mL). The reaction was warmed to 80° C. and stirred for 12 hours. Thin layer chromatography (petroleum ether:ethyl acetate=3:1) indicated that a product was produced. The reaction solution was filtered, and the filtrate was rotary dried. The resulting solid was mashed with methanol to give 2-((4-((5-chloropyridin-2-yl)oxy)phenyl)(ethoxy)methylene)malononitrile (1.5 g, as a white product, 27.7%).

MS: m/z 326.0 [M+1]

Step 18. Preparation of Benzyl 6-(5-amino-3-(4-((5-chloropyridin-2-yl)oxy)phenyl)-4-cyano-1H-pyrazol-1-yl)-4-azaspiro[2.5]octane-4-carboxylate 2-((4-((5-chloropyridin-2-yl)oxy)phenyl)(ethoxy)methylene)malononitrile (1.0 g. 3.09 mmol), benzyl 6-hydrazino-4-azaspiro[2.5]octane-4-carboxylate (1.28 g, 3.71 mmol) and triethylamine (1.56 g, 15.5 mmol) were dissolved in ethanol (20 mL). The reaction solution was reacted at 25° C. for 12 hours, and thin layer chromatography (petroleum ether:ethyl acetate=2:1) w2as used to detect that the reaction was completed and the reaction was quenched with addition of water, and extracted with ethyl acetate (25 mL*3). The organic phase was dried over anhydrous sodium sulfate, filtered and rotary dried. The crude compound was mashed twice with petroleum ether:ethyl acetate=50:1 to give the product benzyl 6-(5-amino-3-(4-((5-chloropyridin-2-yl)oxy)phenyl)-4-cyano-1H-pyrazol-1-yl)-4-azaspiro[2.5]octane-4-carboxylate (1.5 g, 88%).

MS: m/z 555.2 [M+1]

Step 19. Preparation of 5-amino-3-(4-((5-chloropyridin-2-yl)oxy)phenyl)-1-(4-azaspiro[2.5]oct-6-yl)-1H-pyrazole-4-carboxamide Benzyl 6-(5-amino-3-(4-((5-chloropyridin-2-yl)oxy)phenyl)-4-cyano-1H-pyrazol-1-yl)-4-azaspiro[2.5]octane-4-carboxylate (750 mg, 1.35 mmol) was added to 90% concentrated sulfuric acid (over 10 min) at room temperature, and stirred for 15 minutes, then the reaction system was warmed to 30° C. to react for 24 hours. Thin layer chromatography (dichloromethane:methanol=10:1) was used to detect that the reaction was completed. The reaction solution was slowly poured into aqueous ammonia (50 ml) and adjusted to pH=7, and extracted with ethyl acetate three times (30 mL*3). The combined organic phase was washed with saturated brine (30 mL), dried over anhydrous sodium sulfate, and rotary dried. The crude compound was purified by column chromatography to yield 5-amino-3-(4-((5-chloropyridin-2-yl)oxy)phenyl)-1-(4-azaspiro[2.5]oct-6-yl)-1H-pyrazole-4-carboxamide (480 mg, 78%, as a pale yellow solid).

MS: m/z 439.2 [M+1]

Step 20. Preparation of 5-amino-3-(4-((5-chloropyridin-2-yl)oxy)phenyl)-1-(4-cyano-4-azaspiro[2.5]oct-6-1y)-H-pyrazole-4-carboxamide 5-amino-3-(4-((5-chloropyridin-2-yl)oxy)phenyl)-1-(4-azaspiro[2.5]oct-6-yl)-1H-pyrazole-4-carboxamide (50 mg, 0.113 mmol) was dissolved in N,N-dimethylformamide (5 mL), then cesium carbonate (110 mg, 0.342 mmol) and cyanogen bromide (12.5 mg, 0.113 mmol) were added. The reaction solution was stirred at room temperature for 2 hours, and then subjected to thin layer chromatography to detect that the reaction was completed. The reaction solution was poured into ethyl acetate (50 mL) and washed with water (20 mL*3), dried over anhydrous sodium sulfate, filtered and evaporated to dryness under a reduced pressure. The crude product was purified by a preparative plate (dichloromethane:methanol=50:1) to give the product 5-amino-3-(4-((5-chloropyridin-2-yl)oxy)phenyl)-1-(4-cyano-4-azaspiro[2.5]oct-6-yl)-1H-pyrazole-4-carboxamide (15 mg, 15%).

$^1$H-NMR (400 MHz, DMSO-d6): δ ppm 8.12 (s, 1H), 7.66-7.69 (dd, $J_1$=2.4 Hz, $J_2$=8.4 Hz 2H), 7.56-7.58 (d, J=8 Hz, 2H), 7.21-7.23 (d, J=8 Hz, 2H), 6.92-6.94 (d, J=8 Hz, 1H), 5.61 (s, 1H), 5.19-5.30 (m, 2H), 4.19-4.25 (m, 1H), 3.52-3.66 (m, 2H), 2.34-2.45 (m, 2H), 2.19 (s, 1H), 1.25-1.30 (m, 1H), 1.15-1.20 (m, 1H), 0.78-0.89 (m, 2H), 0.66-0.71 (m, 1H).

MS: m/z 446.2 [M+1]

Example 7

Preparation of (E)-5-amino-3-(4-((5-chloropyridin-2-yl)oxy)phenyl)-1-(4-(4-hydroxybut-2-enoyl)-4-azaspiro[2.5]oct-6-yl)-1H-pyrazole-4-carboxamide (WS-406)

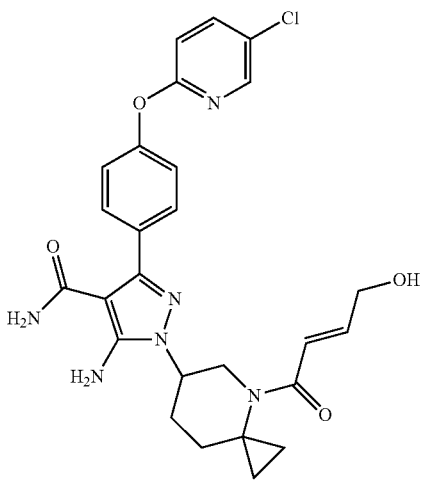 [SMILES: NC(=O)c1c(-c2ccc(Oc3ccc(Cl)cn3)cc2)nn(C2CCC3(CC3)N(C(=O)/C=C/CO)C2)c1N]

The product from the reaction of Step 19 in Example 6 was used as a starting material to prepare the compound of Example 7 by the following steps:

Step 1. Preparation of (E)-5-amino-3-(4-((5-chloropyridin-2-yl)oxy)phenyl)-1-(4-(4-hydroxybut-2-enoyl)-4-azaspiro[2.5]oct-6-yl)-1H-pyrazole-4-carboxamide 4-Hydroxy-2-butenoic acid (100 mg, 0.94 mmol), 1-hydroxybenzotriazole (280 mg, 0.72 mmol), 1-ethyl-(3-dimethylaminopropyl)carbodiimide hydrochloride (260 mg, 0.72 mmol) and triethylamine 160 mg, 1.44 mmol) were dissolved in dichloromethane (2 mL) and stirred at room temperature for 15 min. Then 5-amino-3-(4-((5-chloropyridin-2-yl)oxy)phenyl)-1-(4-azaspiro[2.5]oct-6-yl)-1H-pyrazole-4-carboxamide (100 mg, 0.226 mmol) was added to the above reaction solution, and stirred at room temperature for 12 hours. TLC was used to detect the completion of reaction. The reaction was evaporated to dryness under a reduced pressure. The residue was dissolved in ethyl acetate (20 mL*3), washed with water (30 mL*3), dried over anhydrous sodium sulfate, filtered, and evaporated to dryness under a reduced pressure. The crude product was purified on a preparative plate (dichloromethane:methanol=10:1) to give the product (E)-5-amino-3-(4-((5-chloropyridin-2-yl)oxy)phenyl)-1-(4-(4-hydroxybut-2-enoyl)-4-azaspiro[2.5]oct-6-yl)-1H-pyrazole-4-carboxamide (17 mg, 15%).

1H-NMR (400 MHz, DMSO-d6): δ ppm 8.17 (s, 1H), 7.68-7.69 (d, J=4 Hz, 1H), 7.36-7.57 (m, 2H), 7.24 (brs., 2H), 6.87-6.94 (m, 2H), 6.37-6.43 (m, 1H), 5.75-5.79 (m, 1H), 4.66-4.70 (m, 1H), 3.73-4.06 (m, 2H), 3.28-3.32 (m, 1H), 2.55-2.58 (m, 1H), 2.11-2.21 (m, 2H), 1.18-1.35 (m, 2H), 1.15-1.16 (brs, 1H), 0.72-0.79 (m, 2H).

MS: m/z 523.2 [M+1]

Example 8

Preparation of 1-(4-acryloyl-4-azaspiro[2.5]oct-6-yl)-5-amino-3-(4-((5-chloropyridin-2-yl)oxy)phenyl)-1H-pyrazole-4-carboxamide (WS-407)

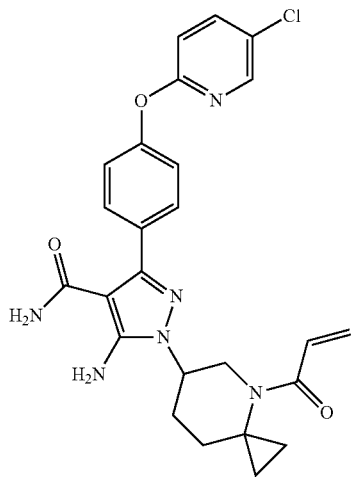 [SMILES: C=CC(=O)N1CC(n2nc(-c3ccc(Oc4ccc(Cl)cn4)cc3)c(C(N)=O)c2N)CCC12CC2]

The product of the reaction from Step 19 of Example 6 was used as a starting material to prepare the compound of Example 8 by the following steps:

Step 1. Preparation of 1-(4-acryloyl-4-azaspiro[2.5]oct-6-yl)-5-amino-3-(4-((5-chloropyridin-2-yl)oxy)phenyl)-1H-pyrazole-4-carboxamide Acrylic acid (8 mg, 0.113 mmol) was added to 2-(7-azobenzotriazol)-N,N,N',N'-tetramethyluronium hexafluorophosphate (65 mg, 0.171 mmol) and triethylamine (35 mg, 0.342 mmol) dissolved in dichloromethane (2 mL), and stirred for 15 min. Then 5-amino-3-(4-((5-chloropyridin-2-yl)oxy)phenyl)-1-(4-azaspiro[2.5]oct-6-yl)-1H-pyrazole-4-carboxamide (50 mg, 0.113 mmol) was added to the above reaction solution and stirred at room temperature for 2 hours. TCL was used to detect the completion of reaction. The reaction was evaporated to dryness under a reduced pressure. The residue was dissolved in ethyl acetate (20 mL*3), washed with water (30 mL*3), dried over anhydrous sodium sulfate, filtered, and evaporated to dryness under a reduced pressure. The crude product was purified by preparative HPLC to give the product 1-(4-acryloyl-4-azaspiro[2.5]oct-6-yl)-5-amino-3-(4-((5-chloropyridin-2-yl)oxy)phenyl)-1H-pyrazole-4-carboxamide (8 mg, as a red solid).

1H-NMR (400 MHz, DMSO-d6): δ ppm 8.17 (s, 1H), 7.68-7.69 (d, J=4 Hz, 1H), 7.36-7.57 (m, 2H), 7.24 (brs., 2H), 6.87-6.94 (m, 2H), 6.37-6.43 (m, 1H), 5.75-5.79 (m, 1H), 4.66-4.70 (m, 1H), 3.73-4.06 (m, 2H), 3.28-3.32 (m, 1H), 2.55-2.58 (m, 1H), 2.11-2.21 (m, 2H), 1.18-1.35 (m, 2H), 1.15-1.16 (brs, 1H), 0.72-0.79 (m, 2H).

MS: m/z 493.2 [M+1]

Example 9

Preparation of 5-amino-1-(4-cyano-4-azaspiro[2.5]oct-6-yl)-3-(4-(2,4-difluorophenoxy)phenyl)-1H-pyrazole-4-carboxamide (WS-408)

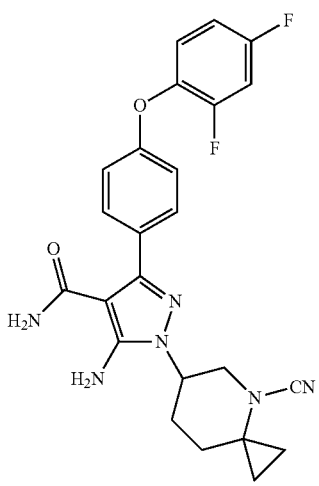 [SMILES: N#CN1CC(n2nc(-c3ccc(Oc4ccc(F)cc4F)cc3)c(C(N)=O)c2N)CCC12CC2]

The compound of Example 9 was prepared by a similar method to Example 6 starting from a corresponding starting material.

1H-NMR (400 MHz, DMSO-d6): δ ppm 7.47-7.49 (dd, $J_1$=8 Hz, $J_2$=8.4 Hz 2H), 7.08-7.14 (m, 1H), 6.87-7.02 (m, 4H), 5.56 (s, 1H), 5.13-5.16 (s, 2H), 4.17-4.22 (m, 1H), 3.60-3.66 (m, 1H), 3.48-3.51 (m, 1H), 2.34-2.41 (m, 2H), 2.15-2.17 (s, 1H), 1.26-1.30 (m, 1H), 1.14-1.19 (m, 1H), 0.78-0.88 (m, 2H), 0.66-0.70 (m, 1H).

MS: m/z 465.2 [M+1]

Example 10

Preparation of (E)-5-amino-3-(4-(2,4-difluorophenoxy)phenyl)-1-(4-(4-hydroxybut-2-enoyl)-4-azaspiro[2.5]oct-6-yl)-1H-pyrazole-4-carboxamide (WS-409)

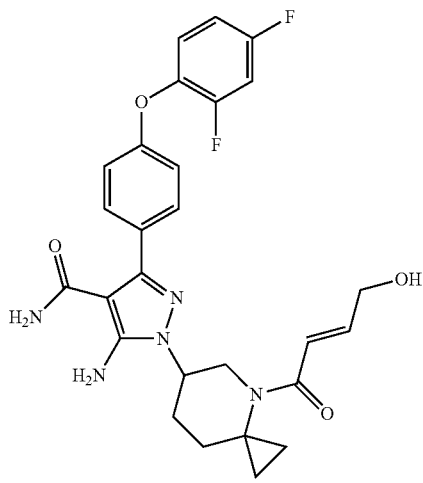 [SMILES: NC(=O)c1c(-c2ccc(Oc3ccc(F)cc3F)cc2)nn(C2CCC3(CC3)N(C(=O)/C=C/CO)C2)c1N]

The compound of Example 10 was prepared by a similar method to Example 7 starting from a corresponding starting material.

1H-NMR (400 MHz, DMSO-d6): δ ppm 7.49-7.51 (d, J=8 Hz, 2H), 7.07-7.18 (m, 1H), 7.69-7.01 (m, 3H), 6.87-6.94 (m, 2H), 5.74 (s, 2H), 5.16 (s, 1H), 4.62 (brs., 1H), 4.40 (s, 2H), 3.93 (s, 1H), 3.22 (m, 1H), 2.14-2.17 (d, J=12 Hz, 2H), 1.99-2.00 (m, 1H), 1.36-1.42 (m, 2H), 1.16-1.21 (m, 1H), 0.69-0.73 (m, 2H).

MS: m/z 524.4 [M+1]

Example 11

Preparation of 1-(4-acryloyl-4-azaspiro[2.5]oct-6-yl)-5-amino-3-(4-(2,4-difluorophenoxy)phenyl)-1H-pyrazole-4-carboxamide (WS-410)

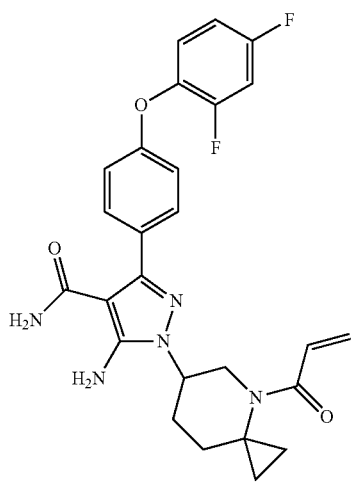 [SMILES: C=CC(=O)N1CC(n2nc(-c3ccc(Oc4ccc(F)cc4F)cc3)c(C(N)=O)c2N)CCC12CC2]

The compound of Example 11 was prepared by a similar method to Example 8 starting from a corresponding starting material.

1H-NMR (400 MHz, DMSO-d6): δ ppm 7.46-7.49 (d, J=12 Hz, 2H), 7.08-7.18 (m, 1H), 6.99-7.01 (m, 2H), 6.42-6.43 (d, J=4 Hz, 1H), 5.63-5.77 (brs., 1H), 5.62 (s, 2H), 5.09 (brs., 2H), 4.64 (m, 1H), 3.91 (m, 1H), 3.24 (m, 1H), 2.57 (m, 1H), 2.01-2.18 (m, 2H), 1.31-1.40 (m, 1H), 1.22-1.24 (m, 1H), 1.12-1.18 (m, 1H), 0.68-0.77 (m, 2H).

MS: m/z 494.3 [M+1]

Example 12

Preparation of (R)-5-amino-1-(4-cyano-4-azaspiro[2.5]oct-6-yl)-3-(4-(2,4-difluorophenoxy)phenyl)-1H-pyrazole-4-carboxamide (WS-411) and (S)-5-amino-1-(4-cyano-4-azaspiro[2.5]oct-6-yl)-3-(4-(2,4-difluorophenoxy)phenyl)-1H-pyrazole-4-carboxamide (WS-412)

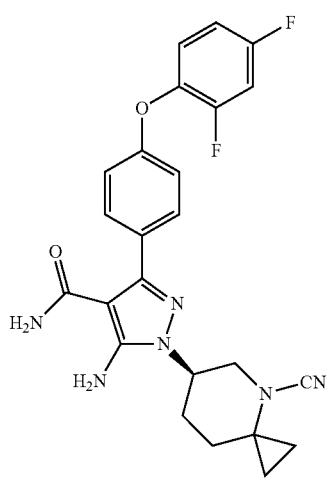

WS-411

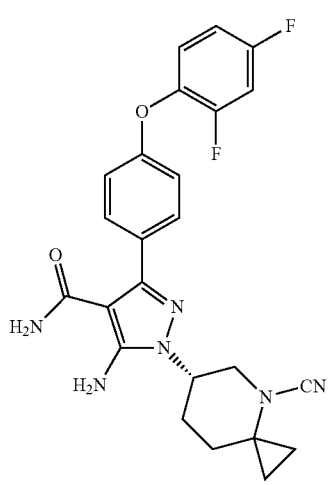

WS-412

The compounds of Example 12 were obtained from chiral resolution of the product of Example 9. The resolution conditions were: Supercritical fluid chromatography (ChiralPak AD 5μ, 21×250 mm col, 27% methanol, 70 mL/min).

WS-411 spectrum data:

$^1$H-NMR (400 MHz, CDCl3): δ ppm 7.48 (d, J=8.4 Hz, 2H), 7.15-7.09 (m, 1H), 7.02-6.95 (m, 3H), 6.92-6.88 (m, 1H), 5.75 (s, 2H), 5.29 (s, 2H), 4.32-4.26 (m, 1H), 3.65-3.52 (m, 2H), 2.42-2.30 (m, 2H), 2.18-2.15 (m, 1H), 1.19-1.14 (m, 1H), 0.87-0.67 (m, 4H).

MS: m/z 465.4 [M+H]

WS-412 spectrum data:

$^1$H-NMR (400 MHz, CDCl3): δ ppm 7.48 (d, J=8.4 Hz, 2H), 7.15-7.09 (m, 1H), 7.02-6.95 (m, 3H), 6.92-6.88 (m, 1H), 5.75 (s, 2H), 5.29 (s, 2H), 4.32-4.26 (m, 1H), 3.65-3.52 (m, 2H), 2.42-2.30 (m, 2H), 2.18-2.15 (m, 1H), 1.19-1.14 (m, 1H), 0.87-0.67 (m, 4H).

MS: m/z 465.4 [M+H]

Example 13

Preparation of (R)-5-amino-3-(4-((5-chloropyridin-2-yl)oxy)phenyl)-1-(4-cyano-4-azaspiro[2.5]oct-6-yl)-1H-pyrazole-4-carboxamide (WS-413) and (S)-5-amino-3-(4-((5-chloropyridin-2-yl)oxy)phenyl)-1-(4-cyano-4-azaspiro[2.5]oct-6-yl)-1H-pyrazole-4-carboxamide (WS-414)

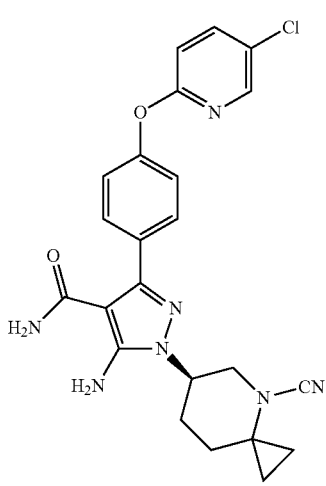

WS-413

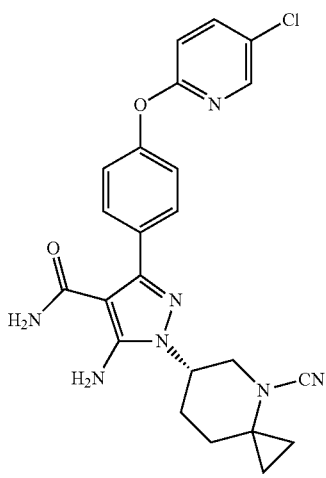

WS-414

The products of Example 13 were obtained from chiral resolution of the product of Example 6. The resolution conditions were: Supercritical fluid chromatography (ChiralPak AD 5μ, 21×250 mm col, 27% methanol, 70 mL/min).

WS-413 spectrum data:

$^1$H-NMR (400 MHz, CDCl3): δ ppm 8.12 (s, 1H), 7.69-7.67 (m, 1H), 7.57 (d, J=8.4 Hz, 2H), 7.22 (d, J=8.4 Hz, 2H), 6.93 (d, J=8.8 Hz, 1H), 5.60 (s, 2H), 5.24 (s, 2H), 4.25-4.20 (m, 1H), 3.67-3.48 (m, 2H), 2.42-2.35 (m, 2H), 2.19-2.16 (m, 1H), 1.30-1.26 (m, 1H), 1.21-1.16 (m, 1H), 0.90-0.79 (m, 2H), 0.71-0.67 (m, 1H).

MS: m/z 464.4 [M+H]

WS-414 spectrum data:

$^1$H-NMR (400 MHz, CDCl3): δ ppm 8.12 (s, 1H), 7.69-7.67 (m, 1H), 7.57 (d, J=8.4 Hz, 2H), 7.22 (d, J=8.4 Hz, 2H), 6.93 (d, J=8.8 Hz, 1H), 5.60 (s, 2H), 5.24 (s, 2H), 4.25-4.20 (m, 1H), 3.67-3.48 (m, 2H), 2.42-2.35 (m, 2H), 2.19-2.16 (m, 1H), 1.30-1.26 (m, 1H), 1.21-1.16 (m, 1H), 0.90-0.79 (m, 2H), 0.71-0.67 (m, 1H).

MS: m/z 464.4 [M+H]

Example 14

Preparation of 5-amino-1-(4-(2-butynoyl)-4-azaspiro[2.5]oct-6-yl)-3-(4-((5-chloropyridin-2-yl)oxy)phenyl)-1H-pyrazole-4-carboxamide (WS-415)

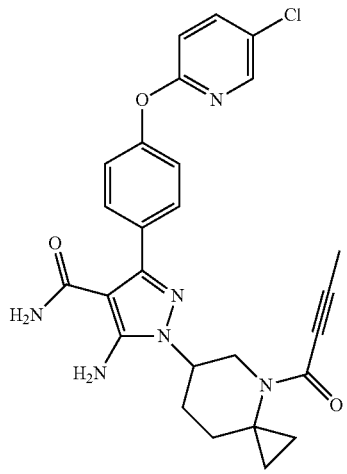 [SMILES: CC#CC(=O)N1CC(n2nc(-c3ccc(Oc4ccc(Cl)cn4)cc3)c(C(N)=O)c2N)CCC12CC2]

The compound of Example 14 was prepared by a similar method to Example 8 starting from a corresponding starting material.

¹H-NMR (400 MHz, MeOD): δ ppm 8.08 (s, 1H), 7.85 (d, J=8.8 Hz, 1H), 7.61-7.57 (m, 2H), 7.23-7.20 (m, 2H), 7.05 (d, J=8.8 Hz, 1H), 4.40-4.37 (m, 1H), 4.22-3.90 (m, 2H), 3.60-3.31 (m, 1H), 2.34-2.31 (m, 1H), 2.16-2.09 (m, 2H), 2.06 (s, 3H), 1.14-0.75 (m, 4H).

MS: m/z 505.1 [M+H]

Example 15

Preparation of (R)-5-amino-1-(4-(2-butynoyl)-4-azaspiro[2.5]oct-6-yl)-3-(4-((5-chloropyridin-2-yl)oxy)phenyl)-1H-pyrazole-4-carboxamide (WS-416) and (S) 5-amino-1-(4-(2-butynoyl)-4-azaspiro[2.5]oct-6-yl)-3-((5-chloropyridin-2-yl)oxy)phenyl)-1H-pyrazole-4-carboxamide (WS-417)

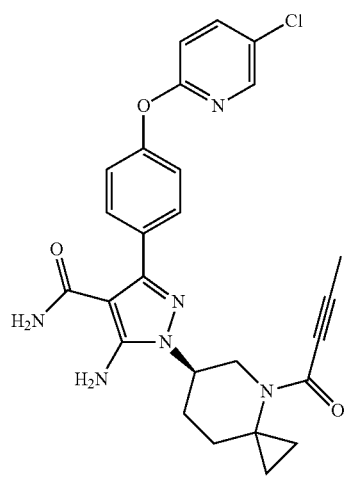

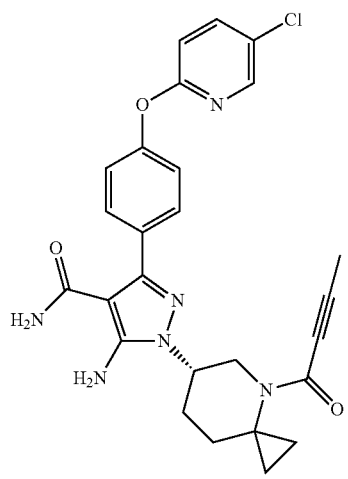

The compounds of Example 15 were obtained from chiral resolution of the product of Example 14. The resolution conditions were: Supercritical fluid chromatography (ChiralPak AD 5μ, 21×250 mm col, 27% methanol, 70 mL/min).

WS-416 spectrum data:
¹H-NMR (400 MHz, MeOD): δ ppm 8.08 (s, 1H), 7.85 (d, J=8.8 Hz, 1H), 7.61-7.57 (m, 2H), 7.23-7.20 (m, 2H), 7.05 (d, J=8.8 Hz, 1H), 4.40-4.37 (m, 1H), 4.22-3.90 (m, 2H), 3.60-3.31 (m, 1H), 2.34-2.31 (m, 1H), 2.16-2.09 (m, 2H), 2.06 (s, 3H), 1.14-0.75 (m, 4H).

MS: m/z 505.1 [M+H]

WS-417 spectrum data:
¹H-NMR (400 MHz, MeOD): δ ppm 8.08 (s, 1H), 7.85 (d, J=8.8 Hz, 1H), 7.61-7.57 (m, 2H), 7.23-7.20 (m, 2H), 7.05 (d, J=8.8 Hz, 1H), 4.40-4.37 (m, 1H), 4.22-3.90 (m, 2H), 3.60-3.31 (m, 1H), 2.34-2.31 (m, 1H), 2.16-2.09 (m, 2H), 2.06 (s, 3H), 1.14-0.75 (m, 4H).

MS: m/z 505.1 [M+H]

Example 16

Preparation of (R)-1-(4-acryloyl-4-azaspiro[2.5]oct-6-yl)-5-amino-3-(4-((5-chloropyridin-2-yl)oxy)phenyl)-1H-pyrazole-4-carboxamide (WS-418) and (S)-1-(4-acryloyl-4-azaspiro[2.5]oct-6-yl)-5-amino-3-(4-((5-chloropyridin-2-yl)oxy)phenyl)-1H-pyrazole-4-carboxamide (WS-419)

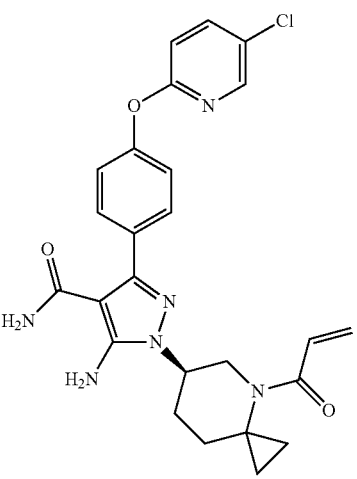

-continued

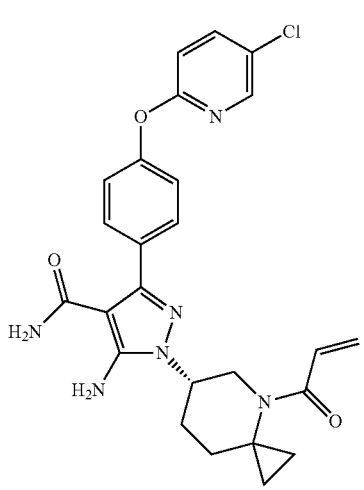

WS-419

The compounds of Example 16 were obtained from chiral resolution of the compound of Example 8. The resolution conditions were: Supercritical fluid chromatography (ChiralPak AD 5μ, 21×250 mm col, 27% methanol, 70 mL/min).

WS-418 spectrum data:
$^1$H-NMR (400 MHz, CDCl$_3$): δ ppm 8.12 (s, 1H), 7.69-7.66 (m, 1H), 7.59 (d, J=8.4 Hz, 2H), 7.21 (d, J=8.4 Hz, 2H), 6.94-6.88 (m, 3H), 6.41-6.37 (m, 1H), 5.75 (s, 2H), 5.43 (s, 2H), 4.68-4.66 (m, 1H), 4.01-3.95 (m, 1H), 3.31-3.19 (m, 2H), 2.63-2.56 (m, 1H), 2.19-2.12 (m, 2H), 1.40-1.37 (m, 2H), 1.25-1.10 (m, 2H).
MS: m/z 493.1[M+H]

WS-419 spectrum data:
$^1$H-NMR (400 MHz, CDCl$_3$): δ ppm 8.12 (s, 1H), 7.69-7.66 (m, 1H), 7.59 (d, J=8.4 Hz, 2H), 7.21 (d, J=8.4 Hz, 2H), 6.94-6.88 (m, 3H), 6.41-6.37 (m, 1H), 5.75 (s, 2H), 5.43 (s, 2H), 4.68-4.66 (m, 1H), 4.01-3.95 (m, 1H), 3.31-3.19 (m, 2H), 2.63-2.56 (m, 1H), 2.19-2.12 (m, 2H), 1.40-1.37 (m, 2H), 1.25-1.10 (m, 2H).
MS: m/z 493.1[M+H]

Example 17

Preparation of 5-amino-1-(4-(2-butynoyl)-4-azaspiro[2.5]oct-6-yl)-3-(4-(2,4-difluorophenoxy)phenyl)-1H-pyrazole-4-carboxamide (WS-420)

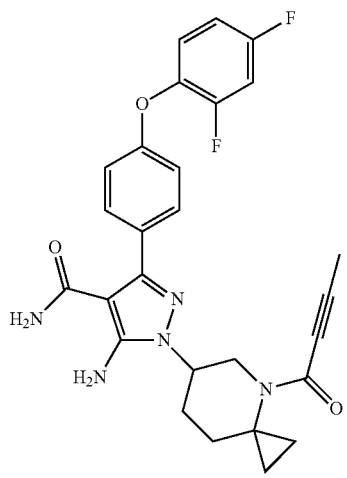 [SMILES: CC#CC(=O)N1CC(n2nc(-c3ccc(Oc4ccc(F)cc4F)cc3)c(C(N)=O)c2N)CCC12CC2]

The compound of Example 17 was prepared by a similar method to Example 8 starting from a corresponding starting material.
$^1$H-NMR (400 MHz, CDCl3): δ ppm 7.52 (d, J=8.0 Hz, 1H), 7.13-7.10 (m, 1H), 7.03-6.95 (m, 3H), 6.91-6.88 (m, 1H), 5.65 (s, 2H), 5.18 (s, 2H), 4.56-3.92 (m, 3H), 3.25-3.20 (m, 1H), 2.52-2.51 (m, 1H), 2.21-2.14 (m, 2H), 2.09 (s, 3H), 1.08-0.88 (m, 2H), 0.72-0.65 (m, 2H).
MS: m/z 506.4 [M+H]

Example 18

Preparation of (R)-5-amino-1-(4-(2-butynoyl)-4-azaspiro[2.5]oct-6-yl)-3-(4-(2,4-difluorophenoxy)phenyl)-1H-pyrazole-4-carboxamide (WS-421) and (R)-5-amino-1-(4-(2-butynoyl)-4-azaspiro[2.5]oct-6-yl)-3-(4-(2,4-difluorophenoxy)phenyl)-1H-pyrazole-4-carboxamide (WS-422)

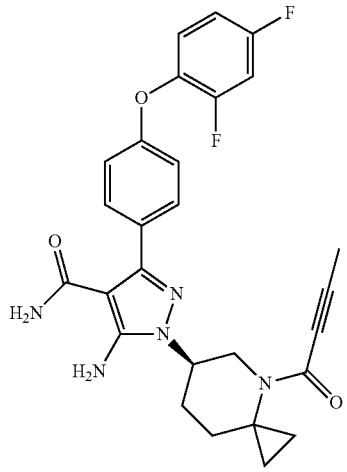

WS-421

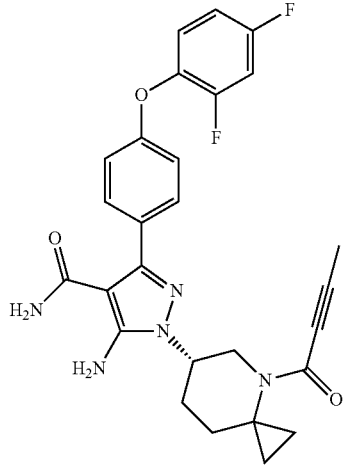

WS-422

The products of Example 18 were obtained from chiral resolution of the product of Example 17. The resolution conditions were: Supercritical fluid chromatography (ChiralPak AD 5μ, 21×250 mm col, 27% methanol, 70 mL/min).

WS-421 spectrum data:
$^1$H-NMR (400 MHz, CDCl3): δ ppm 7.52 (d, J=8.0 Hz, 1H), 7.13-7.10 (m, 1H), 7.03-6.95 (m, 3H), 6.91-6.88 (m, 1H), 5.65 (s, 2H), 5.18 (s, 2H), 4.56-3.92 (m, 3H), 3.25-3.20 (m, 1H), 2.52-2.51 (m, 1H), 2.21-2.14 (m, 2H), 2.09 (s, 3H), 1.08-0.88 (m, 2H), 0.72-0.65 (m, 2H).

MS: m/z 506.4 [M+H]

WS-422 spectrum data:

¹H-NMR (400 MHz, CDCl3): δ ppm 7.52 (d, J=8.0 Hz, 1H), 7.13-7.10 (m, 1H), 7.03-6.95 (m, 3H), 6.91-6.88 (m, 1H), 5.65 (s, 2H), 5.18 (s, 2H), 4.56-3.92 (m, 3H), 3.25-3.20 (m, 1H), 2.52-2.51 (m, 1H), 2.21-2.14 (m, 2H), 2.09 (s, 3H), 1.08-0.88 (m, 2H), 0.72-0.65 (m, 2H).

MS: m/z 506.4 [M+H]

Example 19

Preparation of 5-amino-1-(1-cyano-pyrrolidin-3-yl)-3-(4-(2,4-difluorophenoxy)phenyl)-1H-pyrazole-4-carboxamide (WS-423)

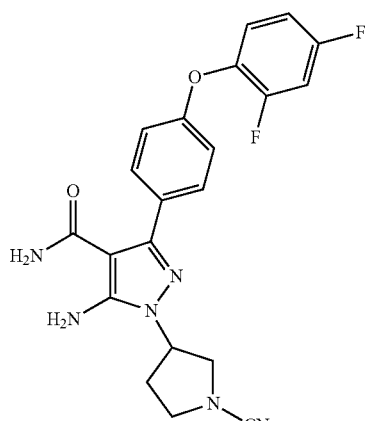

The compound of Example 19 was prepared by a similar method to Example 6 starting from a corresponding starting material.

¹H-NMR (400 MHz, CDCl3): δ ppm 7.50 (d, J=8.4 Hz, 2H), 7.16-7.10 (m, 1H), 7.02-6.95 (m, 3H), 6.92-6.88 (m, 1H), 5.52 (s, 2H), 5.34 (s, 2H), 4.69-4.66 (m, 1H), 3.87-3.76 (m, 3H), 3.60-3.54 (m, 1H), 2.56-2.51 (m, 1H), 2.35-2.30 (m, 1H).

MS: m/z 425.3 [M+H]

Example 20

Preparation of 5-amino-1-(1-cyanopiperidin-4-yl)-3-(4-(2,4-difluorophenoxy)phenyl)-1H-pyrazole-4-carboxamide (WS-424)

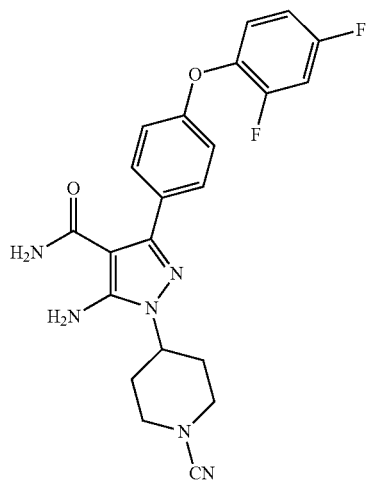 [SMILES: N#CN1CCC(n2nc(-c3ccc(Oc4ccc(F)cc4F)cc3)c(C(N)=O)c2N)CC1]

The compound of Example 20 was prepared by a similar method to Example 6 starting from a corresponding starting material.

¹H-NMR (400 MHz, CDCl3): δ ppm 7.49 (d, J=8.8 Hz, 2H), 7.15-7.09 (m, 1H), 7.02-6.92 (m, 3H), 6.92-6.88 (m, 1H), 5.43 (s, 2H), 5.21 (s, 2H), 3.99-3.93 (m, 1H), 3.66-3.62 (m, 2H), 3.23-3.17 (m, 2H), 2.41-2.32 (m, 1H), 2.03-2.01 (m, 1H).

MS: m/z 439.2 [M+H]

Example 21

Preparation of 1-(1-acryloyl-6-methylpiperidin-3-yl)-5-amino-3-(4-(2-chloro-4-fluorophenoxy)phenyl)-1H-pyrazole-4-carboxamide (WS-425)

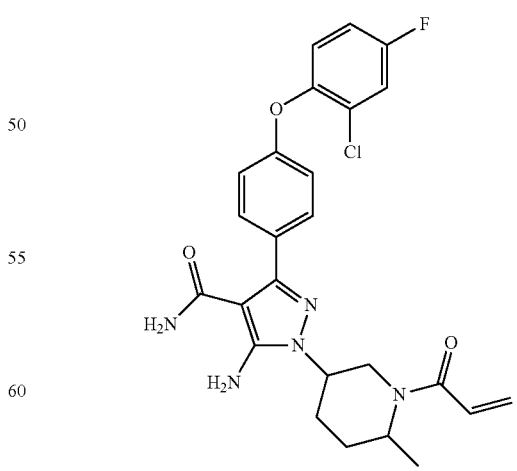

The compound of Example 21 was prepared by a similar method to Example 6 starting from a corresponding starting material.

¹H-NMR (400 MHz, CDCl3): δ ppm 7.52-7.49 (m, 2H), 7.25-7.25 (m, 1H), 7.09-6.97 (m, 4H), 6.59-6.57 (m, 1H), 6.32-6.12 (m, 1H), 5.87-5.85 (m, 2H), 5.68-5.60 (m, 2H), 4.70-4.25 (m, 1H), 3.88-3.85 (m, 1H), 3.48-3.46 (m, 1H), 2.72-2.61 (m, 1H), 2.04-1.97 (m, 2H), 1.82-1.77 (m, 2H), 1.41-1.35 (m, 3H).
MS: m/z 498.2 [M+H]

Example 22

Preparation of 5-amino-3-(4-(2-chloro-4-fluorophenoxy)phenyl)-1-(1-cyano-6-methylpiperidin-3-yl)-1H-pyrazole-4-carboxamide (WS-426)

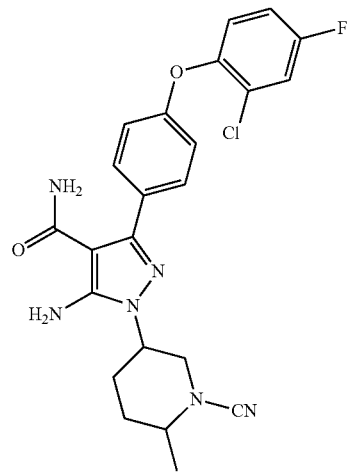 [SMILES: CC1CCC(n2nc(-c3ccc(Oc4ccc(F)cc4Cl)cc3)c(C(N)=O)c2N)CN1C#N]

The compound of Example 22 was prepared by a similar method to Example 6 starting from a corresponding starting material.
¹H-NMR (400 MHz, CDCl3): δ ppm 7.49 (d, J=8.4 Hz, 2H), 7.23-7.24 (m, 1H), 7.07-7.11 (m, 1H), 6.97-7.04 (m, 3H), 6.55 (s, 1H), 5.55 (s, 1H), 5.21 (s, 1H), 4.03-4.09 (m, 1H), 3.60-3.71 (m, 2H), 3.34-3.40 (m, 1H), 2.29-2.35 (m, 1H), 1.93-2.04 (m, 2H), 1.82-1.86 (m, 1H), 1.38 (d, J=6.8 Hz, 2H).
MS: m/z 469.3 [M+H]

Example 23

Preparation of 5-amino-1-(1-(2-butynoyl)-6-methylpiperidin-3-yl)-3-(4-(2-chloro-4-fluorophenoxy)phenyl)-1H-pyrazole-4-carboxamide (WS-427)

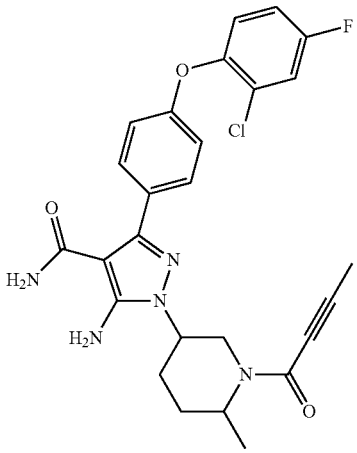 [SMILES: CC#CC(=O)N1CC(n2nc(-c3ccc(Oc4ccc(F)cc4Cl)cc3)c(C(N)=O)c2N)CCC1C]

The compound of Example 23 was prepared by a similar method to Example 6 starting from a corresponding starting material.
¹H-NMR (400 MHz, CDCl3): δ ppm 7.52-7.49 (m, 2H), 7.29-7.23 (m, 1H), 7.06-6.97 (m, 4H), 5.63-5.61 (m, 2H), 5.35-5.23 (m, 2H), 4.91-4.72 (m, 1H), 3.91-3.81 (m, 1H), 3.26-3.17 (m, 1H), 2.51-2.42 (m, 2H), 2.06 (d, J=16.8 Hz, 2H), 1.81-1.76 (m, 2H), 1.41-1.34 (m, 3H).
MS: m/z 510.2 [M+H]

Example 24

Preparation of 5-amino-3-(4-(4-chloro-2-fluorophenoxy)phenyl)-1-(1-cyano-6-methylpiperidin-3-yl)-1H-pyrazole-4-carboxamide (WS-428)

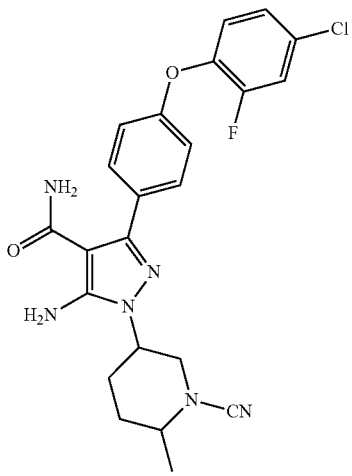 [SMILES: CC1CCC(n2nc(-c3ccc(Oc4ccc(Cl)cc4F)cc3)c(C(N)=O)c2N)CN1C#N]

The compound of Example 24 was prepared by a similar method to Example 6 starting from a corresponding starting material.
¹H-NMR (400 MHz, CD3OD): δ ppm 7.49 (d, J=8.8 Hz, 2H), 7.40-7.36 (m, 1H), 7.25-7.16 (m, 2H), 7.07 (d, J=8.8 Hz, 2H), 4.33 (s, 2H), 3.70-3.63 (m, 1H), 3.60-3.57 (m, 1H), 3.42-3.38 (m, 1H), 2.28-2.25 (m, 1H), 2.19-2.19 (m, 3H), 1.37 (d, J=6.8 Hz, 3H).
MS: m/z 469.1 [M+H]

Example 25

Preparation of 1-(1-acryloyl-6-methylpiperidin-3-yl)-5-amino-3-(4-(4-chloro-2-fluorophenoxy)phenyl)-1H-pyrazole-4-carboxamide (WS-429)

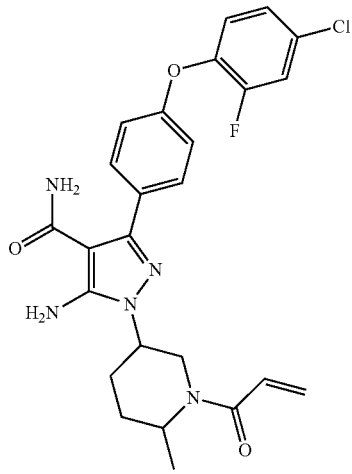 [SMILES: C=CC(=O)N1CC(n2nc(-c3ccc(Oc4ccc(Cl)cc4F)cc3)c(C(N)=O)c2N)CCC1C]

The compound of Example 25 was prepared by a similar method to Example 6 starting from a corresponding starting material.

$^1$H-NMR (400 MHz, CDOD3): δ ppm 7.55-7.53 (m, 2H), 7.40-7.38 (m, 1H), 7.25-7.16 (m, 2H), 7.09 (d, J=8.4 Hz, 1H), 6.85-6.73 (m, 1H), 6.24-6.15 (m, 1H), 5.78-5.72 (m, 1H), 4.70-4.40 (m, 2H), 4.23-4.01 (m, 1H), 2.38-2.32 (m, 1H), 2.04-2.02 (m, 1H), 1.91-1.77 (m, 2H), 1.37 (d, J=6.8, 3H).

MS: m/z 498.1 [M+H]

Example 26

Preparation of 5-amino-1-(1-(2-butynoyl)-6-methylpiperidin-3-yl)-3-(4-(4-chloro-2-fluorophenoxy)phenyl)-1H-pyrazole-4-carboxamide (WS-430)

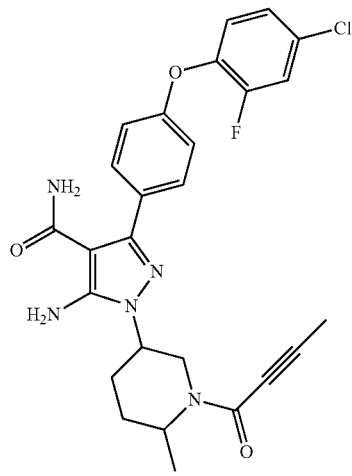 [SMILES: CC#CC(=O)N1CC(n2nc(-c3ccc(Oc4ccc(Cl)cc4F)cc3)c(C(N)=O)c2N)CCC1C]

The compound of Example 26 was prepared by a similar method to Example 6 starting from a corresponding starting material.

$^1$H-NMR (400 MHz, CDCl$_3$): δ ppm 7.54-7.50 (m, 2H), 7.25-7.22 (m, 1H), 7.20-7.02 (m, 4H), 5.37 (s, 2H), 5.92-5.91 (m, 1H), 4.61-4.59 (m, 1H), 4.68-4.41 (m, 1H), 3.94-3.83 (m, 1H), 3.69-3.63 (m, 1H), 2.52-2.43 (m, 1H), 2.03 (d, J=16.8 Hz, 3H), 2.011-1.76 (m, 3H), 1.41-1.34 (m, 3H).

MS: m/z 510.1 [M+H]

Examples 27-40

The compounds having the structures shown in Examples 27 to 40 can be prepared by the methods similar to Examples 1 to 26 of the present invention.

| Ex. No. | Structure | Name | MS (M + 1) |
|---|---|---|---|
| 27 | 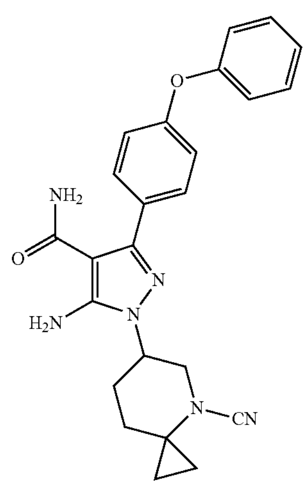 [SMILES: N#CN1CC(n2nc(-c3ccc(Oc4ccccc4)cc3)c(C(N)=O)c2N)CCC12CC2] | 5-amino-1-(4-cyano-4-azaspiro[2.5]oct-6-yl)-3-(4-phenoxyphenyl)-1H-pyrazole-4-carboxamide (WS-431) | 429 |

-continued

| Ex. No. | Structure | Name | MS (M + 1) |
|---|---|---|---|
| 28 | 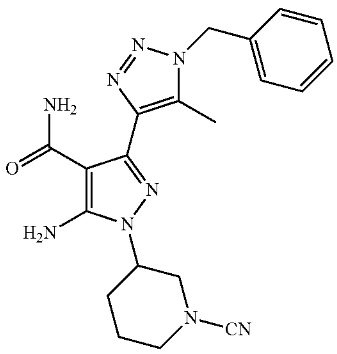 [SMILES: Cc1c(-c2nn(C3CCCN(C#N)C3)c(N)c2C(N)=O)nnn1Cc1ccccc1] | 5-amino-3-(1-benzyl-5-methyl-1H-1,2,3-triazol-4-yl)-1-(1-cyanopiperidin-3-yl)-1H-pyrazole-4-carboxamide (WS-432) | 406 |
| 29 | 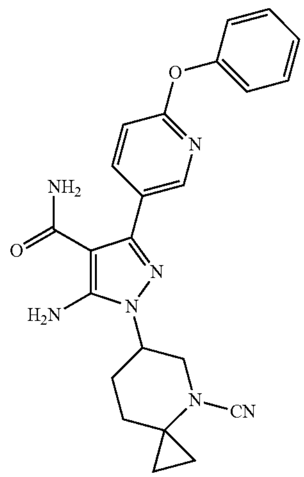 [SMILES: N#CN1CC(n2nc(-c3ccc(Oc4ccccc4)nc3)c(C(N)=O)c2N)CCC12CC2] | 5-amino-1-(4-cyano-4-azaspiro[2.5]oct-6-yl)-3-(6-phenoxypyridin-3-yl)-1H-pyrazole-4-carboxamide (WS-433) | 430 |
| 30 | 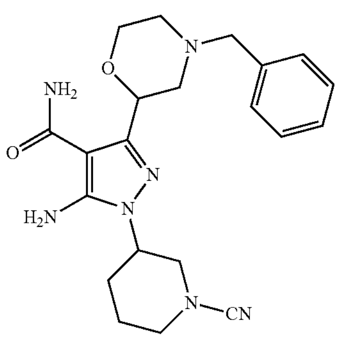 [SMILES: N#CN1CCCC(n2nc(C3CN(Cc4ccccc4)CCO3)c(C(N)=O)c2N)C1] | 5-amino-3-(4-benzylmorpholin-2-yl)-1-(1-cyanopiperidin-3-yl)-1H-pyrazole-4-carboxamide (WS-434) | 410 |
| 31 | 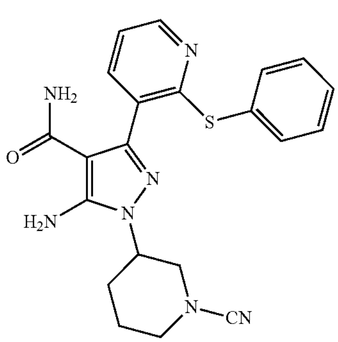 [SMILES: N#CN1CCCC(n2nc(-c3cccnc3Sc3ccccc3)c(C(N)=O)c2N)C1] | 5-amino-1-(1-cyanopiperidin-3-yl)-3-(2-(phenylthio)piperidin-3-yl)-1H-pyrazole-4-carboxamide (WS-435) | 420 |

| Ex. No. | Structure | Name | MS (M + 1) |
|---|---|---|---|
| 32 | 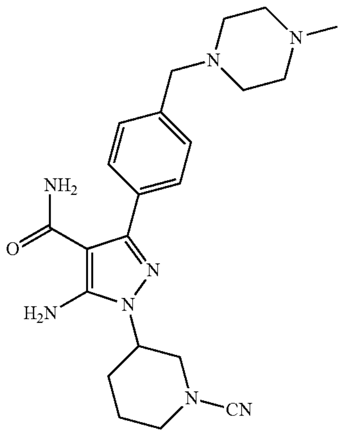 [SMILES: CN1CCN(Cc2ccc(-c3nn(C4CCCN(C#N)C4)c(N)c3C(N)=O)cc2)CC1] | 5-amino-1-(1-cyanopiperidin-3-yl)-3-4-((4-methylpiperazin-1-yl)methyl)phenyl)-1H-pyrazole-4-carboxamide (WS-436) | 423 |
| 33 | 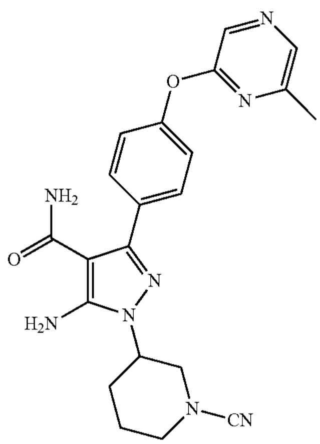 [SMILES: Cc1cncc(Oc2ccc(-c3nn(C4CCCN(C#N)C4)c(N)c3C(N)=O)cc2)n1] | 5-amino-1-(1-cyanopiperidin-3-yl)-3-(4-((6-methylpyrazin-2-yl)oxy)phenyl)-1H-pyrazole-4-carboxamide (WS-437) | 419 |
| 34 | 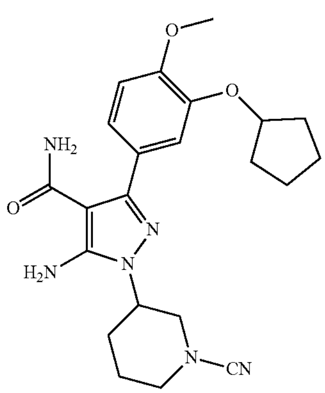 [SMILES: COc1ccc(-c2nn(C3CCCN(C#N)C3)c(N)c2C(N)=O)cc1OC1CCCC1] | 5-amino-1-(1-cyanopiperidin-3-yl)-3-(3-(cyclopentyloxy)-4-methoxyphenyl)-1H-pyrazole-4-carboxamide (WS-438) | 425 |

-continued

| Ex. No. | Structure | Name | MS (M + 1) |
|---|---|---|---|
| 35 | 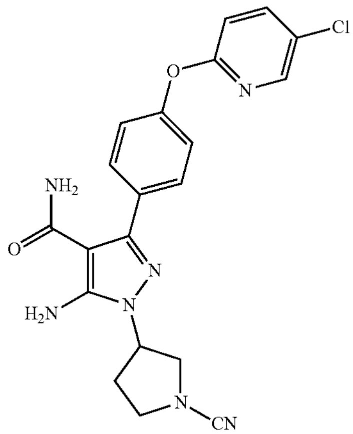 [SMILES: N#CN1CCC(n2nc(-c3ccc(Oc4ccc(Cl)cn4)cc3)c(C(N)=O)c2N)C1] | 5-amino-3-(4-((5-chloropyridin-2-yl)oxy)phenyl)-1-(1-cyanopyrrolidin-3-yl)-1H-pyrazole-4-carboxamide (WS-439) | 424 |
| 36 | 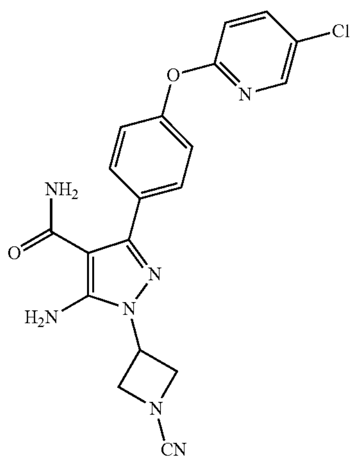 [SMILES: N#CN1CC(n2nc(-c3ccc(Oc4ccc(Cl)cn4)cc3)c(C(N)=O)c2N)C1] | 5-amino-3-(4-((5-chloropyridin-2-yl)oxy)phenyl)-1-(1-cyanoazetidin-3-yl)-1H-pyrazole-4-carboxamide (WS-440) | 410 |
| 37 | 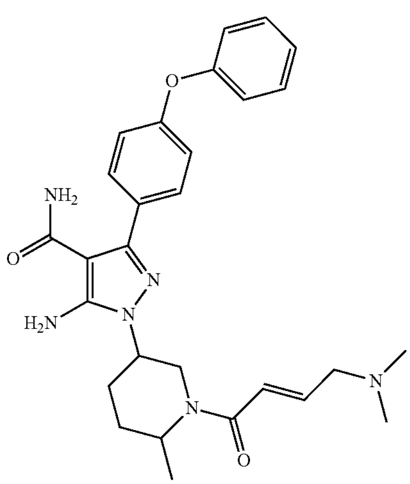 [SMILES: CC1CCC(n2nc(-c3ccc(Oc4ccccc4)cc3)c(C(N)=O)c2N)CN1C(=O)/C=C/CN(C)C] | (E)-5-amino-1-(1-(4-(dimethylamino)-2-butenyl)-6-methylpiperidin-3-yl)-3-(4-phenoxyphenyl))-1H-pyrazole-4-carboxamide (WS-441) | 503 |

| Ex. No. | Structure | Name | MS (M + 1) |
|---|---|---|---|
| 38 | 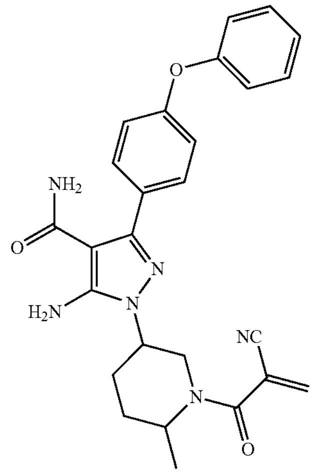 [SMILES: C=C(C#N)C(=O)N1CC(n2nc(-c3ccc(Oc4ccccc4)cc3)c(C(N)=O)c2N)CCC1C] | 5-amino-1-(1-(2-cyanoacryloyl)-6-methylpiperidin-3-yl)-3-(4-phenoxyphenyl)-1H-pyrazole-4-carboxamide (WS-442) | 471 |
| 39 | 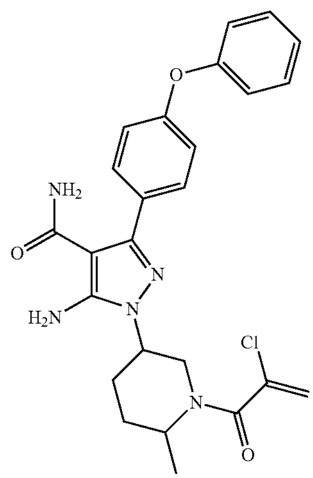 [SMILES: C=C(Cl)C(=O)N1CC(n2nc(-c3ccc(Oc4ccccc4)cc3)c(C(N)=O)c2N)CCC1C] | 5-amino-1-(1-(2-chloroacryloyl)-6-methylpiperidin-3-yl)-3-(4-phenoxyphenyl)-1H-pyrazole-4-carboxamide (WS-443) | 480 |
| 40 | 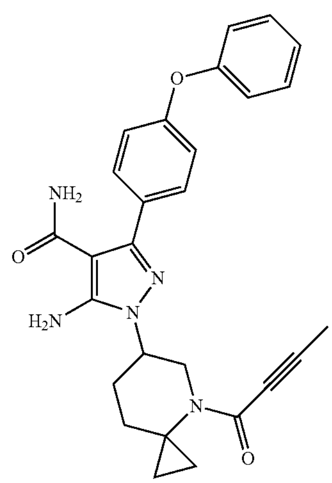 [SMILES: CC#CC(=O)N1CC(n2nc(-c3ccc(Oc4ccccc4)cc3)c(C(N)=O)c2N)CCC12CC2] | 5-amino-1-(4-(2-butynoyl)-4-azaspiro[2.5]oct-6-yl)-3-(4-phenoxyphenyl)-1H-pyrazole-4-carboxamide (WS-444) | 470 |

Example 41

Kinase Activity (BTK) Inhibition Assay

The inhibitory effects of the compounds disclosed herein on BTK kinase activity were tested in an assay based on a time resolved fluorescence resonance energy transfer (TR-FRET) method. Recombinant Btk was pre-incubated with the compound disclosed herein in an assay buffer containing 50 mM. Tris pH 7.4, 10 mM $MgCl_2$, 2 mM $MnCl_2$, 0.1 mM EDTA, 1 mM DTT, 20 nM SEB, 0.1% BSA, 0.005% tween-20 at room temperature for 1 hour. The reaction was initiated by the addition of ATP (at the ATP Km concentration) and the peptide substrate (Biotin-AVLESEEELYS-SARQ-NH$_2$). After incubation for 1 hour at room temperature, an equal volume of stop solution containing 50 mM HEPES pH 7.0, 800 mM KF, 20 mM EDTA, 0.1% BSA, p-Tyr66 antibody linked with Eu cryptate and streptavidin-labeled XL665 was added to stop the reaction. The plate was incubated for an additional hour at room temperature and then the TR-FRET signal was read on a BMG PHERAstar FS instrument (ex337 nm, em 620 nm/665 nm). Based on the ratio of the signal of fluorescence at 615 nm to 665 nm, the enzyme activity was calculated with an increased compound concentration. IC50 of each compound was obtained by fitting the data to the four-parameter equation of Graphpad Prism software.

According to the above experimental method, the compounds of the present invention exhibit inhibitory effect of BTK kinase (IC50<1000 nM), and some of the preferred compounds have very potent activity (IC50<100 nM). The specific results are shown in the table below.

| Compound No. | BTK kinase inhibitory activity grade (A/B/C) |
|---|---|
| WS-401 | A |
| WS-402 | B |
| WS-403 | B |
| WS-404 | B |
| WS-405 | A |
| WS-406 | A |
| WS-407 | A |
| WS-408 | A |
| WS-409 | A |
| WS-410 | A |
| WS-411 | A |
| WS-412 | C |
| WS-413 | A |
| WS-414 | B |
| WS-416 | A |
| WS-417 | B |
| WS-421 | A |
| WS-422 | A |

The kinase inhibitory activity grades are assigned to A, B, and C, specifically, A (IC$_{50}$<100 nM), B (100 nM<IC$_{50}$<1000 nM), C (IC$_{50}$>1000 nM).

Example 42

In Vitro Kinase Selectivity Assay

The assay platform for EGFR and ITK kinase activities was established using time-resolved fluorescence resonance energy transfer-based method; the assay platform for LCK, SRC and LYN kinase activities was established using Z'-Lyte method; and the assay platform for TEC and JAK3 kinase activities was established using Lance Ultra method. The inhibitory effects of the compounds disclosed herein on different kinase activities were tested separately for each compound at 11 concentrations. The IC50 value of each compound was calculated using Graphpad Prism software.

According to the above experimental methods, some compounds of the present invention exhibited very high kinase selectivity profile, which was significantly better than that of the control compound ibrutinib. See the table below for the results.

| Compound No. | LCK | SRC | LYN | EGFR | ITK | TEC |
|---|---|---|---|---|---|---|
| WS-411 | B | C | B | C | C | A |
| WS-413 | C | C | C | B | C | A |
| WS-416 | C | C | C | C | C | A |
| ibrutinib | A | A | A | A | A | A |

The kinase inhibitory activity grades are assigned to A, B, and C, specifically, A (IC$_{50}$<100 nM), B (100 nM<IC$_{50}$<1000 nM), C (IC$_{50}$>1000 nM).

Example 43

B Cell Inhibition Assay

Temporary exposure to a BTK inhibitor in vitro is sufficient to inhibit B cell activation in normal human B cells. This protocol mimics the predicted exposure of cells to the inhibitor in vivo, and shows that the inhibition of B cells is maintained even when the inhibitor was washed off.

B cells were obtained by purification from healthy donor blood through negative selection using the RosetteSep human B Cell Enrichment Mix. Cells were plated in a growth medium (10% RPMI+10% fetal bovine serum) and the inhibitor was added at specified concentrations. After incubation at 37° C. for 1 hour, the cells were washed three times, and each wash was used for 8-fold dilution in the growth medium. The cells were then stimulated with 10 µg/mL IgM F(ab')2 at 37° C. for 18 hours. Cells were subsequently stained with an anti-CD69-PE antibody and analyzed by flow cytometry using standard conditions.

It is determined according to the above method that the preferred compounds of the present invention have strong inhibitory activities against B cells with an IC$_{50}$ less than 10 nM.

Example 44

T Cell Inhibition Assay

T cells were obtained by purification of healthy donor blood through negative selections using the RosetteSep Human T Cell Enrichment Mix. Cells were plated in a growth medium (10% RPMI+10% fetal bovine serum) and the inhibitor was added at specified concentrations. After incubating for 1 hour at 37° C., the cells were washed three times, and each wash was used for 10-fold dilution in the growth medium. The cells were then stimulated with anti-CD3/CD28 coated beads (bead/cell ratio 1:1) for 18 hours at 37° C. Cells were subsequently stained with an anti-CD69-PE antibody and analyzed by flow cytometry using standard conditions. It is determined according to the above method that the preferred compounds of the present invention have very low or no inhibitory activity on T cells, with an IC$_{50}$ values higher than 4000 nM.

Example 45

Inhibition Assay on Human Whole Blood B Cells

Human whole blood (hWB) was obtained from healthy volunteers and blood was collected by venipuncture into a heparin sodium-anticoagulant Vacutainer tube. Test compounds were diluted 10 times in PBS to the required initial drug concentration), followed by three-fold serial dilutions with 10% DMSO in PBS to obtain a 9-point dose response curve. 5.5 µL of each diluted compound was added to the aiil 96-well V-bottom plate in duplicate; 5.5 µL of 10% DMSO in PBS was added to control and non-stimulated wells.

Human whole blood (100 μL) was added to each well, and after the plates were incubated for 30 minutes at 37° C. and in 5% $CO_2$, 100% humidity. An anti-human IgM F(ab')2 (Southern Biotech) (10 μL of 500 μg/mL, solution, 50 μg/mL final concentration) was added to each well (exepct for non-stimulated wells) with vortexing, and the plate was further incubated for another 20 hours. After 20-hour incubation, samples were incubated with 20 μL of fluorescent probe-labeled APC mouse anti-human CD69 (BD Pharmingen) for 30 minutes at 37° C. 5% $CO_2$, 100% humidity. Induced controls, unstained, and Angle-stained samples were included for compensationand initial voltage settings. The samples were then lysed with 1 ml of IX Pharmingen Lyse Buffer (BD Pharmingen) and the plate was centrifuged at 1500 rpm for 5 minutes. The supernatant was removed by aspiration, the remaining pellet was lysed with an additional 1 ml of IX Pharmingen Lyse Buffer, and the plate was centrifuged as above. The supernatant was aspirated off and the remaining pellet was washed in FACs buffer (PBS+1% FBQ). After centrifugation and removal of the supernatant, the pellet was resuspended in 150 μL of FACS buffer. The sample was transferred to a 96-well plate suitable for operating n the HTS 96-well system of the BD LSR II flow cytometer. Data were acquired using the excitation and emission wavelengths suitable for the used fluorophore, and the percent positive cell values were obtained using Cell Quest Software. Results were initially analyzed using FACS analysis software (Flow Jo). The IC50 values were then calculated using XLfit v3, Equation 201.

It is demonstrated, according to the above method, that the selected compounds of the present invention have strong inhibitory activities against B cells in human hole blood, with an IC50 value less than 200 nM.

Example 46

Stability Study of Compound in Liver Microsomes

1. The test compounds were dissolved in acetonitrile to prepare a stock solution having a concentration of 0.5 mM.

2. 2 μL of stock solution was added to a 1.5 ml centrifuge tube, and then 148 μL of phosphate, buffer (100 mM, pH 7.4) and 10 μL of liver microsome suspension (the protein concentration was 20 mg/ml) [BD Gentest] were added. The liver microsomes were derived from the species of human, dog, rat, and mouse; The control group was added with 158 μL of phosphate buffer (100 mM, pH 7.4).

3. The mixture obtained in step 2 was pre-incubated for 3 minutes in a 37° C. water bath; then 40 μL of NADPH generating system (containing NADP+: 6.5 mM, glucose 6-phosphate: 16.5 mM, $MgCl_2$: 16.5 mM, glucose 6-phosphate dehydrogenase: 2 U/ml) was added to initiate the reaction. The reaction system was incubated for 1 hour in a 37° C. water bath.

4. After the reaction was carried out for 1 hour, the centrifuge tube was removed from the water bath, and the reaction was terminated by adding 400 μL of acetonitrile, followed by vortexing for 3 minutes. Finally, the tube was centrifuged (13,000 rpm, 4° C.) for 5 minutes and the supernatant was taken for detection of the remaining drug concentration, Cr, by HPLC.

5. Process for preparing, in parallel, 0-minute reaction sample: the mixture prepared in step 2 was pre-incubated in a 37° C. water bath for 3 minutes. After removing it from the water bath, 400 μL of acetonitrile was added, followed by adding 40 μL of NADPH generating system. After vortexing for 3 minutes, centrifugation (13,000 rpm, 4° C.) was carried out for 5 minutes. The supernatant was taken for detection of the drug concentration C0 by HPLC.

6. After 60 minutes of incubation, the percentage of remaining drug in the incubation system was calculated as follows:

Remaining Drug (%)=Cr/C0×100%

According to the above experimental method, some of the selected compounds of the present invention exhibit improved microsomal stability with a residual percentage>30% in liver microsomes of various species.

Example 47

Evaluation of Compounds for Inhibition of CYP Enzyme

CYP enzyme metabolism is a main pathway for drug biotransformation, and the quantity and activity of CYP enzyme directly affect the activation and metabolism of drugs in vivo. As a major metabolic enzyme of exogenous compounds, cytochrome CYP is an important phase I drug metabolic enzyme that can catalyzes the oxidative and reductive metabolism of various exogenous compounds. CYP enzyme plays a very important role in the elimination of drugs, and is also the main factor that causes the drug interactions during a combination drug therapy.

METHOD: This experiment simultaneously determined the inhibitory effects of a compound on five CYP450 enzymes in human liver microsomes using the cocktail probe substrates approach. The human microsomes were from BD Gentest.

The experiment steps are as follows:

The reaction was carried out in 100 mM of phosphate buffer, with a total volume of 200 μL. The concentration of microsomes in the reaction system was 0.25 mg/mL, and the concentration of the test compounds was 20 μM, 6.67 μM, 2.22 μM, 0.74 μM, and 0.25 μM. The specific probe substrates and concentration were phenacetin (CYP1A2) 40 μM, dextromethorphan (CYP2D6) 5 μM, diclofenac (CYP2C9) 10 μM, S-mephenytoin (CYP2C19) 40 μM, testosterone (CYP3A4) 80 μM, respectively. The mixture was pre-incubated in a 37° C. thermostatic shaker for 5 minutes, and the NADPH-generating system (containing 1.3 mM NADP+, 3.3 mM glucose 6-phosphate, 0.4 U/L glucose 6-phosphate dehydrogenase, 3.3 mM $MgCl_2$) was added to start the reaction. After incubation for 45 minutes, the reaction was stopped by adding an equal volume of acetonitrile. The tube was vortexed and centrifuged at 13,000 rpm. The resulting supernatant was subjected to LC-MS-MS to determine the amount of produced metabolites. The specific metabolites were acetaminophen (CYP1A2), dextrorphan (CYP2D6), 4-hydroxydiclofenac (CYP2C9), 4-hydroxymefentoin (CYP2C19), and 6β-hydroxytestosterone (CYP3A4), respectively. Specific inhibitors used as reference are furaphylline (CYP1A2), quinidine (CYP2D6), sulfaphenazole (CYP2C9), tranylcypromine (CYP2C19), and ketoconazole (CYP3A4), respectively. The final result of this experiment is the calculated half inhibitory concentration, or IC50 value. IC50=((50%−lowest inhibition percentrage %)/(highest inhibition percentage %−lowest inhibition percentage %))×(highest concentration−lowest concentration)+lowest concentration.

According to the above experimental method, some selected compounds of the present invention have very low or no inhibitory effect on various CYP enzymes, showing that they have little influence on the metabolism of other drugs.

Example 48

Research Method for Pharmacokinetics of Compounds in Rats

1. Male SD rats (HFK) were acclimatized in the laboratory for 7 days after arrival.

2. Nine SD rats were randomly divided into 3 groups, 3 animals in each group. One group was dosed by oral gavage (p.o.), and the other group was dosed by tail vein injection (i.v.). Rats in the p.o. group were fasted overnight before drug administration.

3. After drug administration, blood samples were collected from the rats via the posterior orbital venous plexus approach at the following time points: I.V.: (before drug administration), 0.08 hours, 0.25 hours, 0.5 hours, 1 hour, 2 hours, 4 hours, 8 hours, 24 hours; P.O.: 0.08 hour, 0.25 hour, 0.5 hour, 1 hour, 2 hours, 4 hours, 8 hours, 24 hours. About 300 μl of blood were collected at each time point.

4. The collected blood samples were centrifuged at 12000 rpm for 5 minutes at 4° C., and then the upper plasma samples were collected and stored in a refrigerator at −20° C.

5. The experimental operations weres summarized in Table 4:

TABLE 4

Design of pharmacokinetics in vivo test of compounds in rats

| Administration route | i.vi administration | p.o. administration |
| --- | --- | --- |
| dosage | 2 mg/kg | 10 mg/kg |
| Concentration of administered formulation | 1.5 mg/ml | 0.75 mg/ml |
| Dosing volume | 2 ml/kg | 4 ml/kg |
| Dosing vehicle | DMSO/Tween 20/deionized water (1/0.5/28.5) | |
| Testing animals | 3 SD rats per group | |
| Blood-collection time point | 0.08, 0.25, 0.5, 1, 2, 4, 8, 24 hours | |

6. LC-MS/MS (UPLC-MS/MS: liquid chromatography Waters Acquity UPLC (USA) and mass spectrometry 5500 Q Trap (Applied Biosystem/MDS SCIEX) or HPLC-MS\MS (liquid chromatography Agilent 1200 series (USA) and mass spectrometry API 4000 (Applied Biosystem/MDS SCIEX)) was used to determine the concentration of the compound in the plasma. Typical detection conditions are as follows:

| HPLC | Agilent 1200 Series |
| --- | --- |
| Mobile phase gradient | A) acetonitrile (0.1% FA); B) water (0.1% FA) 0-2.5 min, A:B 22:75-95:5 2.5-5.0 min, A:B 95:5 5.0-8 min, A:B 22:75 |
| column | XSELECT C18 (2.1*50 mm, 3.5 um) |
| Column temperature | 45° C. |
| Flow rate | 0.6 ml/min |
| Injected dose | 5 ul |

| UPLC | Waters ™ Acquity UPLC |
| --- | --- |
| Mobile phase gradient | A) methanol (0.1% FA); B) water (0.1% FA) 0-1.5 min, A:B 10:90-95:5 1.5-3.0 min, A:B 95:5 3.0-4.5 min, A:B 10:90 |
| column | Acquity C18 (2.1*50 mm, 2.5 um) |
| Column temperature | 45° C. |
| Flow rate | 0.6 ml/min |
| Injected dose | 1 ul |

The pharmacokinetic parameters were calculated using the pharmacokinetic software WinNonlin [Model: Phoenix™ WinNonlin® 6.1; Manufacturer: Pharsight Corporation]. [Phoenix 1.1 User's Guide: p251-p300]

According to the above experimental method, the compounds which have been determined in the present invention exhibit a good bioavailability (>40%).

Example 49 hERG Binding Assay (Dofetillide Method)

The IC50 value of the compounds for hERG inhibition can be determined according to the method described in the patent application US20050214870 A1. Selected compounds of the present invention have very low or no inhibitory effect on hERG, with an IC50 value greater than 1000 nM.

Example 50

Pharmacodynamic Assay

Severe immunodeficiency NOD.SCID mice were purchased from Beijing Vital River Laboratory Animal Technology Co., Ltd., and were housed in SPF grade animal room. After TMD-8 cells were cultured to the sufficient amount, the cells were collected by centrifugation and washed twice with PBS. Finally, the cells were resuspended in serum-free RPMI 1640 medium plus Matrigel (1:1 v/v). 0.2 ml of cell suspension was injected subcutaneously on the right flank of each mouse using 1 ml syringe and 25 G syringe needle. The tumor size was measured with a caliper after about one week post injection. The tumor volume was calculated according to the following formula: tumor volume=(length×width$^2$)/2. When the tumor volume reached about 100-200 mm$^3$, the mice were grouped and p.o. administered daily for 21 days.

Compounds WS411, WS413, WS416, and WS422 significantly inhibited the growth of diffuse large B-cell lymphoma cell line TMD-8 in vivo and showed the same anti-tumor effects as the control compound Ibrutinib (see FIG. 1 for experimental results).

INDUSTRIAL APPLICABILITY

The novel 5-aminopyrazole carboxamide derivative provided by the present invention is an effective, safe and highly selective inhibitor of protein kinase BTK, and can be used as a drug for treating BTK mediated diseases.

The invention claimed is:

1. A 5-aminopyrazole carboxamide compound represented by the formula (IV):

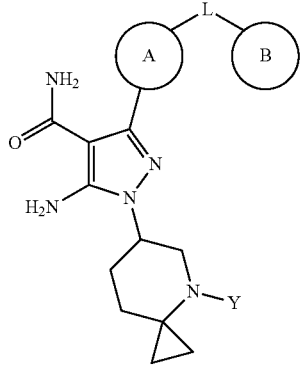

(IV)

wherein,

L is O, —C(O)NH—, —CH$_2$—, S, S(O), NH or S(O)$_2$;

A is selected from a substituted or unsubstituted benzene ring, or a substituted or unsubstituted heteroaryl ring, and its attachment sites to the parent nucleus and L are arbitrarily selected;

B is independently selected from a substituted or unsubstituted benzene ring, or a substituted or unsubstituted heteroaryl ring, and its attachment site to L is arbitrarily selected;

Y is —CN,

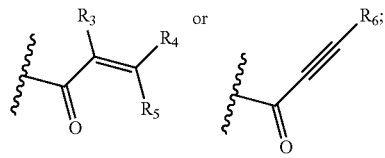

wherein R$_3$, R$_4$, R$_5$ and R$_6$ are each independently selected from hydrogen, unsubstituted C$_1$-C$_4$ alkyl, hydroxy-substituted C$_1$-C$_4$ alkyl, C$_1$-C$_4$ alkoxy C$_1$-C$_4$ alkyl, halogen, cyano or —(CH$_2$)$_q$N(R$^a$R$^b$), wherein q is 1, 2, 3, or 4, and R$^a$ and R$^b$ are each independently selected from hydrogen, or unsubstituted C$_1$-C$_4$ alkyl;

or a stereoisomer, a tautomer, a pharmaceutically acceptable salt, a solvate, or a prodrug thereof.

2. The compound according to claim 1, wherein L is O; B is

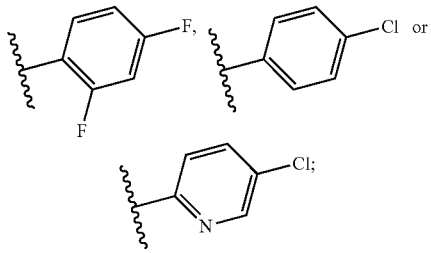

and

Y is —CN,

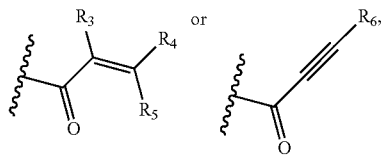

wherein R$_3$, R$_4$, R$_5$ and R$_6$ are each independently selected from hydrogen, unsubstituted C$_1$-C$_4$ alkyl, hydroxy-substituted C$_1$-C$_4$ alkyl, C$_1$-C$_4$ alkoxy C$_1$-C$_4$ alkyl, halogen, cyano or —(CH$_2$)$_q$N(R$^a$R$^b$), wherein q is 1, 2, 3, or 4, and R$^a$ and R$^b$ are each independently selected from hydrogen, or unsubstituted C$_1$-C$_4$ alkyl.

3. The 5-aminopyrazole carboxamide compound according to claim 1, which is represented by one of the following compounds:

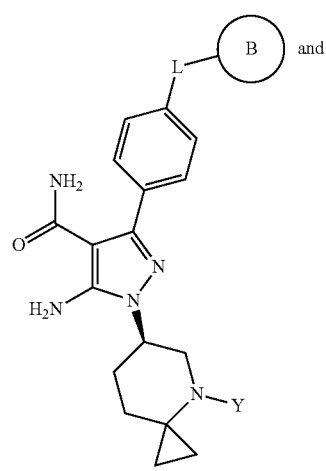

(IV-1)

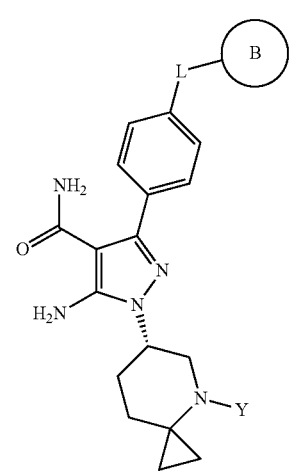

(IV-2)

wherein L, B and Y in the formula (IV-1) or (IV-2) are defined as in the above formula (IV), or a stereoisomer, a tautomer, a pharmaceutically acceptable salt, a solvate, or a prodrug thereof.

4. A compound selected from the following:
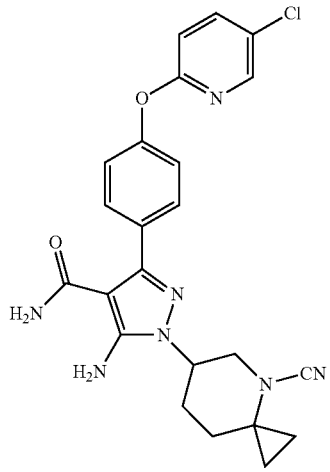
WS-405
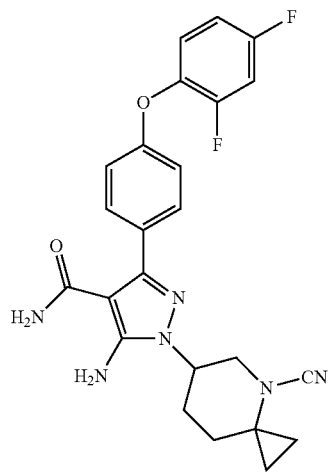
WS-408
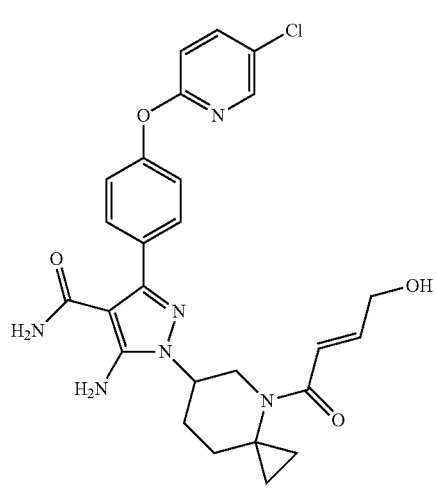
WS-406
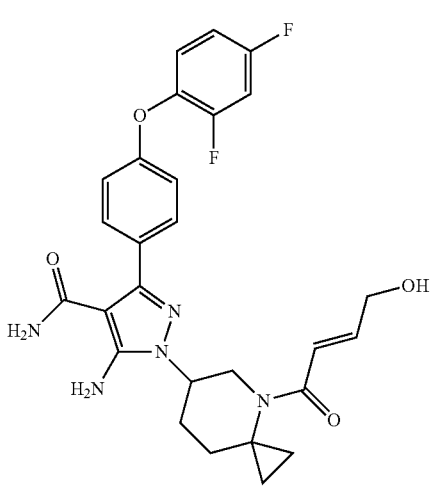
WS-409
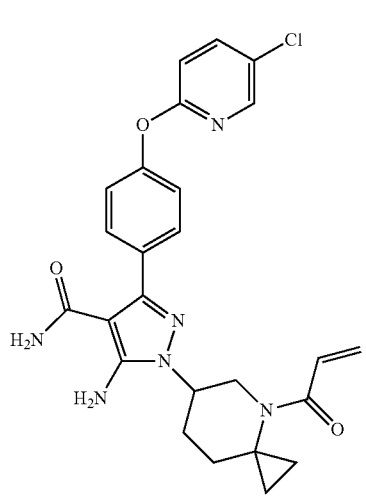
WS-407
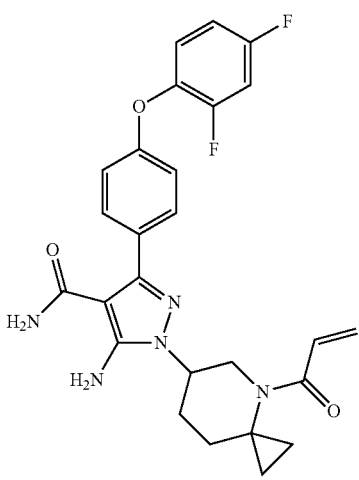
WS-410

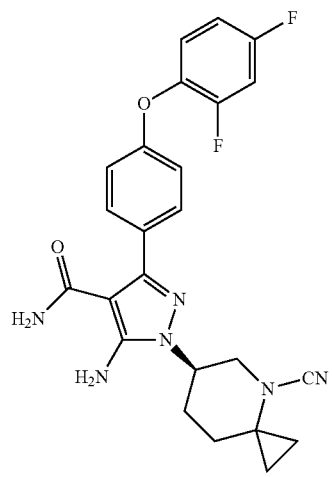
WS-411
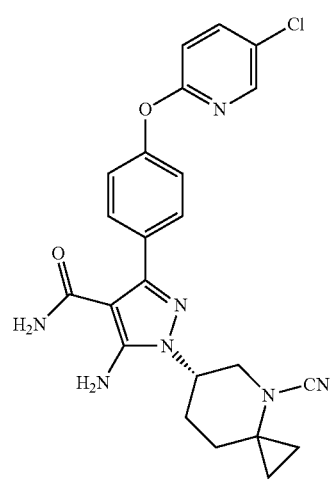
WS-414
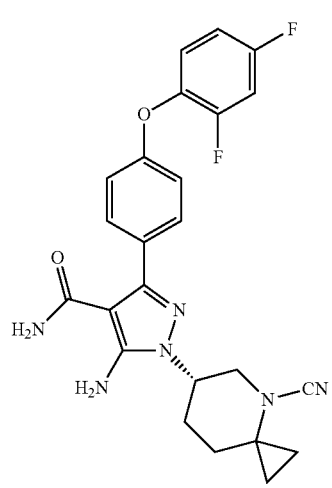
WS-412
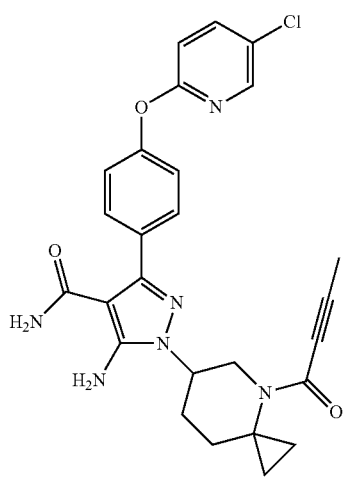
WS-415
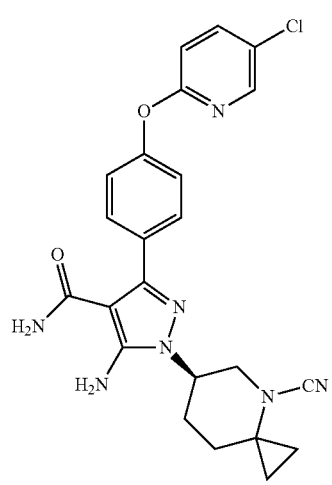
WS-413
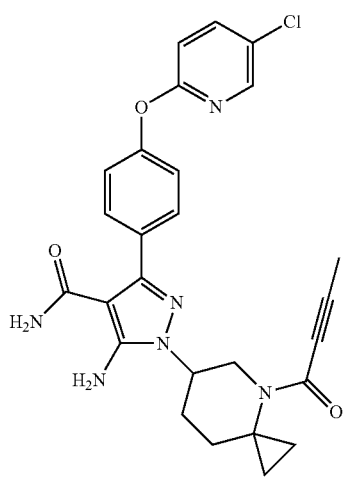
WS-416

WS-417
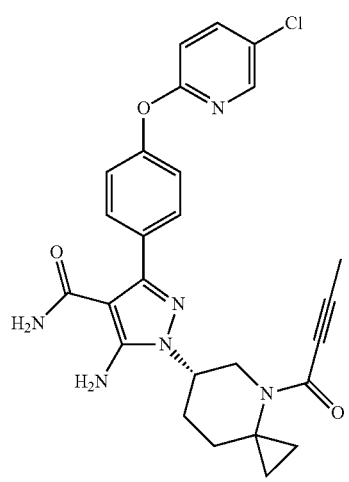
WS-420
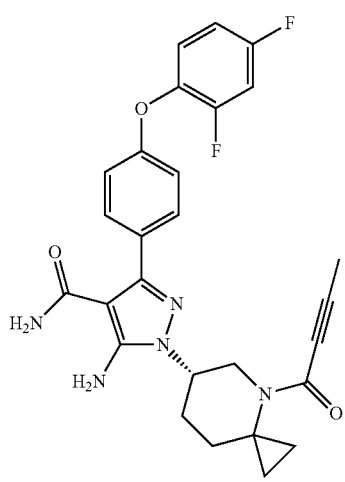
WS-418
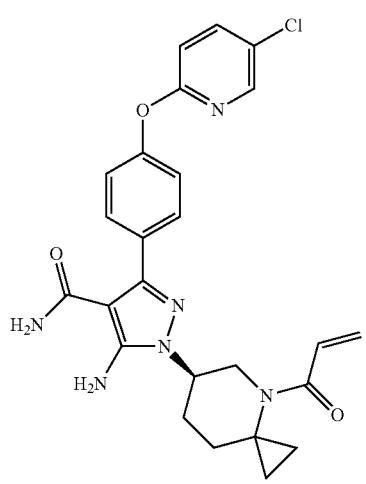
WS-421
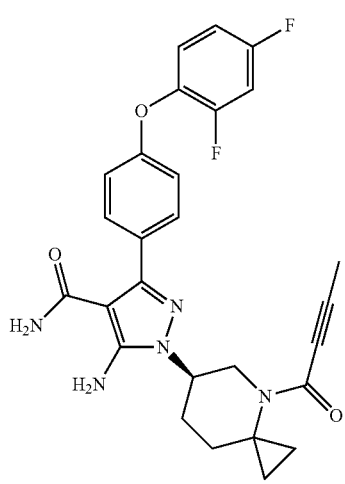
WS-419
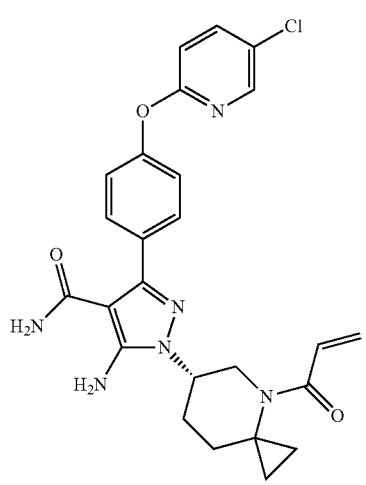
WS-422
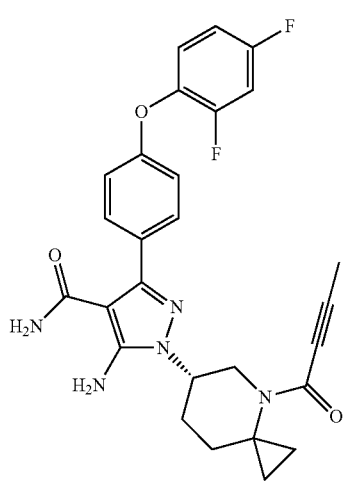

-continued

WS-431

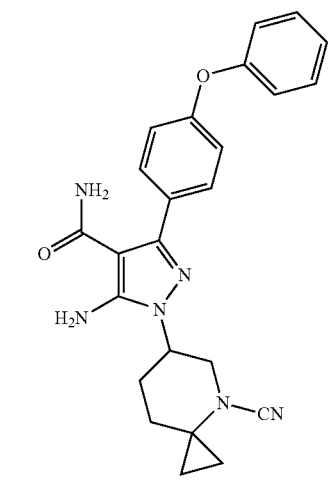

and

WS-433

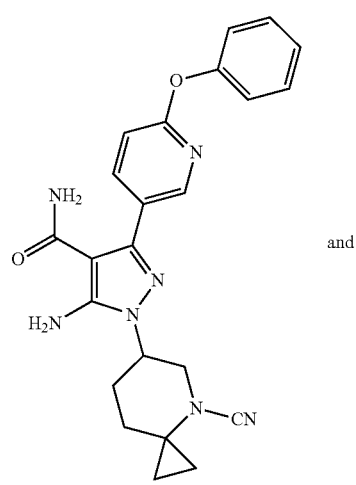

WS-444

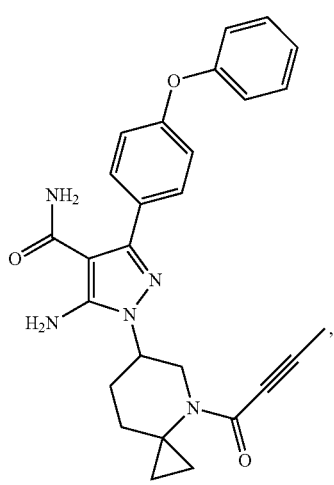

or a pharmaceutically acceptable salt, a solvate, or a prodrug thereof.

5. A pharmaceutical composition comprising the compound of claim 1 or 4 or a pharmaceutically acceptable salt thereof.

6. A method for preparing the compound according to 4, comprising:

(1) Reaction of the compound of formula (V) with the compound of formula (VI) to provide the compound of formula (VII);

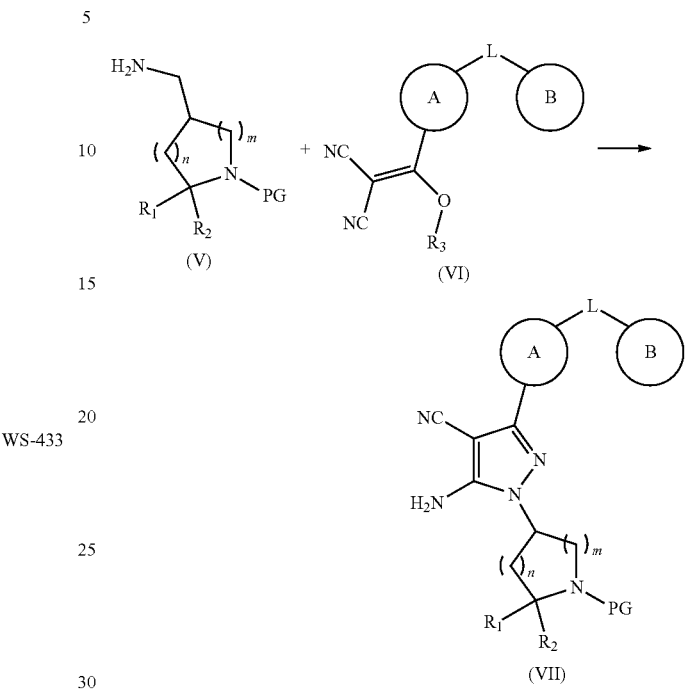

(2) Hydrolysis of the compound of formula (VII) to give the compound of formula (VIII);

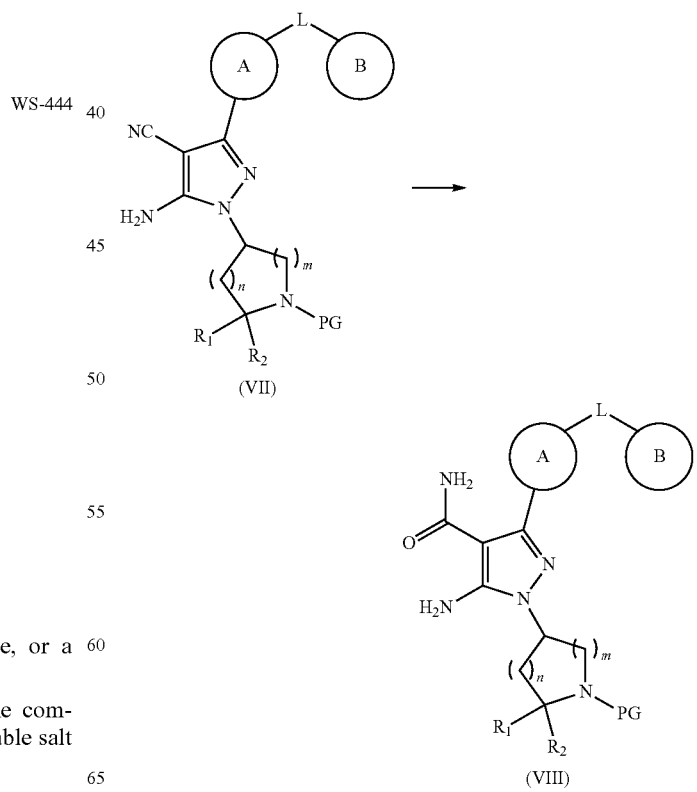

(3) Removal of the protection group PG from the compound of formula (VIII) to provide the compound of formula (IX);

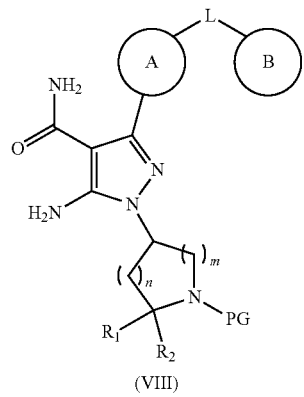

(VIII)

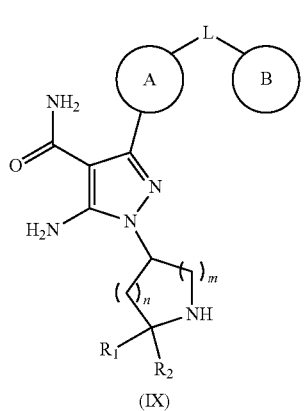

(IX)

(4) Reaction of the compound of formula (IX) with the compound of formula (X) to provide the compound of formula (I);

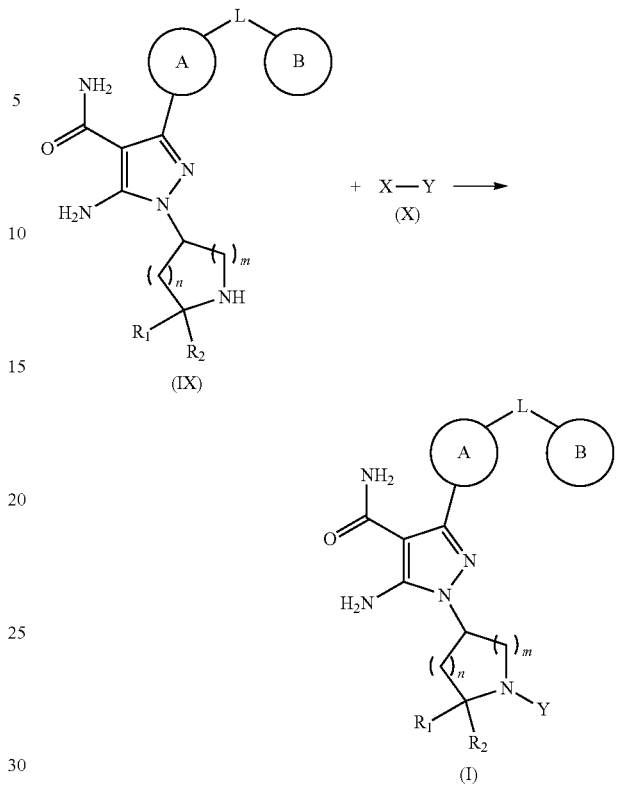

The substituents $R_1$, $R_2$, L, A, B, Y, and m and n in the above formula (V), formula (VI), formula (VII), formula (VIII), formula (IX) and formula (X) are defined as for formula (I), PG is an amino protecting group, $R_3$ is a $C_1$-$C_4$ alkyl group, preferably ethyl, and X is chloro, bromo or hydroxyl.

7. A method of treating a disease mediated by BTK, by administration of an effective amount of the composition of claim 5 wherein the disease is selected from the group consisting of autoimmune diseases, inflammatory diseases, xenogeneic immune conditions or diseases, thromboembolic diseases, and cancers.

* * * * *